(12) United States Patent
Cole

(10) Patent No.: US 10,967,081 B2
(45) Date of Patent: Apr. 6, 2021

(54) UV GERMICIDAL DEVICES, SYSTEMS, AND METHODS

(71) Applicant: UV Partners, Inc., Wyoming, MI (US)

(72) Inventor: Theodore John Cole, Wyoming, MI (US)

(73) Assignee: UV Partners, Inc., Grand Haven, MI (US)

( * ) Notice: Subject to any disclaimer, the term of this patent is extended or adjusted under 35 U.S.C. 154(b) by 0 days.

(21) Appl. No.: 15/364,242

(22) Filed: Nov. 29, 2016

(65) Prior Publication Data

US 2017/0296686 A1 Oct. 19, 2017

Related U.S. Application Data

(63) Continuation of application No. PCT/US2015/033434, filed on May 30, 2015.

(60) Provisional application No. 62/119,157, filed on Feb. 21, 2015, provisional application No. 62/005,437, filed on May 30, 2014.

(51) Int. Cl.
*A61L 2/10* (2006.01)
*A61L 2/00* (2006.01)
*A61L 2/24* (2006.01)
*A61L 2/26* (2006.01)

(52) U.S. Cl.
CPC ............... *A61L 2/10* (2013.01); *A61L 2/0047* (2013.01); *A61L 2/24* (2013.01); *A61L 2/26* (2013.01); *A61L 2202/11* (2013.01); *A61L 2202/14* (2013.01)

(58) Field of Classification Search
CPC ........................................................ A61L 2/10
See application file for complete search history.

(56) References Cited

U.S. PATENT DOCUMENTS

| 2006/0188389 | A1 | 8/2006 | Levy | |
|---|---|---|---|---|
| 2009/0117001 | A1 | 5/2009 | Hyde et al. | |
| 2011/0215261 | A1 | 9/2011 | Lyslo et al. | |
| 2011/0286883 | A1* | 11/2011 | Hecht | A23L 3/28 422/24 |
| 2012/0282135 | A1* | 11/2012 | Trapani | A61L 2/10 422/3 |
| 2013/0045132 | A1* | 2/2013 | Tumanov | A61L 2/10 422/24 |

(Continued)

FOREIGN PATENT DOCUMENTS

WO 2011/143265 11/2011

OTHER PUBLICATIONS

International Search Report and the Written Opinion of the International Searching Authority for International Application No. PCT/US2015/033434 dated Aug. 12, 2015.

(Continued)

*Primary Examiner* — Donald R Spamer
(74) *Attorney, Agent, or Firm* — Warner Norcross + Judd LLP

(57) ABSTRACT

A germicidal system for use in disinfecting one or more contact surfaces includes one or more germicidal devices each comprising a germicidal light source. The one or more germicidal devices may be connected to a network, which allows for controlling the operational parameters of the one or more germicidal devices and/or collecting information from the one or more germicidal devices.

24 Claims, 33 Drawing Sheets

(56) References Cited

U.S. PATENT DOCUMENTS

2013/0062534 A1   3/2013   Cole
2019/0022260 A1   1/2019   Cole

OTHER PUBLICATIONS

Non-final Office Action for U.S. Appl. No. 15/983,805 dated Nov. 2, 2018.
Final Office Action for U.S. Appl. No. 15/983,805 dated Jun. 21, 2019.

\* cited by examiner

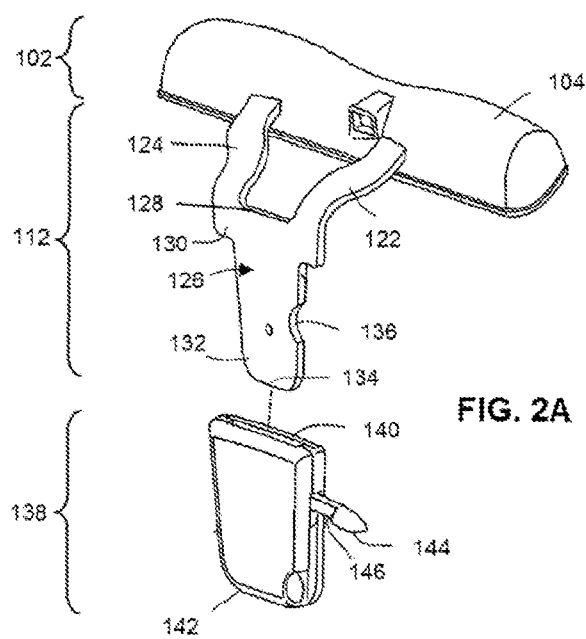
FIG. 2A
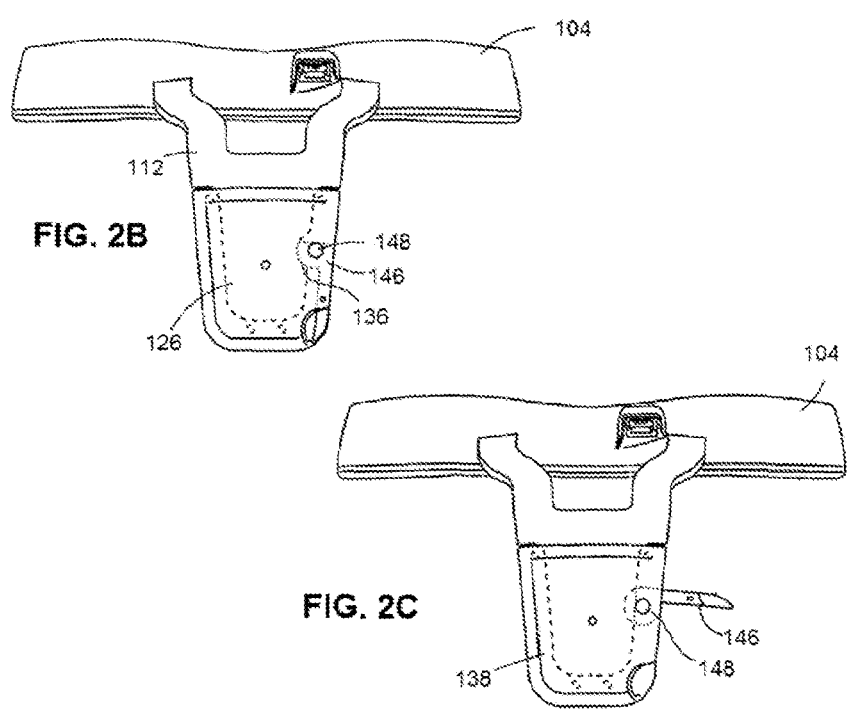
FIG. 2B
FIG. 2C

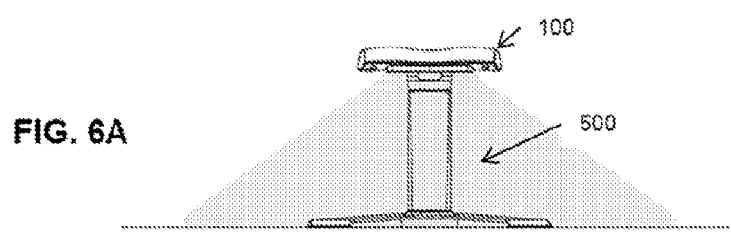
FIG. 6A
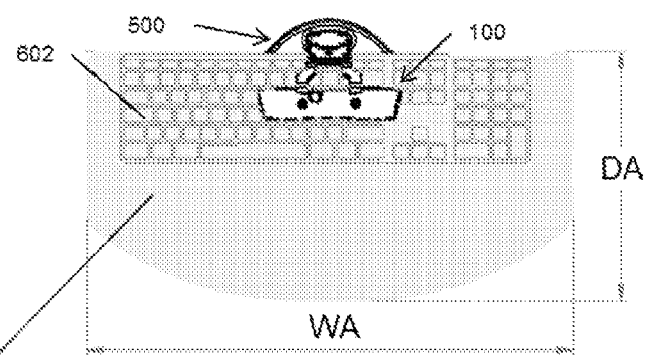
FIG. 6B
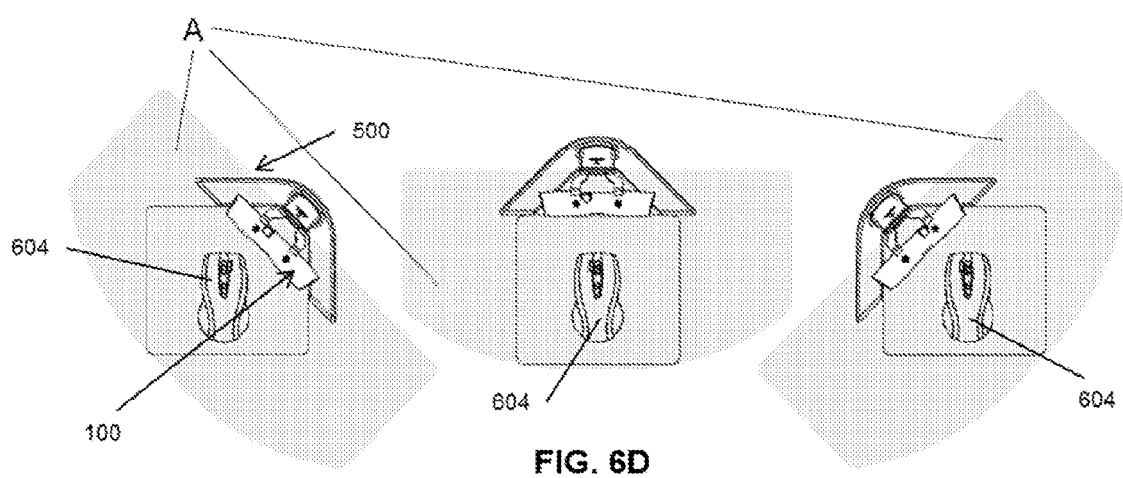
FIG. 6C
FIG. 6D
FIG. 6E

UV GERMICIDAL DEVICES, SYSTEMS, AND METHODS

CROSS-REFERENCE TO RELATED APPLICATIONS

This application is a continuation of PCT Patent Application Serial No. PCT/US2015/033434, filed on May 30, 2015, which claims priority to U.S. Provisional Application Ser. No. 62/005,437, filed May 30, 2014, and titled "UV GERMICIDAL SYSTEM AND METHOD USING DEVICE IDENTIFICATION AND DISINFECTION PROTOCOL," and to U.S. Provisional Application Ser. No. 62/119,157, filed Feb. 21, 2015, and titled "UV GERMICIDAL SYSTEM AND METHOD," each of which is hereby incorporated by reference in its entirety.

FIELD

The present invention relates generally to germicidal devices, systems, and methods, including a system for centralized control, monitoring, storage, and/or analysis of a plurality of germicidal devices connected to a network.

BACKGROUND

Healthcare workers wash their hands often in an attempt to prevent transmission of hospital acquired infections. However, a large number of hospital patients still become infected by nosocomial (healthcare acquired) infections. Computers with bacteria ridden surfaces already present in hospital rooms or brought into a room by a healthcare worker to perform an exam or procedure may be to blame. The hands of healthcare workers may become infected when they touch the computer surface. The infection can then be passed on to patients and other surfaces in the room.

In efforts to solve this health hazard, current practices include using disinfectant wipes to wipe down the surfaces. However, to have any antimicrobial affect, most wipes require a surface to remain wet with disinfecting solution for at least 30 seconds. This manual disinfection method is time and labor intensive, and as such is unlikely to be done as frequently as required to limit transmission. Antibacterial treatment of surfaces may not be ideal either as it takes several hours to kill bacteria deposited on them, which may prohibit any real impact on the pathogen transfer mechanism. Further, as chemical disinfectants, like antibiotics, have been overused, super resistant strains of bugs are being created that require new solutions. Additional methods of disinfection are thus desirable.

BRIEF SUMMARY

Described herein are solutions to keep computer and other equipment surfaces at a level of disinfection sufficient to reduce or eliminate bacteria that is transferred to the hands of healthcare workers when they touch the surfaces. For example, computer and other surfaces may be disinfected periodically and/or after use. Disclosed herein is a germicidal system and method for automatically disinfecting the contact surfaces using a germicidal light source, such as a low intensity ultraviolet (UV) light, that is intelligently controlled. The germicidal systems described herein may comprise one or more germicidal devices having sensors to monitor for human activity. In some variations, the germicidal devices may have a single type of sensor to monitor for human activity. In other variations, the germicidal devices may have two or more types of sensors to monitor for human activity. In these instances, the germicidal devices may comprise one or more proximity sensors (e.g., a passive infrared sensor) as well as one or more interaction sensors using software monitoring of existing computer input devices (e.g., keyboard, mouse, touchpad, touchscreen) for activity. In some instances, the sensors may be integrated into a control system. The control system may be configured to turn the germicidal light source on in response to contact with the contact surface, and may be configured to turn the light off in response to presence of a user. In some variations, the control system may further be configured to turn the germicidal light source on periodically, not in response to contact with the contact surface. Such a control system may reduce risks associated with human exposure to germicidal light sources, while achieving increased effectiveness.

One or more of the germicidal devices described herein may be integrated into a germicidal system and may be configured to exchange information with one or more remote devices and/or servers over a network. The network may allow for control of and/or data collection from the one or more germicidal devices. For example, the germicidal system may include a hosted, web-based management system connected to each of the one or more germicidal devices on the network within a facility (e.g., a hospital or hospital system). The management system may be configured to collect data from one or more germicidal devices on the network. For example, the administrator interface may be used to monitor and report on the disinfection statistics of one or more germicidal devices, as well as to track other factors, such as when portions of the devices (e.g., bulbs) may need to be replaced. The administrator interface may additionally or alternatively be configured to control one or more germicidal devices on the network. For example, the administrator interface may be used to modify one or more operational parameters of one or more germicidal devices.

It should be appreciated that the germicidal systems, devices, and methods described herein may be applied not only in healthcare facilities, but anywhere where computers or other interactive devices or surfaces are used in a shared environment, such as but not limited to restaurants, airports, schools, universities, self-checkout stations in grocery stores, and the like.

Described herein are systems for disinfecting one or more surfaces. In some variations, the systems may comprise a germicidal device, a server, and an administrator device. The germicidal device may comprise a germicidal light source and a proximity sensor. The server may be communicatively coupled to the germicidal device via a network, wherein the server is configured to provide instructions to the germicidal device and to receive input from the germicidal device via the network. The administrator device may be communicatively coupled to the server, wherein the administrator device comprises an administrator interface, and wherein the administrator device is configured to receive input via the administrator interface and to provide instructions to the server via the network. In some of these variations, the server may be indirectly communicatively coupled to the germicidal device via a human interface device, and the one or more surfaces to be disinfected may be part of or a peripheral device of the human interface device. In some of these variations, the system may further comprise a second germicidal device comprising a germicidal light source and a proximity sensor, and the server may be communicatively coupled to the second germicidal device via the network. In some of these variations, the germicidal device may be wirelessly connected to the network.

Also described herein are methods for controlling a germicidal system. The germicidal system may comprise at least one germicidal device communicatively coupled to an administrator device via a network. In some variations, the method may comprise receiving, at an administrator device, an administrator input via an administrator interface, and in response to the administrator input, adjusting one or more operational parameters of the at least one germicidal device. In some of these variations, the germicidal system may comprise a plurality of germicidal devices communicatively coupled to the administrator device via a network. In some of these variations, the one or more operational parameters may comprise at least one of a disinfecting cycle duration, delay period, periodic cycle duration, and periodic interval. In some of these variations, at least one of the disinfecting cycle duration and the periodic cycle duration may be increased. In some of these variations, the increase may be in response to a *Clostridium difficile* outbreak. In some variations, the administrator input may comprise a selection of at least one of the plurality of germicidal devices. In some variations, the administrator input may comprise a selection of at least two of the plurality of germicidal devices. In some variations, the administrator input may comprise a selection of one or more operational parameters of at least one of the plurality of germicidal devices. In some variations, the administrator input may comprise a selection of one or more operational parameters of at least two of the plurality of germicidal devices. In some variations, adjusting one or more operational parameters of the at least one germicidal device comprises transmitting instructions to the at least one germicidal device.

Also described herein are methods for disinfecting a surface using a germicidal device. The germicidal device may comprise a germicidal light source and a proximity sensor, and the germicidal device may be connected to a human interface device. In some variations, the method may comprise, in response to detecting an interaction with the human interface device, beginning a disinfection cycle, wherein the disinfection cycle comprises irradiating the surface using the germicidal light source for a disinfection cycle duration, and beginning a periodic disinfection cycle, wherein the periodic disinfection cycle comprises irradiating the surface using the germicidal light source for a periodic cycle duration. In some of these variations, the periodic cycle duration may be longer than the disinfection cycle duration. In some of these variations, the periodic cycle duration may be between 0.5 and 4 times the disinfection cycle duration. In some variations, the method may further comprise ending at least one of the disinfection cycle and the periodic disinfection cycle in response to detection of interaction with the human interface device, and pausing at least one of the disinfection cycle and the periodic disinfection cycle in response to a detection event by the proximity sensor.

Also described herein are methods for generating a report related to a germicidal system. The germicidal system may comprise at least one germicidal device communicatively coupled to a server via a network, and an administrator device communicatively coupled to the server and configured to receive administrator input. In some variations, the method may comprise, generating a report in response to receiving administrator input, wherein the report contains information related to the at least one germicidal device. In some of these variations, the information may comprise a number of completed disinfection cycles by the at least one germicidal device within a time period. In some of these variations, the system may comprise a plurality of germicidal devices communicatively coupled to the server via the network. In some of these variations, the information may comprise a number of completed disinfection cycles by at least two of the plurality of germicidal devices within a time period. In some of these variations, the report contains information related to at least two of the plurality of germicidal devices. In some of these variations, the administrator input may comprise a selection of at least two of the plurality of germicidal devices. In some variations, the administrator input comprises one or more report parameters.

Also described here are germicidal systems for use in disinfecting a human interface device. Generally, the systems may comprise at least one human interface device, at least one ultraviolet light source in proximity to the at least one human interface device for disinfecting a contact surface of the human interface device, and a sensing system configured to detect when the contact surface should be disinfected, and configured to detect when a person is near or in an irradiation area of light produced by the at least one ultraviolet light source. In some variations, the sensing system may comprise a proximity sensor. In some variations, the sensing system may comprise an interaction sensor that detects interaction with one or more inputs of the human interface device. In of variations, the sensing system may comprise a proximity sensor and an interaction sensor that detects interaction with one or more inputs of the human interface device. In some of these variations, the one or more inputs may comprise at least one of a keyboard, mouse, and touchscreen.

Also described here are germicidal systems for use in disinfecting a contact surface. Generally, the germicidal systems may comprise at least one human interface device, at least one a germicidal device in proximity to the at least one human interface device, a server communicatively coupled to the at least one germicidal device via a network, and a computer in communication with the server for controlling operational parameters of the germicidal device. In some variations, the operational parameters may comprise a duration of a disinfection cycle.

Also described here are germicidal systems for use in disinfecting a contact surface where the germicidal systems may generally comprise at least one germicidal device. The germicidal device may comprise a germicidal light source and a controller system configured to turn the germicidal light source on and off. The germicidal device may comprise at least one proximity sensor. In some variations the proximity sensor may be a passive infrared sensor. In some variations the proximity sensor may be a heat sensor. In some variations, the germicidal device may comprise both a passive infrared sensor and a heat sensor. In some variations, the germicidal device may be configured to be wireless connected to a network. In other variations, the germicidal device may be configured to be connected to a network via a human interface device. In some of these variations, the controller system may receive input regarding interaction with the human interface device, or regarding interaction with a peripheral device of the human interface device. The germicidal light source may in some variations be a cold cathode fluorescent lamp. In some variations, the germicidal device may be configured such that when the germicidal light source is on, at 10 cm directly below the germicidal light source, the intensity at a central wavelength may be less than 500 $\mu W/cm^2$. In some variations, the germicidal device may be configured such that when the germicidal light source is on, at 10 cm directly below the germicidal light source, the intensity at a central wavelength may be less than 300 µW/cm². In some variations, the germicidal device may be configured such that when the germicidal light source is on, at 10 cm directly below the germicidal light source, the intensity at a central wavelength may be less than 100 µW/cm². In some variations, the germicidal device may be configured such that when the germicidal light source is on, at 10 cm directly below the germicidal light source, the intensity at a central wavelength may be less than 50 µW/cm². In some variations, the germicidal device may comprise a lens, wherein the lens comprises a material that partially attenuates ultraviolet light. In some of these variations, the lens may be configured to attenuate ultraviolet light by 50%. In some of these variations, the lens may have a thickness between 2 mm and 4 mm. In some of these variations, the lens may comprise a polymer. In some of these variations, the lens may comprise cyclic olefin copolymer. In some of these variations, the lens may be removable and replaceable.

Also described here are germicidal devices. Generally, the germicidal devices may comprise a light assembly and a mounting assembly. In some variations, the mounting assembly may comprise a receptacle. The receptacle may be configured to receive an object comprising a contact surface to be disinfected. In some of these variations, the receptacle may be configured to receive a mouse. The mounting assembly may be configured such that when the object is placed within the receptacle, a germicidal light source of the light assembly is configured to illuminate the contact surface of the object. In some variations, the receptacle may comprise a surface configured to support the object. In some of these variations, the receptacle may comprise one or more sides to help secure the object in place within the receptacle. In some variations, the mounting assembly may comprise an extension attached at a first end to the light assembly. In some variations, the receptacle may comprise a mounting lip, which may be configured to be mounted to a mounting surface. In other variations, the mounting assembly may comprise a receptacle housing rotatably coupled to a panel. The panel may be configured to attach to a human interface device. In some variations, panel may be configured to attach to the rear surface of a laptop LCD screen. The mounting assembly may comprise a first configuration in which the receptacle housing is adjacent to the panel and a second configuration in which the receptacle housing is rotated away from the panel.

BRIEF DESCRIPTION OF THE DRAWINGS

FIGS. 2A and 2B-2C are exploded and assembled views, respectively, of the germicidal device of FIGS. 1A-1C comprising an exemplary mounting assembly.

FIGS. 6A-6B show front and top views of the germicidal device and stand of FIGS. 5A-5D used with a keyboard. FIGS. 6C-6E show top views of the germicidal device and stand of FIGS. 5A-5D used with a mouse.

DETAILED DESCRIPTION

Overview

Figure 1A:
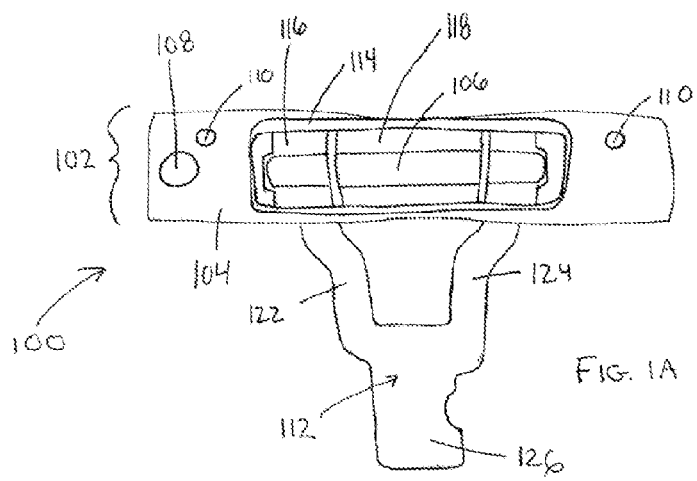
FIGS. 1A-1C show perspective views of an exemplary germicidal device.

The germicidal devices, systems, and methods described herein may be used to reduce the risk of bacteria or virus transmission on contact surfaces. In some instances the contact surfaces may be all or a portion of an electronic human interface device or its peripheral devices, such as but not limited to notebook computers, desktop computers, touchscreen computers or portable computing devices, tablet computers, kiosks, point-of-sale screens, keyboards, mice, cash registers, automated teller machines, credit card payment devices (e.g., at grocery store check-out aisles), portions of these devices, or the like. In other instances, the contact surfaces may be all or a portion of a non-interactive object, such as but not limited to a countertop, a sink, a doorknob, or the like.

The germicidal devices described herein may be capable of automatically cleaning the contact surfaces using irradiation, such as UV irradiation. Use of a germicidal device as described herein may be particularly desirable in situations wherein contact surfaces are typically touched by more than one person, such as but not limited to medical environments, educational institutions, libraries, government entities, business, and the like, where failure to disinfect these surfaces may increase the likelihood of transmission of contagions between staff members, patients, customers, and/or other persons. The systems may also be desirable in situations in which it may be impractical to use sprays or wipes because physically touching the surfaces can easily press the input mechanisms (e.g., keys or mouse buttons) and produce erroneous data entries.

The germicidal devices described herein may comprise one or more germicidal light sources. Generally, the germicidal light source may be configured to project light onto a contact surface to irradiate and disinfect the contact surface. The germicidal system may be configured to irradiate the contact surface between users touching the contact surface (e.g., using or accessing a human interface device) to at least partially disinfect the target area. The germicidal device may comprise a controller system, which may be configured to drive the germicidal light source according to the disinfection methods described herein.

One or more germicidal devices described herein may be connected via a network into a germicidal system. The germicidal systems described herein may comprise software configured to direct one or more processors of the germicidal system to perform a wide variety of functions. For example, software may contribute to the control of automatic operations of the germicidal system, and software may enable a user to manually adjust operational parameters of the germicidal system via a user interface. Software may be configured to control the flow or transmission of data between devices of the germicidal system, and it may enable the germicidal system to collect, store, and/or analyze the transmitted data. A germicidal system may also comprise one or more germicidal devices and/or human interface devices that are configured to exchange information with one or more remote devices and/or servers over a network. This may allow for centralized control of all or a portion of the germicidal and/or human interface devices that are connected to the network. The germicidal system may allow for centralized monitoring, storage, and/or analysis of data obtained from all or a portion of the germicidal and/or human interface devices that are connected to the network.

Germicidal Device

Light Assembly

Figure 1B:
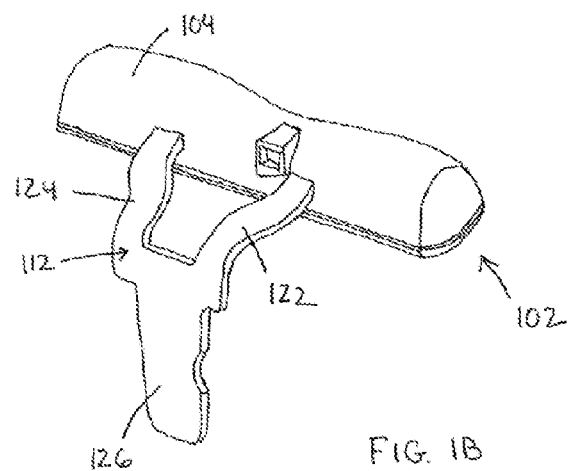
Figure 1C:
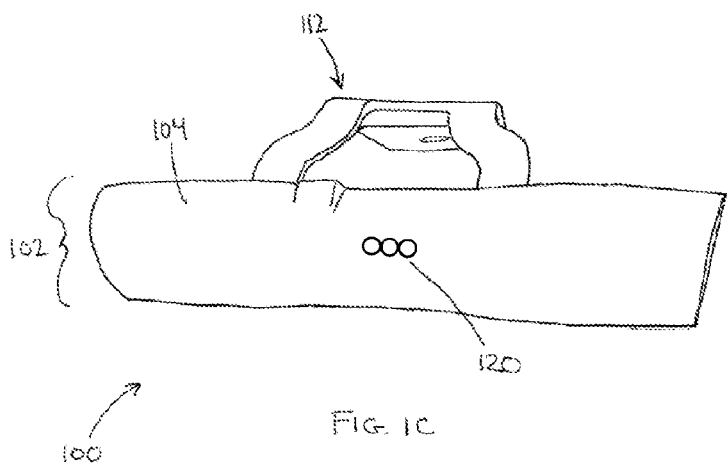

An exemplary germicidal device 100 is shown in FIGS. 1A-1C. The germicidal device 100 may comprise a light assembly 102 comprising a housing 104 and one or more germicidal light sources 106. The light assembly 102 may also optionally comprise one or more sensors 108 and/or one or more work lights 110, as described in more detail herein.

Housing

As shown in FIG. 1A, the housing 104 may comprise a recess 116 configured to receive the germicidal light source 106, and may comprise a flange or skirt 114 around the recess and extending from the housing. The housing 104 may be sized and shaped to allow light to be projected through an opening in the housing while reducing light exposure to areas outside the boundaries that define a contact area desired to be disinfected. That is, the flange or skirt 114 may help to reduce side exposure incidents and low side angles with respect to the germicidal light source 106. A reflective material 118 may optionally be located within at least a portion of an interior of the housing 104, such that at least a portion of light that is initially directed away from the contact surface may be reflected and re-directed towards the contact surface.

While not shown in the variation of FIGS. 1A-1C, in other variations the light assembly may comprise a lens. The lens may be configured to at least partially extend over the opening in the housing and may provide protection for the germicidal light source, affect the illumination pattern projected by the germicidal light source (e.g., change the size of the illumination pattern, change the shape of the illumination pattern, change the intensity of the illumination pattern), or a combination thereof. For example, in some variations, the lens may comprise a material that partially filters light emitted from the germicidal light source (e.g., UVC light). In one variation, the lens may comprise a polymer, such as cyclic olefin copolymer, that is configured to partially filter UVC light, i.e., allow a portion of UVC light to pass through the material, while preventing another portion of UVC light to pass through the material. In such a way, the light emitted from the germicidal light source may be attenuated. The material properties and/or thickness of a lens may be selected to achieve a desired attenuation, for example between about 5% and about 95%, between about 10% and about 90%, between about 15% and about 85%, between about 20% and about 80%, between about 25% and about 75%, between about 30% and about 70%, between about 35% and about 65%, between about 40% and about 60%, between about 45% and about 55%, about 40%, about 45%, about 50%, about 55%, or about 60%. In some instances, the thickness of the lens may be between about 0.5 mm and about 10 mm, between about 1 mm and about 8 mm, between about 1 mm and about 5 mm, between about 2 mm and about 4 mm, about 0.5 mm, about 1 mm, about 1.5 mm, about 2 mm, about 2.5 mm, about 3 mm, about 3.5 mm, about 4 mm, about 4.5 mm, about 5 mm, about 5.5 mm, or about 6 mm. In some variations of light assemblies comprising a lens, the lens may be fixedly attached to the light assembly. In other variations, the lens may be removably attached to the light assembly, which may allow the lens to be exchanged to achieve different amounts of light attenuation.

Germicidal Light Source

The germicidal light source 106 may be located within a housing 104, and may be a light source configured for germicidal irradiation. In some variations, the germicidal light source 106 may emit light in the UVC wavelength band. The germicidal light source may emit light in a spectrum between about 100 nm and about 280 nm. For example, the germicidal light source may be configured to have a wavelength band centered between about 240 nm and about 260 nm, between about 250 nm and about 260 nm, or at about 254 nm. However, it should be appreciated by those skilled in the art that the germicidal light source 106 may be configured to emit light at other suitable wavelengths.

The germicidal light source 106 may be any suitable type of light source, and may have any suitable specifications. In one variation, the germicidal light source is a cold cathode fluorescent lamp (CCFL). The germicidal light source 106 may have any suitable wattage. For example, the germicidal light source 106 may have a wattage between about 0.1 W and about 5 W, or between about 0.5 W and about 1.5 W. As other examples, the germicidal light source 106 may have a wattage greater than about 5 W, may have a wattage of about 0.5 W, may have a wattage of about 1 W, may have a wattage of about 1.5 W, may have a wattage of about 2 W, may have a wattage of about 3 W, may have a wattage of about 4 W, may have a wattage of about 5 W, or may have other suitable wattages. The germicidal light source 106 may have any suitable striking voltage. For example, the striking voltage may be between about 50 $V_{rms}$ and about 1000 $V_{rms}$, between about 200 $V_{rms}$ and about 800 $V_{rms}$, between about 500 $V_{rms}$ and about 700 $V_{rms}$, about 500 $V_{rms}$, about 550 $V_{rms}$, about 600 $V_{rms}$, about 650 $V_{rms}$, about 700 $V_{rms}$, about 750 $V_{rms}$, or about 800 $V_{rms}$. The germicidal light source 106 may have any suitable operating voltage. For example, the operating voltage may be between about 50 $V_{rms}$ and about 500 $V_{rms}$, between about 100 $V_{rms}$ and about 300 $V_{rms}$, about 100 $V_{rms}$, about 150 $V_{rms}$, about 200 $V_{rms}$, about 250$_{rms}$, or about 300 $V_{rms}$. The germicidal light source 106 may have any suitable operating current. For example, the operating current may be about 5±3 $mA_{rms}$. In some of variations, the operating current may be about 5±1 $mA_{rms}$.

In one particular variation, the germicidal light source 106 may comprise a cold cathode fluorescent lamp (CCFL) having a striking voltage of about 650 $V_{rms}$, an operating voltage of about 200 $V_{rms}$, an operating current of about 5±1 $mA_{rms}$, and a wattage of about 1 W.

In some variations, the light assembly may be configured such that the germicidal light source can be exchanged. For example, a first germicidal light source may be removed from the housing, and a second germicidal light source having a lesser or greater luminance may be inserted. This may be desirable, for example, to reconfigure a germicidal light source for use with a second contact surface that is at a different distance from the germicidal light source than a first contact surface, or to reconfigure a germicidal light source for use with different operational parameters (e.g., shorter or longer disinfection cycles). The germicidal light source may additionally or alternatively be configured such that the luminance of the germicidal light source may be electronically adjustable.

Generally, it may be desirable that the germicidal light source 106 emit a minimum amount of light to adequately sterilize a desired surface over one or more disinfection cycles and/or periodic disinfection cycles (described in more detail herein). Using a germicidal light source having an intensity at or near the minimum effective intensity at the contact surface may minimize risk associated with use of the system. Risks that may be minimized include human exposure during operation, such as due to reflection off of a surface or due to malfunctioning of the sensing and disabling features described herein. Lights having low luminance may be less likely to reflect off a surface (e.g., a surface of a human interface device being disinfected) than lights having higher luminance.

In some variations, it may be desirable that the intensity of the germicidal light source at the contact surface's farthest point from the germicidal light source be between about 1 $\mu W/cm^2$ and about 3000 $\mu W/cm^2$, between about 1 $\mu W/cm^2$ and about 200 $\mu W/cm^2$, between about 100 $\mu W/cm^2$ and about 1000 $\mu W/cm^2$, between about 1 $\mu W/cm^2$ and about 100 $\mu W/cm^2$, between about 10 $\mu W/cm^2$ and about 15 $\mu W/cm^2$, between about 30 $\mu W/cm^2$ and about 50 $\mu W/cm^2$, between about 10 $\mu W/cm^2$ and about 150 $\mu W/cm^2$, less than about 3000 $\mu W/cm^2$, less than about 2000 $\mu W/cm^2$, less than about 1000 $\mu W/cm^2$, less than about 500 $\mu W/cm^2$, less than about 400 $\mu W/cm^2$, less than about 300 $\mu W/cm^2$, less than about 200 $\mu W/cm^2$, less than about 100 $\mu W/cm^2$, less than about 80 $\mu W/cm^2$, less than about 60 $\mu W/cm^2$, less than about 40 $\mu W/cm^2$, or less than about 20 $\mu W/cm^2$.

In one example, the germicidal light source may have a luminance such that the intensity of light having a central wavelength (e.g., about 254 nm) at given distances are of the magnitudes listed in Table 1 below:

TABLE 1

Intensity of Germicidal Light Source

| Distance from center of germicidal light source (inches) (approximate) | Intensity ($\mu W/cm^2$) (approximate) |
| --- | --- |
| 1 | 2260 |
| 2 | 900 |
| 3 | 460 |
| 4 | 280 |
| 5 | 180 |
| 6 | 140 |
| 7 | 100 |
| 8 | 80 |
| 9 | 60 |
| 10 | 50 |
| 11 | 40 |
| 12 | 30 |
| 13 | 28 |
| 14 | 24 |
| 15 | 20 |
| 16 | 18 |
| 17 | 16 |
| 18 | 14 |
| 19 | 12 |
| 20 | 11 |
| 21 | 9 |
| 22 | 8 |
| 23 | 7 |
| 24 | 6 |
| 25 | 6 |
| 26 | 5 |
| 27 | 5 |
| 28 | 4 |
| 29 | 4 |
| 30 | 3 |

In some variations, the germicidal light source may have an intensity (e.g., an intensity at a central wavelength, such as a central wavelength as described herein) at 10 inches from the center of the germicidal light source of less than about 500 $\mu W/cm^2$, less than about 400 $\mu W/cm^2$, less than about 300 $\mu W/cm^2$, less than about 200 $\mu W/cm^2$, less than about 100 $\mu W/cm^2$, less than about 80 $\mu W/cm^2$, less than about 60 $\mu W/cm^2$, less than about 40 $\mu W/cm^2$, or less than about 20 $\mu W/cm^2$. In some variations, the germicidal light source may have an intensity (e.g., an intensity at a central wavelength, such as a central wavelength as described herein) at 5 inches from the center of the germicidal light source of less than about 500 $\mu W/cm^2$, less than about 400 $\mu W/cm^2$, less than about 300 $\mu W/cm^2$, less than about 200 $\mu W/cm^2$, less than about 100 $\mu W/cm^2$, less than about 80 $\mu W/cm^2$, less than about 60 $\mu W/cm^2$, less than about 40 $\mu W/cm^2$, or less than about 20 $\mu W/cm^2$. In some variations, the germicidal light source may have an intensity (e.g., an intensity at a central wavelength, such as a central wavelength as described herein) at 15 inches from the center of the germicidal light source of less than about 500 $\mu W/cm^2$, less than about 400 $\mu W/cm^2$, less than about 300 $\mu W/cm^2$, less than about 200 $\mu W/cm^2$, less than about 100 $\mu W/cm^2$, less than about 80 $\mu W/cm^2$, less than about 60 $\mu W/cm^2$, less than about 40 $\mu W/cm^2$, or less than about 20 $\mu W/cm^2$.

The desired luminosity of the germicidal light source in a particular variation of the germicidal devices described herein may depend on a number of factors, including but not limited to the distance between the germicidal light source and the contact surface, the desired disinfecting cycle duration and/or periodic disinfection cycle duration, and environmental factors (e.g., the existence of a particular pathogen). For instance, in situations in which the germicidal light source is located further from the contact surface, the desired intensity may be higher and/or the exposure time may be longer than in situations in which the germicidal light source is located closer to the target area. Similarly, the desired luminance of the germicidal light source may be lower for longer exposure times (e.g., longer disinfection cycle lengths and/or longer periodic cycle lengths), while the desired luminance of the germicidal light source may be higher for shorter exposure times (e.g., shorter disinfection cycle lengths and/or shorter periodic cycle lengths). The exposure time may be increased by increasing the length of individual disinfection cycles or periodic disinfecting cycles, or additionally or alternatively, by having an increased number of cycles (e.g., by decreasing the periodic interval between periodic disinfecting cycles), whose disinfection effects are cumulative, as is described in more detail herein.

The germicidal light source may be turned on and off by a controller system, as is described in more detail herein. Additionally or alternatively, the germicidal device may comprise one or more manual override buttons or switches configured to control the germicidal light source. For example, an override button may be an on button (i.e., a button that turns on the disinfecting light source). As another example, an override button may be an off button (i.e., a button that turns off the germicidal light source). In variations in which the germicidal device is connected to an associated human interface device having software configured to control the germicidal device, there may be one or more override commands configured to control the germicidal light source (e.g., using the user interface of the software, a particular input via a peripheral device (e.g., a key on a keyboard), or the like).

Proximity Sensor

The one or more sensors 108 of the germicidal device 100 may comprise a proximity sensor. The proximity sensor may be configured to detect when an object (e.g., a person) is near the germicidal light source. That is, the proximity sensor may be configured to provide information regarding whether a user is within an area receiving light from the germicidal light source when the germicidal light source is lit. In some variations, the sensor may monitor an area larger than the area receiving light from the germicidal light source, which may reduce the risk of inadvertent exposure.

In some variations, the proximity sensor may be a motion sensor. For example, the proximity sensor may be an active infrared sensor, a passive infrared sensor, a temperature sensor, an imager, the like, or a combination thereof. In the variation shown in FIG. 1A, the proximity sensor 108 may comprise a passive infrared sensor. In other variations, the proximity sensor may be configured to detect when at least a portion of an object (e.g., a person) is within the monitored area, but is substantially motionless (e.g., a user's hands are on a keyboard within the monitored area, but not typing). For example, the proximity sensor may comprise one or more infrared transmitters that correspond to one or more infrared receivers, such that a detection event is registered if substantially all of the infrared light transmitted is not received by the one or more infrared receivers.

Distance Sensor

The light assembly may optionally comprise a distance sensor. In variations comprising a distance sensor, the distance sensor may be used to determine a distance between the germicidal light source and the contact surface. The determined distance may then be used to determine an appropriate luminance in order to achieve a desired intensity of light from the germicidal light source at the contact surface, and/or other appropriate operational parameters (e.g., an appropriate disinfection cycle or periodic disinfection cycle duration) in order to achieve a desired germicidal effect. In some of these variations, the luminance of the germicidal light source may be electronically adjustable in response to the distance determination. However, in variations that do not include a distance sensor, settings based on preset values using expected operating conditions or settings from user input may be utilized.

Alignment Light Source

The light assembly may optionally comprise an alignment light source that may be configured to project a visible illumination pattern that may indicate the area illuminated by the germicidal light source. This may help align the germicidal device with the contact surface intended to be disinfected. In some of these variations, the alignment light source may be configured to illuminate an area matching the area illuminated by the germicidal light source. In other variations, the alignment light source may be configured to generate one or more linear illumination markers indicating the area illuminated by the germicidal light source. For example, the alignment light source may comprise a LASER or any other suitable type of light source that may be configured to illuminate a line that is approximately parallel to an edge (e.g., a front edge) of the area illuminated by the germicidal light source. An alignment light source may be placed on an underside of the housing, or may be at least partially enclosed in the housing.

In some variations of the germicidal device comprising an alignment light source, when the germicidal device is initially connected to a power source, the alignment light source may generate an alignment illumination pattern that may identify to the user the anticipated illumination area of the germicidal light source, so that the germicidal light source may be directed towards a desired contact surface. For instance, the alignment light source may be activated for a period of time (e.g., approximately 30 seconds) when the germicidal system is initially powered on. Additionally or alternatively, the alignment light source may be activated each time the germicidal light source is turned on, and/or the alignment light source may be activated via user control (e.g., via software or via a manual switch).

In some variations of the germicidal device comprising both a distance sensor and an alignment light source, the distance sensor and alignment light source may be configured to function together. For example, if the alignment light source is illuminated for an initial period of time after the germicidal device is connected to a power source, after this time period has elapsed, the distance sensor may then be activated to determine a distance between the germicidal light source and the contact surface.

Work Lights

Returning to FIG. 1A, the light assembly 102 may further comprise one or more work lights 110 for illuminating the contact surface. This may be desirable in dark or dimly lit environments. In the variation shown in FIG. 1A, there may be two work lights 110 disposed on an underside of the housing 104, or at least partially enclosed therein, with one adjacent to each end of the recess 116. In other variations, there may be one, three, four, or more work lights. The operational parameters of the work lights may be adjusted to provide desired illumination (e.g., to facilitate the visibility of a human interface device (e.g., keyboard), to facilitate the performance of a task (e.g., reading) near the contact surface). The work lights may in some variations be automated, while in other variations may be user controlled, as described in more detail herein.

Indicator Lights

As shown in FIG. 1C, the light assembly 102 may comprise one or more indicators 120. In some instances the one or more indicators 120 may comprise an indicator light, which may be configured to emit light that conveys information about the status of the system. When an indicator 120 comprises an indicator light, the indicator light may comprise one or a plurality of multi-colored LEDs, single-colored LEDs, incandescent light sources with or without lenses configured to affect a color of light output, the like, or a combination thereof. The indicator lights may have one or a plurality of colors (e.g., green, yellow, red, blue). As one example, the indicator light may comprise a three-color LED. In other variations the indicator 120 may comprise a display screen.

The indicator 120 may be at least partially enclosed in the housing 104 of the light assembly 102, or it may be located fully outside of the housing. When the indicator 120 comprises an indicator light, the indicator light may in some cases be located within the housing 104 behind a translucent portion of the housing, such that it may be seen from the outside of the housing. In some variations, the indicator may be incorporated into a portion of a logo.

The indicator 120 may convey information. For example, the indicator 120 may convey whether the germicidal light source is lit, a status of the contact surface (e.g., contaminated, disinfected), an operating parameter of the system, user input, connectivity status with a network, the like, or a combination thereof. As another example, in some variations the indicator 120 may act as a progress display bar to give visual feedback regarding current status in various timed modes (e.g., by comprising a plurality of LEDs configured to illustrate the passage of a time period, such as the period elapsed in a disinfection cycle). In variations of germicidal devices comprising controls (e.g., buttons), the indicator 120 may indicate user input, such as use of a selector button configured to toggle through available options.

By way of explanation and not limitation, in one variation, an illuminated green LED may indicate that the contact surface is disinfected; an illuminated yellow LED may indicate that the contact surface is contaminated, and an illuminated red LED may indicate that the germicidal light source is lit. In another variation, an illuminated red LED may indicate detection of human interaction (e.g., detected by an interaction sensor as described herein) to indicate that the contact surface has been contacted. An illuminated blue LED may indicate that the germicidal light source is lit. An illuminated green LED may indicate that the contact surface has been disinfected.

Although the features are described above primarily with respect to the variation of germicidal device shown in FIGS. 1A-1C, it should be appreciated that the germicidal devices described herein may have other configurations, which may have some or all of the components described above. For example, another variation of a germicidal device is shown in FIGS. 8A-8H. As seen in detail in FIGS. 8A and 8B, the germicidal device 800 may comprise a housing 806 defining an aperture, and an adjustable mount 810. The adjustable mount 810 may extend from the housing 806 and be configured to removably hold the germicidal device 800 in place relative to a contact surface. The germicidal device 800 may comprise a germicidal light source 812 (e.g., a UV light source) that may be at least partially enclosed within the housing 806. The germicidal light source 812 may be configured to project an illumination pattern at least partially defined by the aperture and the position of the adjustable mount 810, such that the illumination pattern may substantially correspond to a contact surface to be disinfected (e.g., a portion of a human interface device). The germicidal device 800 may comprise one or more sensors, wherein the one or more sensors may be configured to detect an object proximate to the housing and/or an interaction with the human interface device. The germicidal device 800 may optionally comprise one or more user controls, such as a toggle button 823, which may, for example, allow a user to control one or more operational parameters (e.g., toggle between different delay period settings); and may optionally comprise one or more indicator lights 822. The indicator lights 822 may convey information to the user, such as the information described above with respect to indicator 120 of germicidal device 100. The germicidal device 800 may be connected to a power source and/or a human interface device via any suitable connection, such as a USB port 824.

Exemplary Components

Figure 11:
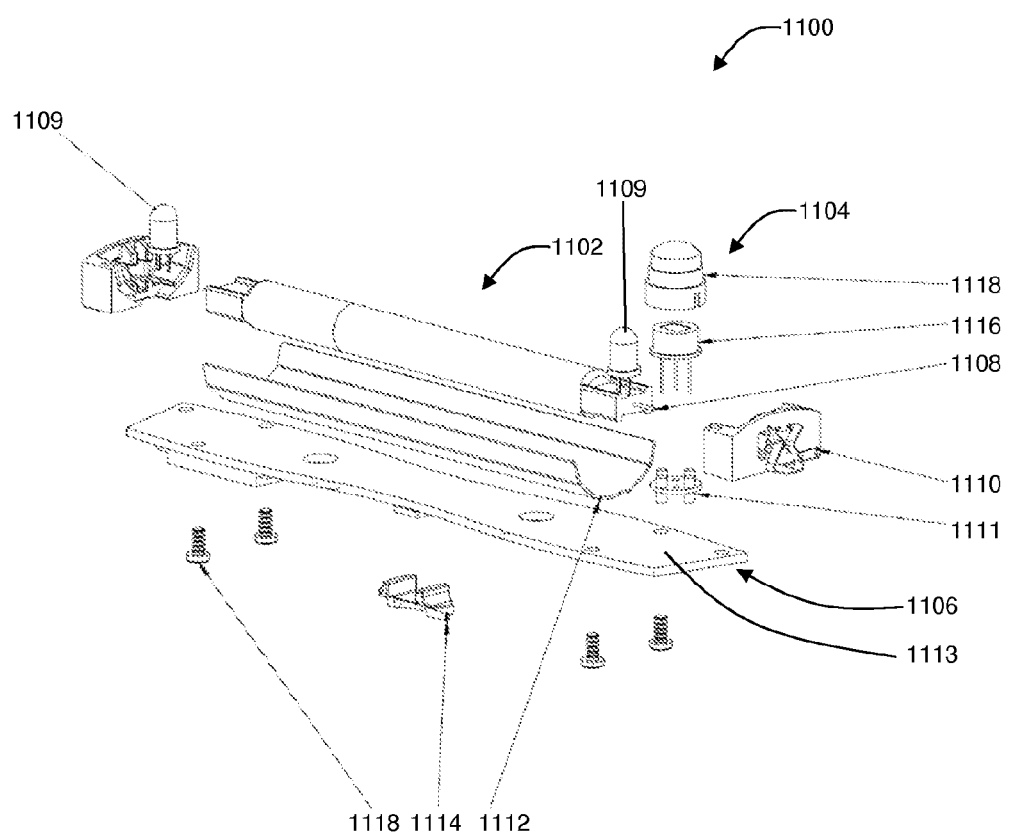
FIG. 11 is an exploded view of an exemplary germicidal device without its external housing.

Turning now to FIG. 11, shown there is an exploded view of a variation of a germicidal device (which may be similar to germicidal device 100) without its external housing. As depicted there, the germicidal device 1100 may comprise a germicidal light assembly 1102, proximity sensor assembly 1104, an indicator light (not shown) that emits light through light pipe 1114, and a controller system 1106. Optionally, the device 1100 may comprise one or more work lights 1109. The germicidal light assembly 1102 may comprise a cold cathode fluorescent lamp (CCFL) 1108, a bulb contact assembly 1110, and a light reflector 1112. The proximity sensor assembly 1104 may comprise a passive infrared (PR) sensor 1116 and a Fresnel lens 1118 disposed over the PIR sensor. The proximity sensor assembly 1104 may optionally comprise a PIR sensor spacer 1111 to help secure and position the PIR sensor 1116. The controller system 1106 may be in communication with the germicidal light assembly, proximity sensor assembly, and any work lights, as further explained and depicted in FIG. 13. The controller system 1106 may comprise a printed circuit board (PCB) substrate 1113 upon which a microprocessor or controller is mounted, along with the electrical connections to the light assembly and the proximity sensor assembly, as well as the electrical components that support those connections (not shown here but explained and depicted below in FIG. 13). The controller system 1006, disinfecting light assembly 1102, and proximity sensor assembly 1104 may be mechanically coupled together using any suitable means, such as screws 1118.

Figure 12A:
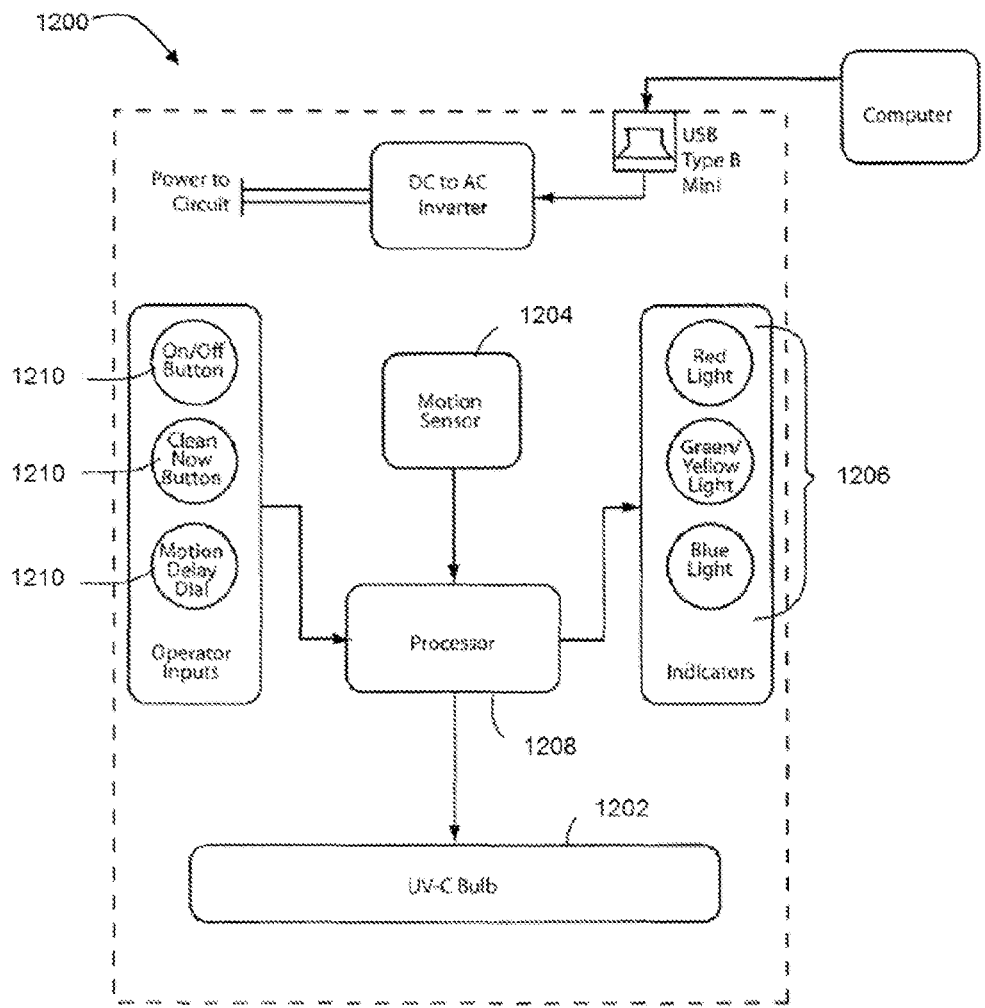
FIG. 12A is a block diagram representation of the components and modules that support one variation of a germicidal device.

FIG. 12A is a block diagram representation of the components and modules that support one variation of a germicidal device (which may be similar to germicidal device 100 and/or germicidal device 1100 and/or any of the germicidal devices described herein). The germicidal device 1200 may be attachable to a computer (or any of the human interface devices described herein) via a USB port. The germicidal device 1200 may comprise a processor/controller 1208, a germicidal light assembly 1202 connected to the controller 1208, a motion sensor module 1204 connected to the controller 1208, an indicator 1206, and one or more user input elements 1210. The indicator 1206 may comprise one or more indicator lights, such as three LEDs having three different colors (e.g., red, green or yellow, blue) that may notify the user of the status of the germicidal device 1200 (e.g., whether it is on or off, its disinfection status, such as whether it is currently disinfecting or about to commence the disinfecting process, etc.). The controller 1208 is programmed to drive the disinfecting light assembly 1202 as described elsewhere herein. The inputs to the controller 1208 may comprise user inputs 1210. These user inputs may be commands that include powering the germicidal device 1200 on or off, initiating a disinfection process immediately, or setting a delay time for starting a disinfection process (e.g., the duration of the time interval after a detection event before disinfection starts). These inputs may comprise buttons, dials, switches, and/or may use touch-screen technology. The proximity sensor 1204 also provides an input to the controller 1208, relaying data regarding the presence or absence of an object (e.g. a person's hands or fingers) within the sensor's field of view. Some proximity sensors may also relay data to the controller regarding detected motion in its scan region.

Figure 12B:
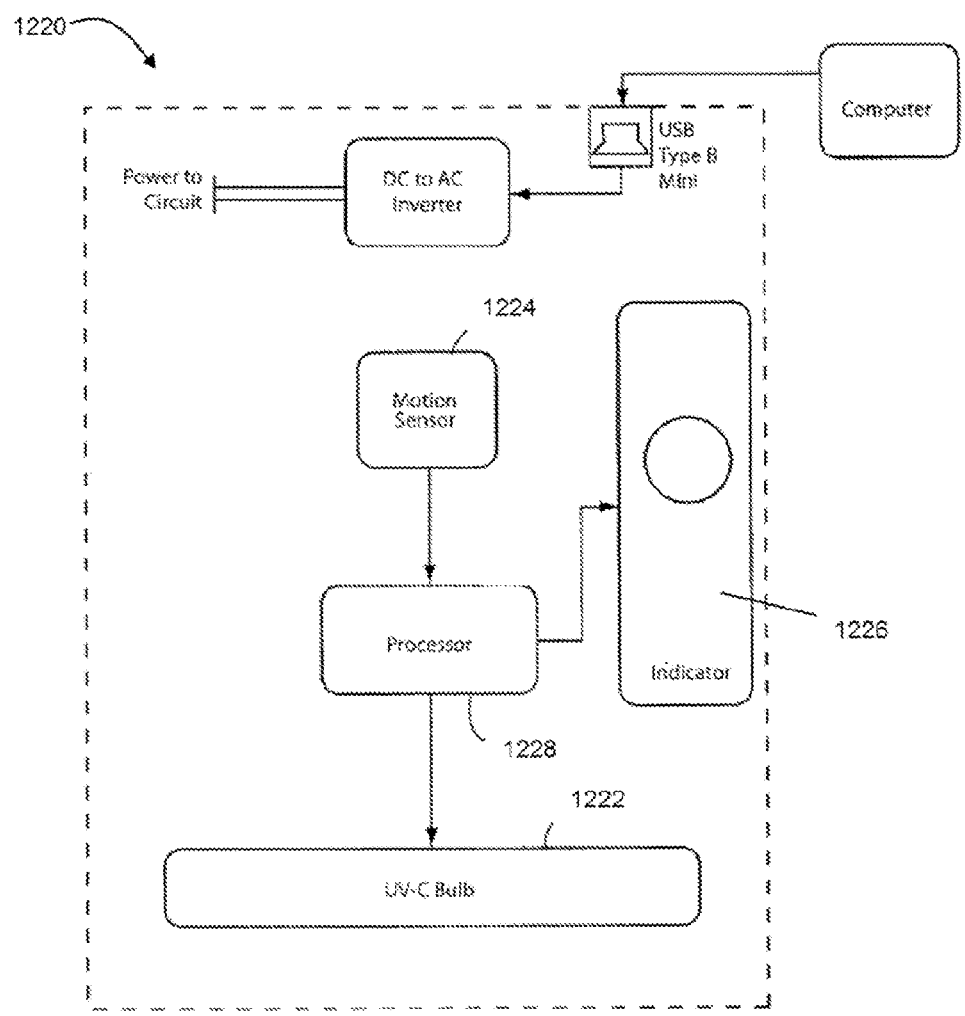
FIG. 12B is a block diagram of another variation of a germicidal device.

FIG. 12B is a block diagram of another variation of a germicidal device 1220 that is similar to the germicidal device 1200 of FIG. 12A (and may also be similar to germicidal device 100 and/or germicidal device 1100). As depicted there, germicidal device 1220 may comprise a processor/controller 1228, a disinfecting light assembly 1222 connected to the controller 1228, a motion sensor module 1224 connected to the controller 1228, and an indicator 1226. The germicidal device 1220 may be similar to the device 1200, but does not have any user input elements and the indicator 1226 comprises a single light element that is configured to emit multiple wavelengths of light (e.g., red, green, blue). The light element may comprise multiple LEDs that are packaged together, with each of the LEDs configured to emit different wavelengths. Additional description of the circuitry that supports the functionality of the germicidal devices depicted in FIGS. 12A-12B (as well as the germicidal devices described elsewhere) is provided below.

Figure 13:
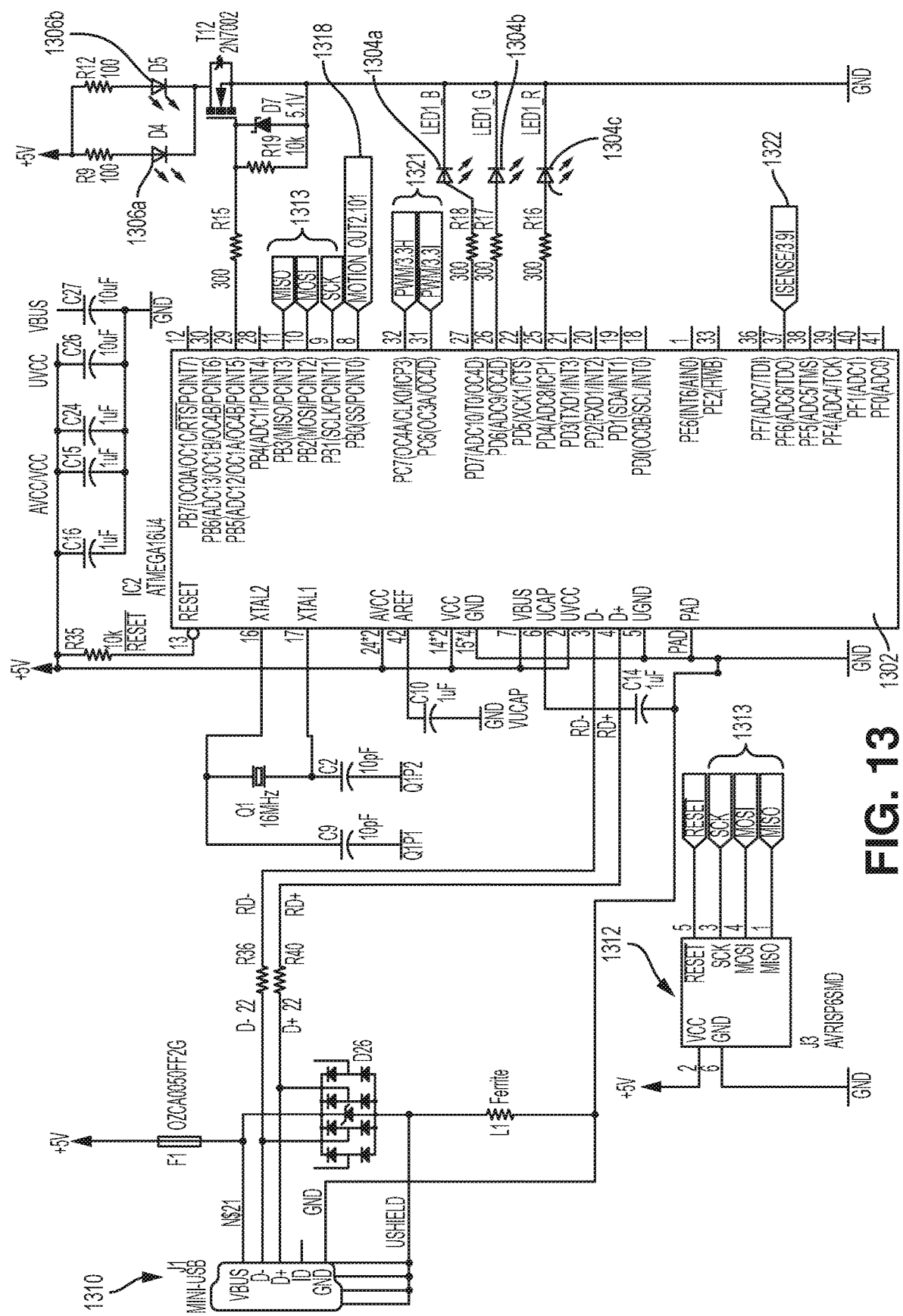
FIG. 13 is a circuit schematic of one variation of a germicidal device.
Figure 14:
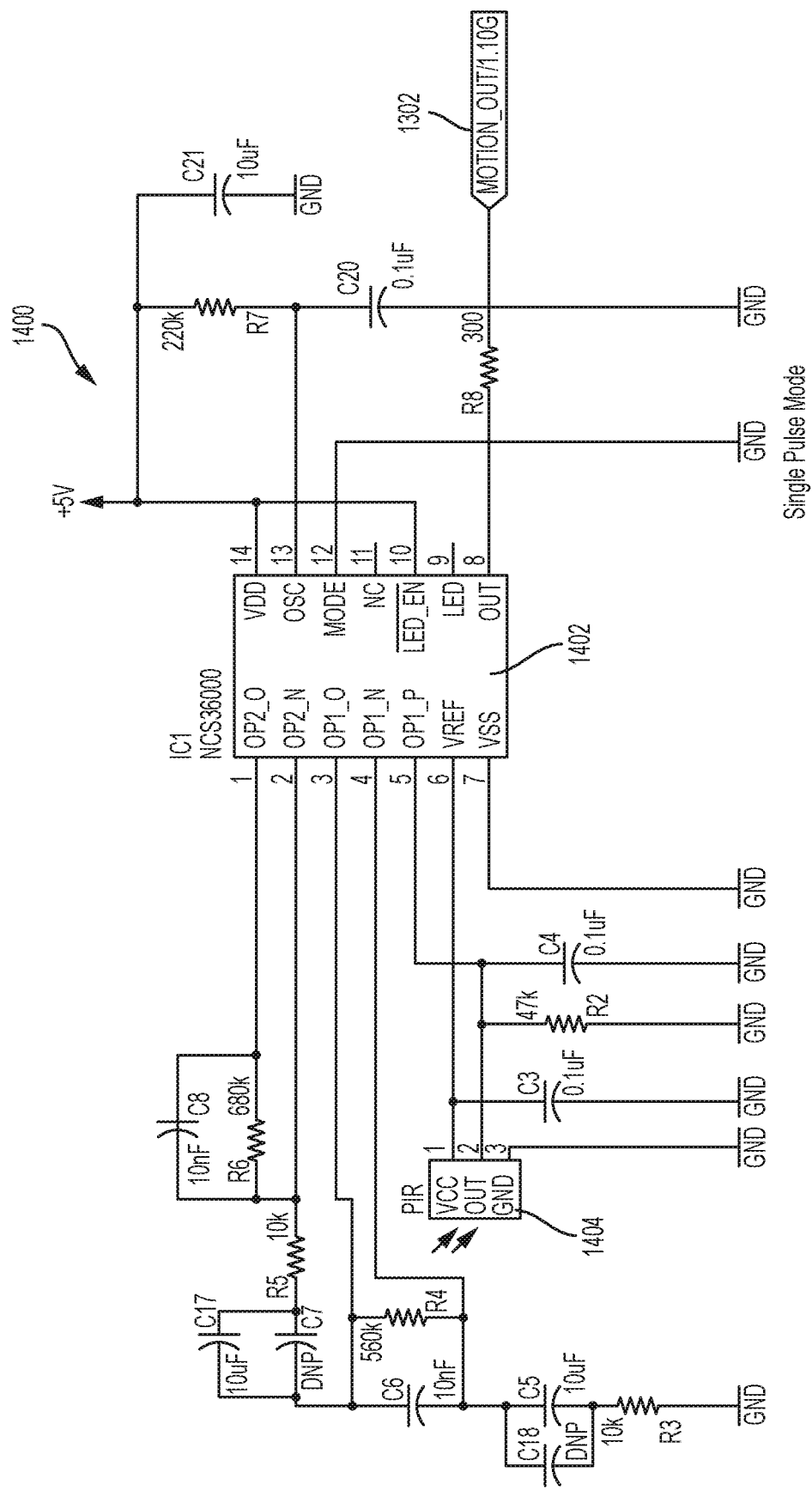
FIG. 14 depicts one variation of the circuitry of the proximity sensor assembly.
Figure 15:
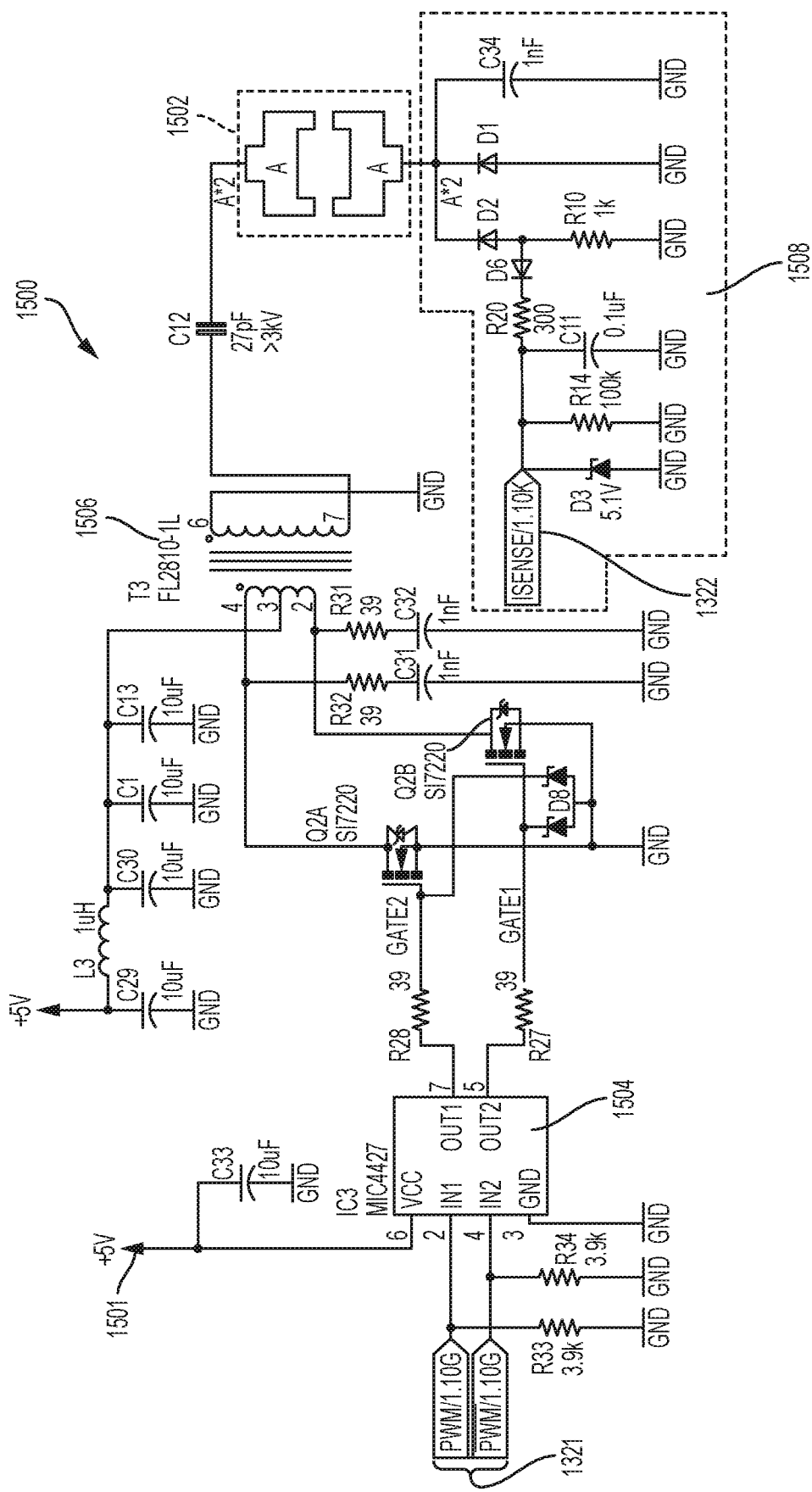
FIG. 15 depicts one variation of circuitry of an DC-to-AC inverter assembly that drives an exemplary the germicidal light source.

FIGS. 13-15 are circuit schematics of one variation of a germicidal device. The circuit components depicted in FIGS. 13-15 and/or their electrical ports/contacts may be mounted on a PCB substrate, such as the PCB substrate 1113 depicted in FIG. 11. FIG. 13 is a circuit diagram that depicts the connectivity between a microcontroller 1302, indicators 1304*a,b,c* comprising LEDs, work lights 1306*a,b* comprising LEDs, and a USB port 1310 (e.g., a mini-USB port). Also depicted in FIG. 13 is the electrical interface 1318 to the proximity sensor assembly (the details of which are depicted in FIG. 14) and the electrical interface 1321 to the DC-to-AC inverter assembly that drive the germicidal light source (the details of which are depicted in FIG. 15). It should be appreciated that the indicators may be any suitable light source, and are not limited to LEDs. The microcontroller 1302 may have one or more programs stored in its memory, where the programs are configured to execute the functions of the germicidal device, as described throughout this specification. For example, the microcontroller 1302 may be programmed to activate the work LEDs 1306*a,b* according to user-issued commands via software (described in more detail herein) and to activate the indicators 1304*a,b,c* to indicate the operational mode and/or state of the device (e.g., germicidal light on, disinfected). Power to the germicidal device may be provided via the USB port 1310, and/or a battery.

In some variations, a germicidal device may comprise one or more programming interfaces. For example, a germicidal device may comprise a first programming interface that is accessible only when the housing of the germicidal device is removed and a second programming interface that is accessible via a port on the housing. The first programming interface may be used during manufacturing to program the microcontroller with the basic functions of the germicidal device, and the second programming interface may be used to program the microcontroller with user preferences and/or operating programs that overlay the basic functions. The second programming interface may be restricted such that the core programs of the microcontroller are not re-programmable by an end user, but may permit the user to load or modify programs regarding disinfection cycle duration and the like. Limiting user-accessibility to the first programming interface may help to prevent an end-user from deleting or corrupting the core programs that drive the basic functions of the germicidal device (e.g., the signal levels and timing that drive the indicator light(s), germicidal light, etc.). FIG. 13 depicts one variation of a programming interface 1312 that may be used to program the microcontroller during the device manufacturing process, and does not have an electrical port that is accessible via the housing of the device. The programming interface 1312 may be connected to the microcontroller via ports and connections 1313. The user-accessible programming port may comprise the USB port 1310. The software-implemented user interface may permit the user to select certain modes and preferences for operating the germicidal device, as described in more detail herein.

FIG. 14 depicts one variation of the circuitry of the proximity sensor assembly 1400. The proximity sensor assembly 1400 may comprise a PIR controller 1402 and a PIR sensor 1404. The output of the proximity sensor assembly 1400 from the PIR controller 1402 drives the electrical interface 1318 to the germicidal device microcontroller 1302. The output of the proximity sensor assembly 1400 provides data regarding whether an object is within the field-of-view of the PIR sensor 1404.

FIG. 15 depicts one variation of the circuitry of the DC-to-AC inverter assembly 1500 that drives the germicidal light source 1502. Many germicidal light sources, such as CCFLs, use AC power, and such an inverter assembly may be used to convert the board level DC power supply to AC power for the CCFL. As depicted in FIGS. 13 and 15, the device microcontroller 1302 provides power-on commands to the DC-to-AC inverter assembly 1500 via electrical interface 1321. The command signals from the interface 1321 activate a buffer or driver 1504, which may then supply DC power 1501 (board power) to the transfomer 1506, which converts the DC power to AC power, thereby powering the germicidal light source 1502. Optionally, the DC-to-AC inverter assembly 1500 may also comprise current sensor circuitry 1508 that provides a feedback signal to the device microcontroller 1302 via interface 1322. The current sensor circuitry 1508 detects the electrical current across the light source 1502, which is directly correlated to whether the germicidal light source is lit or not. If the current data is not consistent with what the microcontroller is expecting (i.e., the microcontroller has sent a command to activate the light source, but the current data indicates that the light source is not lit, or the light source should not be lit, but the current data indicates that the light source is lit), then an error message may be generated and presented to the user (e.g., to check the bulb, check the connections on the device, submit a service request, etc.).

Although FIGS. 13-15 depict circuitry with specific connections between the electrical components, it should be understood that these particular electrical connections and circuits may vary depending on the electrical requirements of the germicidal light source, the available voltage supply (e.g., 5 V, 3.3 V, 1.8 V, etc.), desired operating speed, PCB sizing and layering, noise sources, and selected microcontroller IC chips, etc. For example, the filtering and amplification circuits depicted in FIGS. 13-15 may vary depending on the tolerance of a selected microcontroller to noise.

Mounting Assembly

The light assemblies described herein may be mounted relative to a contact surface via one or more mounting assemblies. The light assemblies may be attached to any number of suitable human interface devices, such as but not limited to a touchscreen display, a credit card payment device, a grocery store self-checkout aisle interface, a point-of-sale device, a cash register, a keyboard or a mouse, a laptop, or the like. The light assemblies described herein may also be mounted on a stand, which may hold the light assembly near a contact surface to be disinfected.

The germicidal device 100 shown in FIGS. 1A-1C comprises one variation of a mount 112. As shown in more detail in FIGS. 2A-2C, the mount 112 may comprise support member 122 and support member 124, which may be connected to the rear of the housing 104. The support members 122, 124 may be substantially flat and may extend to connect with an engagement member 126 that may be configured to engage and/or mate with a receptacle housing. The support members 122, 124 may form a gap and/or space between them. This gap may create an attractive appearance and/or may reduce the overall weight of the mount 112.

The engagement member 126 may include a top edge 128 that may connect with the support members 122, 124. The engagement member 126 may include an upper section 130 that may extend into a tapered body portion 132. The tapered body portion 132 may extend substantially orthogonally from the support members 122, 124. At the second end of the engagement member 126, the tapered body portion 132 may include a lower edge 134 that may be smaller in size than the top edge 128. Although shown with rounded corners, the lower edge 134 may also have square corners depending on the locking mechanism. At one side of the engagement member 126, a notched section 136 may be positioned substantially midway between the top edge 128 and lower edge 134. Although shown as a rounded semicircular notch, the notched section 136 may take the form of other shapes or appearances depending on the locking mechanism.

As seen in FIGS. 2A-2C, the germicidal device 100 may comprise a receptacle housing 138 that may be sized and shaped to accept the engagement member 126 into an opening 140 at the top portion of the receptacle housing. When the engagement member 126 is positioned within the receptacle housing 138, the lower edge 134 of the engagement member may extend into the receptacle housing to the lower edge 142 of the receptacle housing. The size and shape of the engagement member 126 may substantially match the internal size and configuration of the receptacle housing 138. In order to prevent the engagement member 126 from being retracted from the receptacle housing 138, the notched section 136 may align with a latch 144 positioned on one side of the receptacle housing. The latch 144 may be movable and adjustable so that a protuberance 146 on one side of the latch may make mating contact with the notched section 136 while the engagement member 126 is within the receptacle housing 138. As shown in FIGS. 2B-2C, the latch 144 may rotate about point 148 between an open position (FIG. 2B) and a closed position (FIG. 2C). When in the closed position, the protuberance 146 may mate and/or engage within the notched section 136 so as to hold the engagement member 126 into a fixed position. The protuberance 146 may frictionally engage in the notched section 136 for preventing the engagement member 126 from being retracted from the open portion 140 of the receptacle housing 138.

An outer surface of the receptacle housing 138 may include a fastener, such as but not limited to an adhesive tape, hook and loop fastener, or the like, that may enable the receptacle housing 138 to stick, adhere, and/or be mechanically fastened to another surface in order to be held in a fixed position when mounted to a surface, such as an outside housing of a laptop. In this way, the light assembly 102 may be reversibly attachable to another surface. When the light assembly 102 is attached to the receptacle housing 138, it may be removed from the receptacle housing by rotating the latch 144 from the closed position to the open position, which may allow the engagement member 138 of the mount 112 to be removed from the receptacle housing 138.

Laptop Mount

Figure 3A:
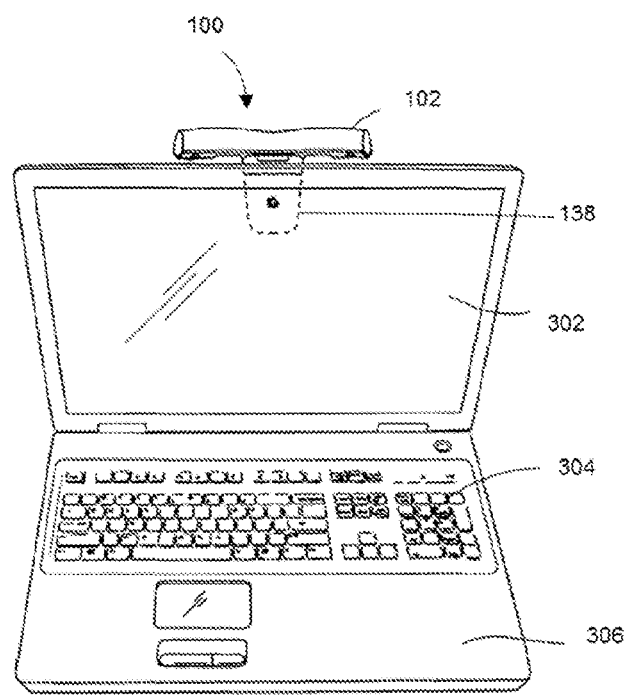
FIG. 3A depicts the germicidal device and mounting assembly of FIGS. 2A-2C attached to a laptop computer.

FIG. 3A is a front elevational view illustrating the germicidal device 100 attached to a laptop computer for use in disinfecting the keyboard of the laptop computer. The germicidal device 100 may be mounted to the outer surface of the laptop computer case behind the liquid crystal display (LCD) 302 via a surface of the receptacle housing 138. As shown, the receptacle housing 138 may be adhered to an outer surface of a personal computer (PC) or tablet for enabling the light assembly 102 to extend over the laptop's LCD onto a keyboard 304 and surface 306.

Figure 3B:
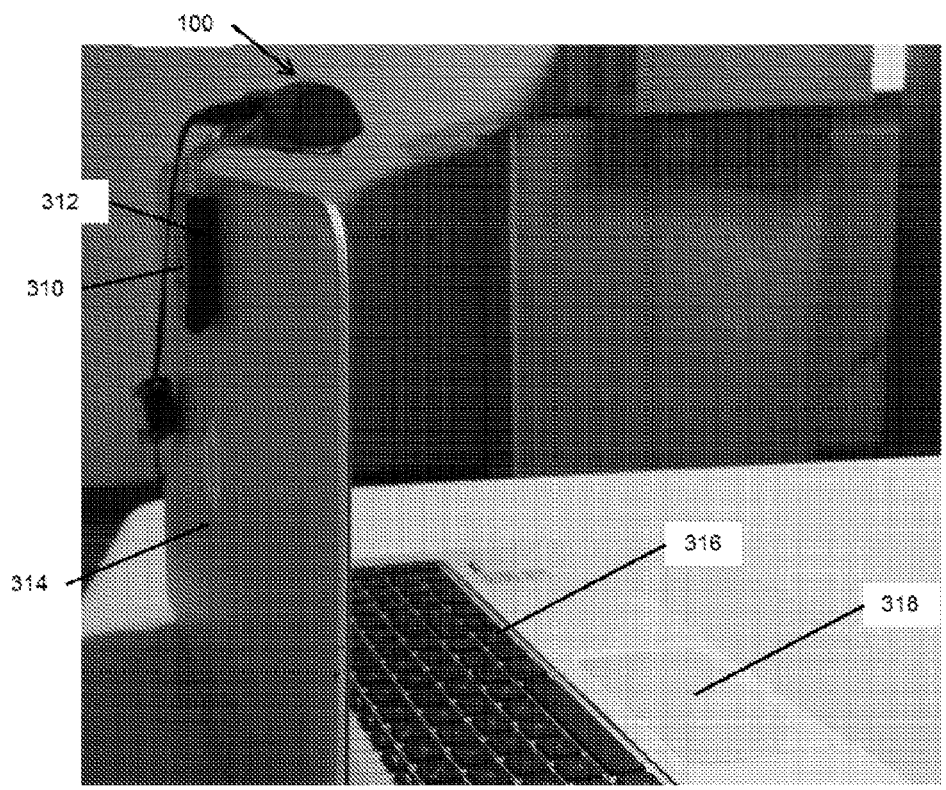
FIGS. 3B-3C show the germicidal device of FIGS. 1A-1C comprising another exemplary mounting assembly.
Figure 3C:
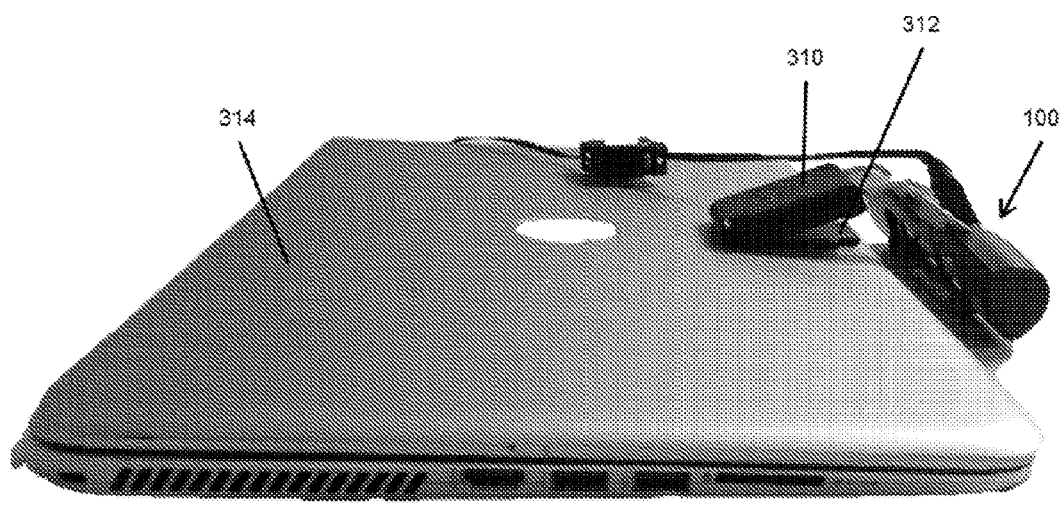

In some instances, it may be desirable that a mounting assembly for use with a laptop be configured to allow the light assembly to flex backwards and facilitate full closure of a laptop computer. FIGS. 3B-3C show one exemplary mounting assembly that is configured to allow the receptacle housing to flex backwards. In the variation shown there, a receptacle housing 310 may be rotatably connected at its distal end to a panel 312. The panel 312 may in turn be configured to be attached to a human interface device. The panel 312 may be configured to be attached to the rear surface of a laptop 314, which may allow the receptacle housing 310, and in turn the germicidal device 100, to flex backwards relative to the laptop 314. FIG. 3B depicts the mounting assembly in a first configuration, in which the receptacle housing 310 is adjacent to the panel 312, such that the germicidal light source of the germicidal device 100 is configured to project onto the contact surface (e.g., keyboard 316 and/or touchpad 318) of the laptop 314. FIG. 3C depicts the mounting assembly in a second configuration, in which the receptacle housing 310 is rotated away from the panel 312. In the second configuration, the front edge of the germicidal device 100 is flush with the bottom of the laptop 314, and the receptacle housing 310 is rotated away from the panel 312. This may allow the laptop 314 to be fully closed with the germicidal device 100 attached while the laptop is on a flat surface. It should be appreciated that the receptacle housing 310 may be rotatable relative to the panel 312 via any suitable means. For example, the receptacle housing 310 and panel 312 may be attached via a pin joint. In some variations, the receptacle housing 310 may be biased toward the panel 312 (e.g., via a torsion spring).

Table Stand

FIGS. 5A-5D and 6A-6E illustrate the germicidal device 100 used in connection with a table stand 500. The table stand 500 may be used, for example, in situations where objects such as tablets, keyboards, mice, or the like may be placed under the germicidal device on a flat surface, such as a table top. The table stand 500 may comprise a mounting shaft 502 having an opening 504 at its top edge. The mounting shaft 502 may connect at a lower end to a surface stand 506. Although the surface stand 506 is shown in a U-shaped configuration, other configurations of the legs (e.g., V-shaped, H-shaped, X-shaped configurations, etc.) are also possible. When in use in a table top environment, the engagement member 126 of germicidal device 100 may be inserted into the opening 504. In some variations, the surface stand 506 may be secured to a surface or other object via an adhesive or other means. For example, the surface stand 506 may be adhered to the bottom of a keyboard via an adhesive connecting the top of the surface stand 506 and the bottom of the keyboard (as shown in FIGS. 6A-6B, discussed in more detail below).

Figure 5A:
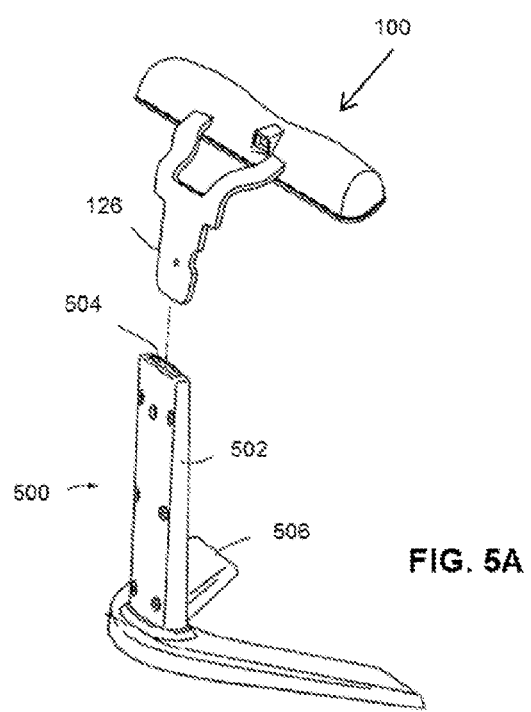
FIGS. 5A, 5B, 5C, and 5D show perspective, front, side, and top views, respectively, of a germicidal device of FIGS. 1A-1C on an exemplary stand.
Figure 5B:
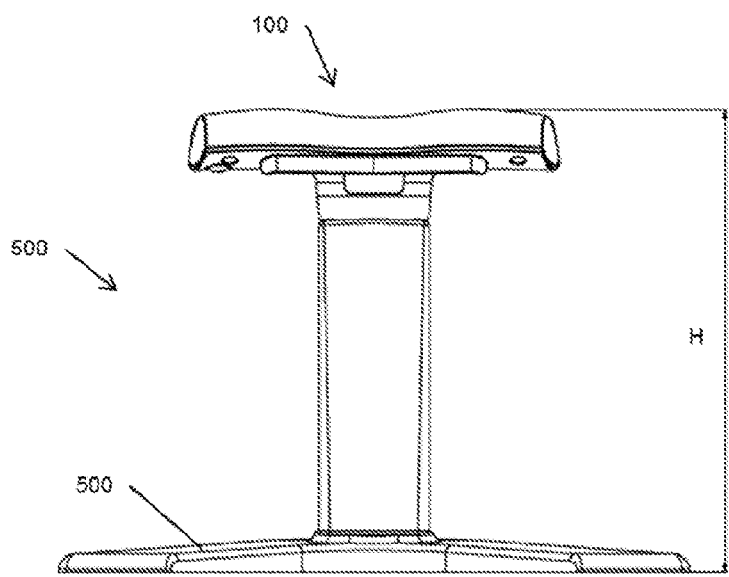
Figure 5C:
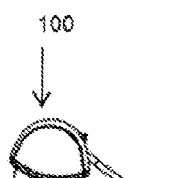
Figure 5D:
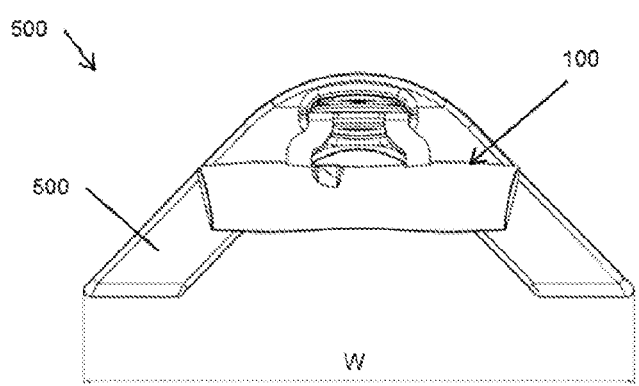

The table stand 500 may have any suitable dimensions. Turning to FIGS. 5B-5D, it may be desirable for the table stand 500 to have a height H such that the disinfecting light of the germicidal device 100 is a desired distance from a contact surface to be disinfected. In some instances, the height H may be between about 5 inches and about 15 inches, about 5 inches and about 10 inches, between about 10 inches and about 15 inches, less than about 5 inches, or more than about 15 inches. More particularly, in some instances the height may be between about 7 inches and about 8 inches. It may be desirable for the dimensions of the surface stand 506 to be such that the table stand 500 is able to provide stable support for the germicidal device 100. In some instances, the depth D may be between about 2 inches and about 10 inches. More particularly, in some instances the width may be about 4 inches. In some instances, the largest width W2 of the surface stand 506 may be between about 5 inches and about 20 inches. More particularly, in some instances the width W2 may be about 10 inches. FIGS. 6A-6E show the resulting disinfection area using the germicidal device 100 with table stand 500, with a keyboard (602) (FIG. 6B) or a mouse (604) (FIGS. 6C-6E). As shown there, when the table stand 500 has a height of about 7.25 inches, the germicidal light source may project light onto an area A having a depth DA from the front of the mounting shaft of the table stand of about 10 inches, and a width WA of about 20 inches.

Mouse Holder

In some instances, the germicidal device may be used with a mounting assembly configured to receive an object comprising a contact surface, such as a surface of a peripheral device of a human interface device. That is, the mounting assembly may be shaped to form a receptacle within which an object can be placed. The germicidal light source may be fixed relative to the receptacle, such that when the object is placed within the receptacle, the contact surface is at a location that is illuminated by a lit germicidal light source.

Figure 4A:
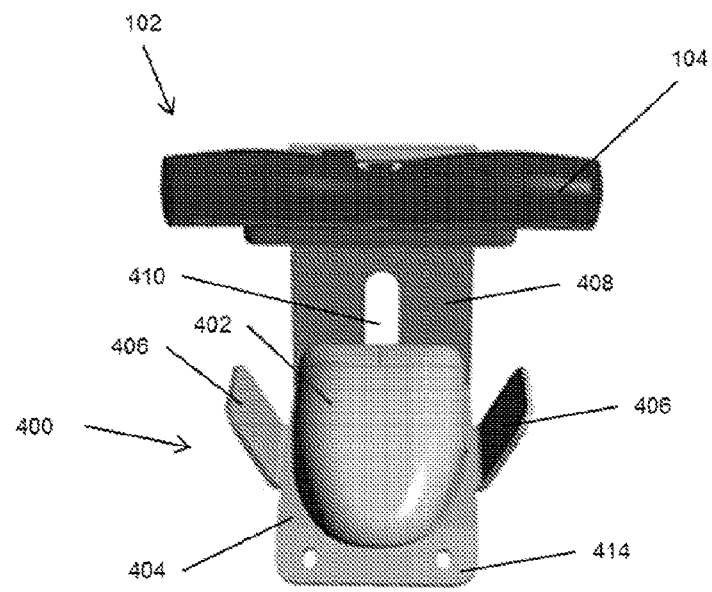
FIGS. 4A and 4B show perspective and side views, respectively, of the germicidal device of FIGS. 1A-1C comprising an exemplary assembly for holding a mouse.
Figure 4B:
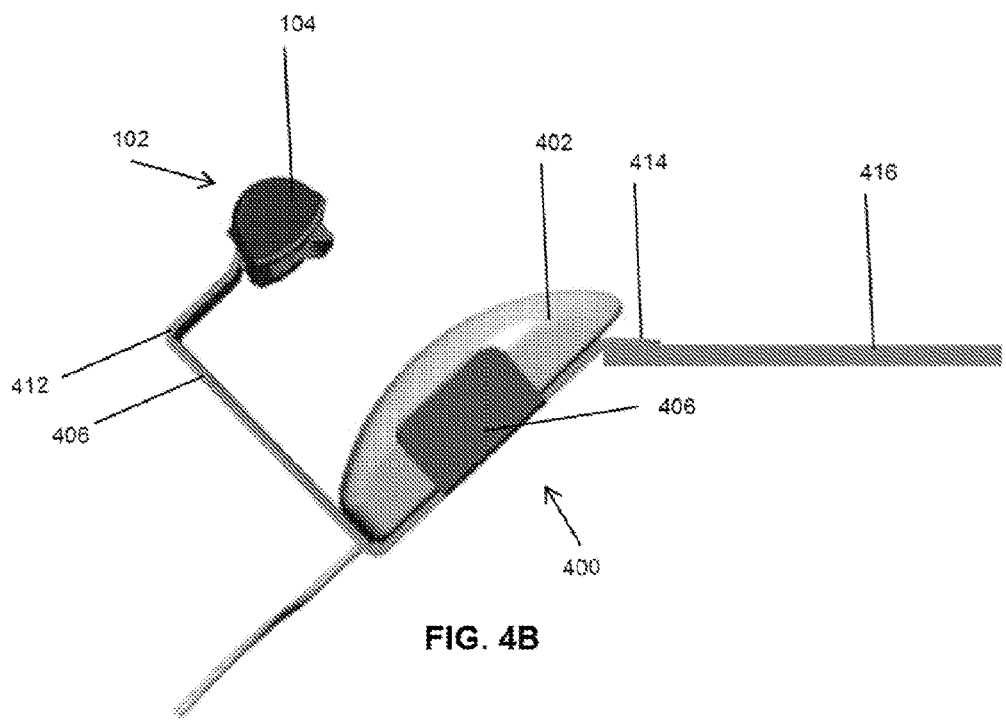

An example is shown in FIGS. 4A-4B. These figures illustrate a germicidal device 100 used in connection with a mounting assembly comprising a receptacle 400 configured to receive a mouse. The receptacle 400 may be configured to hold a mouse 402 within the illumination area of the germicidal light source of the germicidal device 100. The receptacle 400 may comprise a surface 404 configured to support the mouse 402. The receptacle may optionally comprise features configured to help secure the object in place after being placed into the receptacle, and/or to guide proper placement into the receptacle. For example, the receptacle 400 may optionally comprise sides 406 to assist in holding the mouse 402 in place, and additionally or alternatively may comprise an opening 410 configured to allow passage of a mouse cord, which may help to guide proper placement of the mouse into the receptacle and to help hold the mouse in place within the receptacle.

The mounting assembly of FIGS. 4A-4B may comprise an extension attached to the light assembly 102 of the germicidal device 100, such that the germicidal light source is at a fixed location relative to the receptacle 400. For example, an extension 408 may extend at a right angle from the surface 404. This first end of the extension 408 may be attached to or integrally formed with the receptacle 400. A second end of the extension 408 may be attached to or integrally formed with the housing 104 of the light assembly 102. The extension 408 may comprise a bend 412 between the first and second ends such that the germicidal light source is directed toward the surface 404. As such, when the mouse 402 is placed into the receptacle 400 by being placed onto the surface 404, the germicidal light source is configured to project onto the mouse 402.

A mounting assembly comprising a receptacle to receive a contact surface may have any suitable configuration in order to removably hold a contact surface at a fixed location relative to the germicidal lights source, and may be configured to have a desired distance between the germicidal light source and the contact surface. For example, the extension 408 of the mounting assembly of FIGS. 4A-4B may be configured such that the distance between the germicidal light source and a top surface of a mouse is between about 1 inch and about 10 inches; between about 2 inches and about 8 inches, between about 1 inch and about 5 inches, between about 5 inches and about 10 inches, about 2 inches, about 4 inches, about 6 inches, about 8 inches, or about 10 inches, or more than about 10 inches.

The mounting assembly may optionally be configured to be attached to another object (e.g., a countertop, a cart, or the like). For example, the receptacle 400 may optionally be secured to a surface (e.g., secured to a desktop via screws). As shown, the receptacle 400 may comprise a mounting lip 414 comprising one or more mounting holes (here, two mounting holes) configured to receive screws. In one variation, the mounting lip 414 may be secured to the back of a mounting surface 416 (e.g., a keyboard platform of a desk or cart), such that the surface 404 extends at a downward angle from the back of the mounting surface 416, as shown in FIG. 4B.

Point-of-Sale Device Mount

Figure 7A:
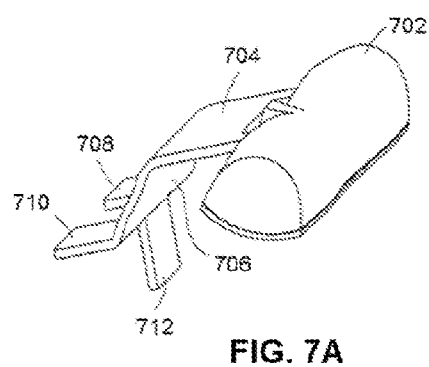
FIGS. 7A-7B show perspective and side views of the germicidal device of FIGS. 1A-1C comprising another exemplary mounting assembly described herein.
Figure 7B:
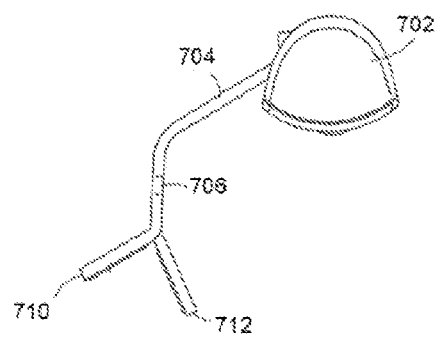

FIGS. 7A-7B illustrate perspective and side views, respectively, of the germicidal device 100 used with a point-of-sale device mount 700. As shown in there, the housing 702 may be connected to a support member 704 having an angled section 706. The angled section 706 may extend approximately at a 45 degree angle downwardly from the support member 704, where it may extend outwardly to form attachment members 708 and 710 having a gap therebetween. Attachment members 708, 710 may be substantially parallel to the support member 704, and may form an orthogonal notch with attachment member 712. This orthogonal notch may be used for fastening the adjustable attachment device to a top edge of an object, such as a point-of-sale device. As seen in FIG. 7B, there may be adhesive material (e.g., tape, a portion of a hook and loop fastener) on the underside surfaces of the attachment members 708, 710, and 712, which may be used to attach the mount 700 to an edge of a point-of-sale device. When held in a fixed position by the mount 700, the germicidal device 100 may be configured to disinfect the touch surfaces of the point-of-sale device.

Figure 7C:
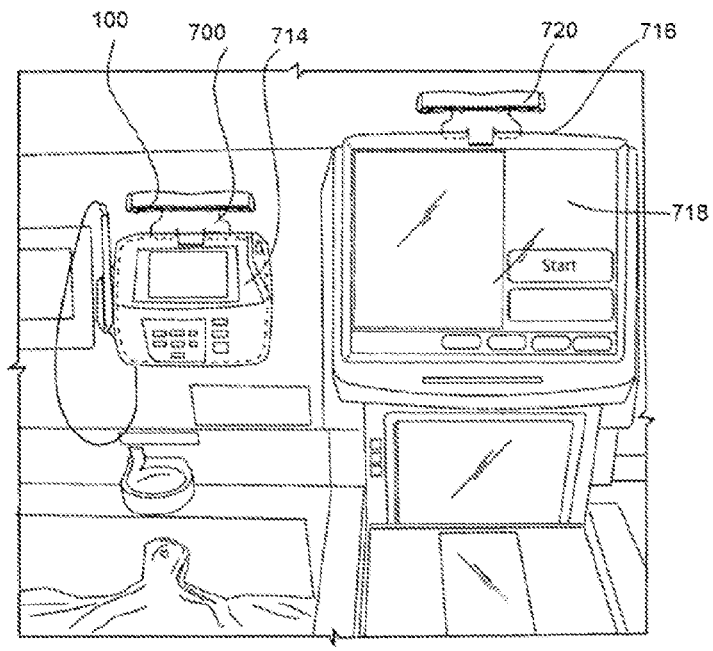
FIG. 7C shows the germicidal devices and mounting assemblies of FIGS. 7A-7B mounted on a point-of-sale system.

FIG. 7C illustrates a perspective view of the germicidal device 100 used with the mount 700 of FIGS. 7A-7C on a point-of-sale system. The point-of-sale system may comprise a first checkout device 716 having a contact surface, here a touchscreen 718. At the upper portion of the first checkout device 716, the germicidal device 100 may be attached by fixing the orthogonal notch of the mount 700 to an upper edge of the checkout device 716. This may allow the germicidal device 100 to project light downwardly onto the surface of the touchscreen 718. Similarly, a second checkout device 714 used for payment may also have a germicidal device 100 attached at an upper surface via a mount 700. This may allow the second germicidal device 100 to project light downwardly onto the contact buttons of the checkout device 714.

In some other variations of mounts configured for use with point-of-sale devices, a mount and/or the housing of the germicidal device 100 may be configured reduce the accessibility of the germicidal device 100 to a user. For example, an additional casing or shell may extend at least partially around the germicidal device 100 to provide additional protection. In variations of germicidal devices comprising controls or switches, the mount and/or housing may be configured to reduce the accessibility of the controls or switches to a user.

Figure 8A:
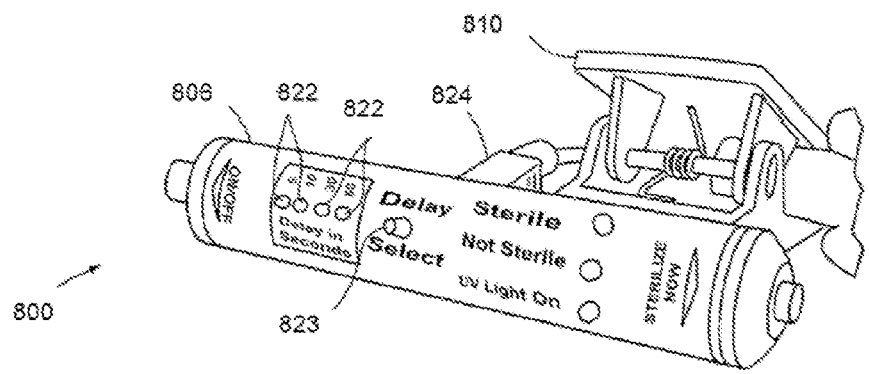
FIGS. 8A-8B depict perspective views another exemplary variation of a germicidal device described herein.
Figure 8B:
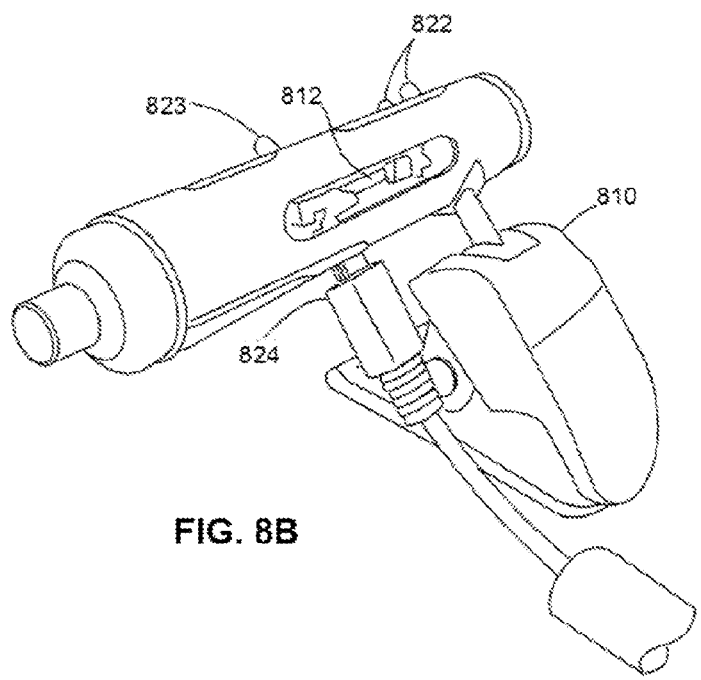
Figure 8C:
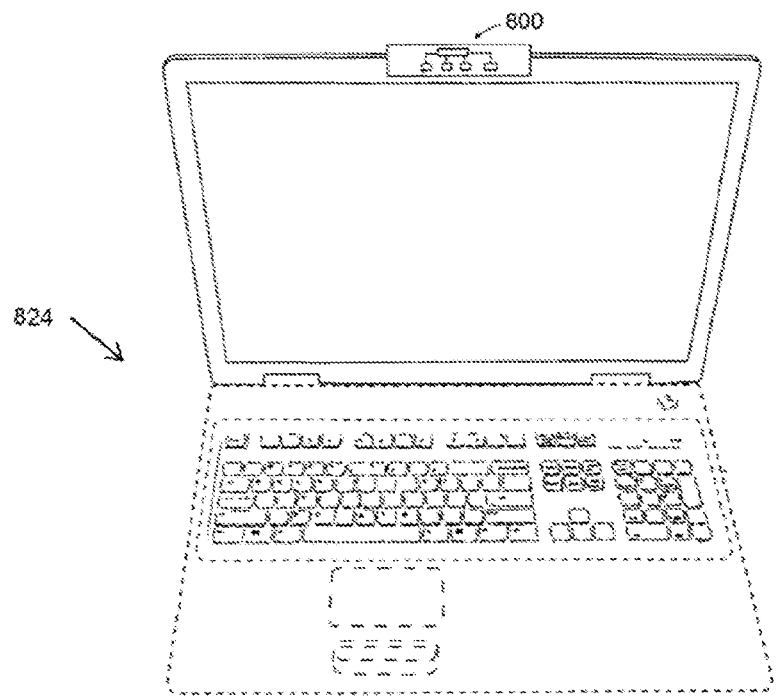
FIGS. 8C-8H illustrate the germicidal device of FIGS. 8A-8B attached to different human interface devices.
Figure 8D:
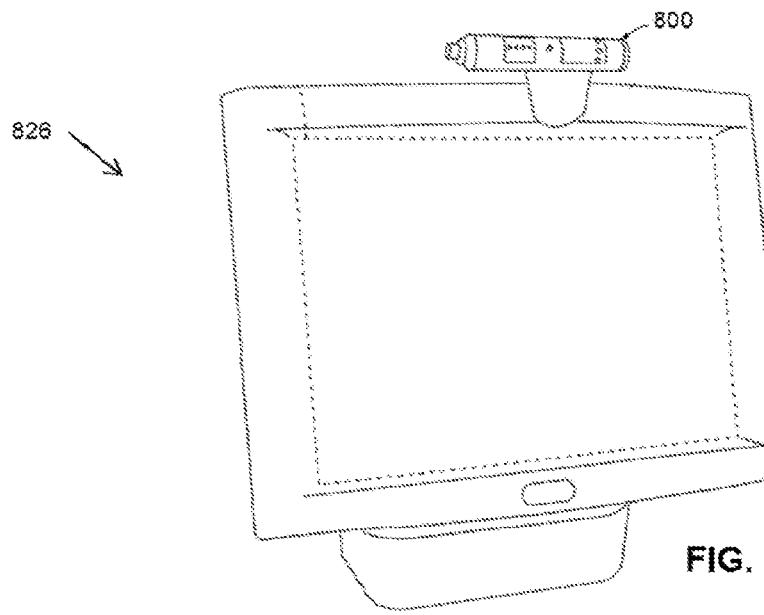
Figure 8E:
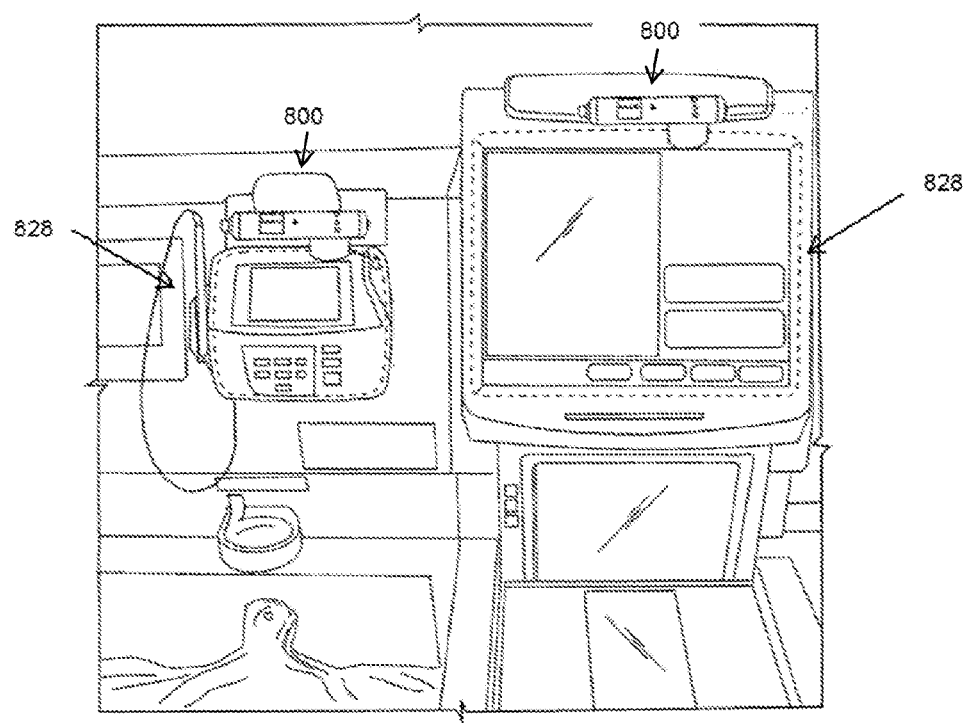
Figure 8F:
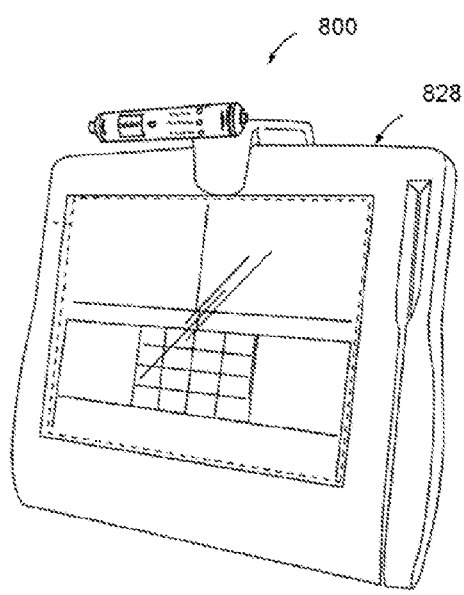
Figure 8G:
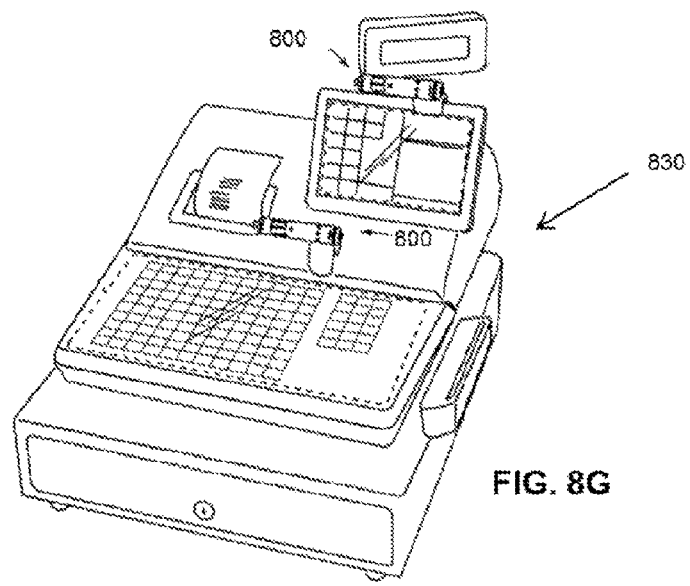
Figure 8H:
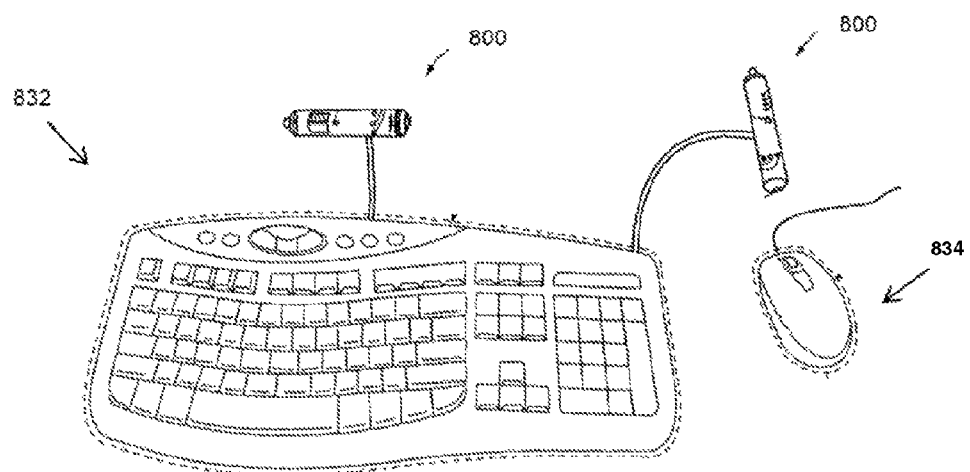
Figure 9:
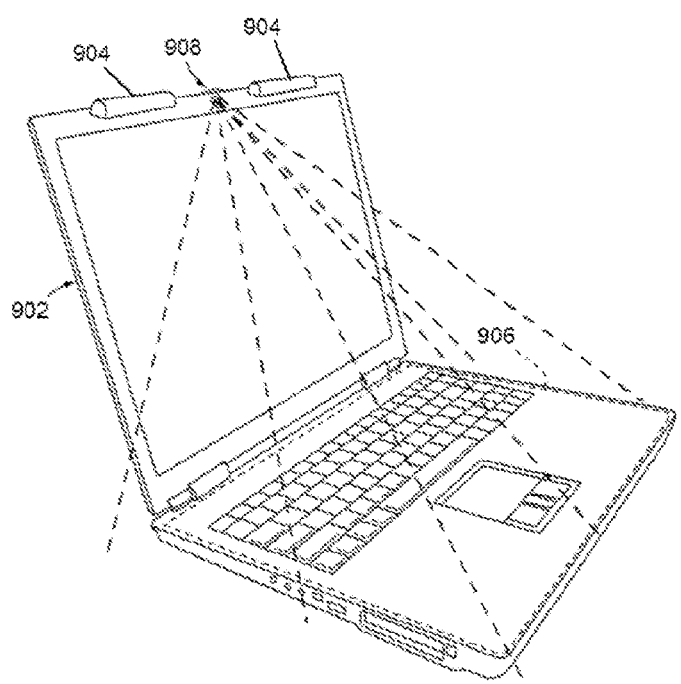
FIG. 9 depicts an exemplary integrated germicidal device.

It should be appreciated that the germicidal devices described herein may be attached to or near any suitable contact surface, using the mounting assemblies described herein, or using other mounting assemblies. As other examples, FIGS. 8C-8H show the germicidal device 800 of FIGS. 8A-8B mounted on various human interface devices, such as a laptop (824) (FIG. 8C), a monitor (826) (FIG. 8D), point-of-sale systems (828) (FIG. 8E-8F), a cash register (830) (FIG. 8G), and a keyboard (832) and mouse (834) (FIG. 8H). It should be appreciated that any of the mounting assemblies may be configured to be used with any of the germicidal devices described herein, and similarly, any of the germicidal devices described herein may be used with any of the human interface devices, peripheral devices, and other contact surfaces described herein. Additionally, in other variations, a germicidal device 900 may be integrated with a human interface device. For example, as illustrated in FIG. 9, a germicidal system may be integrated with the human interface device 902 (e.g., a laptop computer). As shown there, one or more germicidal light sources 904 and one or more proximity sensors 908 may be integrated at the top of the laptop screen and directed towards the keyboard and touchpad area 906. However, it should be appreciated that the germicidal light source 904 and/or the sensor 908 may be located at any suitable location (e.g., on different sides of the LCD screen, the top, the bottom, or a combination thereof, so long as the germicidal light source 904 may adequately project germicidal light on the contact area and the proximity sensor has an appropriate field of view.

Disinfection Methods

Generally, the disinfection methods described herein may allow for disinfection of a contact surface after contact has occurred between a user and the contact surface. The protocols may allow for cessation of any active disinfection cycle when a human is near or within the illumination area. In some variations disinfection methods may also allow for periodic disinfection of a surface, even when contact has not occurred between a user and the contact surface.

Generally, in order to implement the disinfection protocols described herein, the germicidal systems may comprise a sensing system configured to detect human presence or activity. The sensing system may have two primary functions. First, the sensing system may be configured to determine when a contact surface should be disinfected. For example, the sensing system may be configured to determine when a user has interacted with a human interface device (e.g., when a human has pressed keys on a keyboard of a computer, when a human has moved a computer mouse or pressed one of its buttons, when a human has touched a touchscreen, or the like). Second, the sensing system may determine when a person is near or in the irradiation area of the germicidal light source, in order to prevent human exposure to irradiation.

The sensing system may comprise one or more sensors. As described above, the germicidal devices described herein may comprise one or more proximity sensors. Additionally or alternatively, the germicidal systems described herein may comprise one or more sensors configured to detect interaction with a human interface device. A human interface device may be any electronic device that has a wired or wireless connection with a germicidal device, is configured to interact or interface with the germicidal device (e.g., by having germicidal software installed on the human interface device), and that comprises a contact surface or has a peripheral device with a contact surface that is to be disinfected by the germicidal device. The interaction sensor(s) may be integrated into the human interface device (e.g., via software) in order to receive information from existing inputs. Input may include inputs from peripheral devices, such as moving a mouse or pressing a key on a keyboard, or from touching a touchpad or touchscreen, or the like. In variations in which the keyboard and/or mouse are peripheral devices of a human interface device, the detection of interaction may be communicated to the processor utilizing a USB connection, other suitable wired or wireless communication connection, or a combination thereof. In some instances, the detection of activity through an interaction sensor may indicate that the contact surface may have become dirty or infected, and may prompt the start of a disinfection period, as described in detail herein. As such, software monitoring for interaction lends to a number of advantages, including limiting unnecessary germicidal light use and performing the task of disinfection shortly after the time when pathogens may be introduced onto the contact surface. Additionally or alternatively, the detection of activity through an interaction sensor may indicate the presence of a user, and thus may indicate that the germicidal light source should be turned off in order to avoid exposure.

It should be appreciated that the sensing systems described herein may comprise more than one sensor of any type. For example, a system may comprise more than one sensor to detect interaction with a human interface device (e.g., a sensor to detect keyboard input and a sensor to detect mouse clicks). Additionally or alternatively, the system may comprise more than one sensor to detect human proximity (e.g., sensors located in different locations, different types of proximity sensors). The output of these sensors may be combined in a disinfection protocol in any suitable manner. For instance, in a variation having two sensors to detect interaction and two sensors to detect proximity, only one of the sensors to detect interaction may trigger a disinfection cycle, while the other three sensors may trigger the germicidal light source to be turned off, as explained in detail herein.

Single-Mode Sensing Systems

In one variation of the sensing systems described herein, the sensing system may be a "single-mode" system—that is, it may comprise only one type of sensor. In one variation, the single-mode sensing systems may be "standalone" sensing systems that do not rely on input into a human interaction device or its peripherals. For example, a standalone sensing system may comprise one or more proximity sensors, and no interaction sensors. Germicidal devices having such a "standalone" single-mode sensing systems not relying on input into a human interaction device may be used, for example, with non-electronic contact surfaces, such as countertops, sinks, doorknobs, and the like. As another example, germicidal devices having such a standalone sensing system may be used with electronic contact surfaces for which software integration is not feasible or is not desirable, such as tablet computers, point-of-sale systems, kiosks, automated teller machines, biometric scanners, electronic keypads, infusion pumps or other medical equipment, and the like. In both instances, germicidal devices having a standalone sensing system may be configured to be wirelessly connected to a network and/or administrator interface. This may allow information to be sent to and from the germicidal devices. In contrast to germicidal devices connected to a human interface device and controllable via software on the human interface device, germicidal devices having standalone sensing systems may be controlled (e.g., have operational parameters changed, have data collected or analyzed) using an administrator interface via a wireless connection to a network, as described in more detail herein.

In one variation of a germicidal device having a stand-alone sensing system comprising one or more proximity sensors, the germicidal device may be configured to respond to a detection event by a proximity sensor. The germicidal device may be configured such that a detection event while the disinfecting light is off may start the beginning of a delay period preceding a disinfection cycle, because such a detection event may indicate that the contact surface may have been touched. A detection event during the delay period may reset the delay period to restart at its beginning. A detection event while the germicidal light source is on may result in the germicidal light source being turned off, because such a detection event may indicate that a person is within the illumination area of the germicidal light source.

Figure 10A:
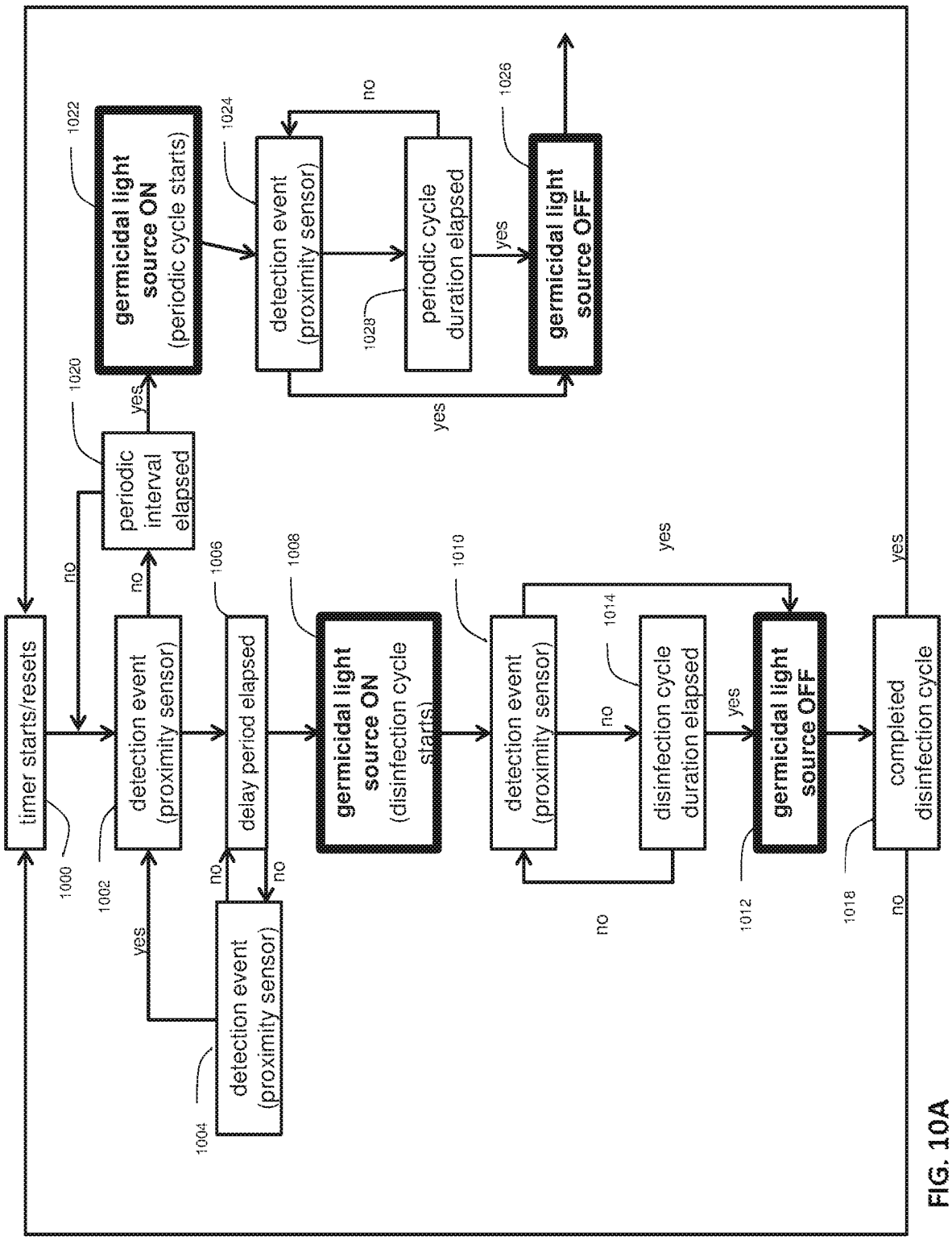
FIGS. 10A-10B depict exemplary disinfection methods.

An exemplary disinfection method for a germicidal device comprising a standalone sensing system is shown in FIG. 10A. The method may begin when a timer starts (1000). If a proximity sensor detects an event (1002), the delay period begins. If a proximity sensor detects an event during the delay period (1004), the delay period resets. If the full delay period has elapsed without a detection event (1006), the germicidal light source turns on, and the disinfection cycle starts (1008). During the disinfection cycle, if a proximity sensor detects an event (1010), the germicidal light source turns off (1012). If the disinfection cycle duration has elapsed (1014) without a detection event, the germicidal light source turns off at its completion (1012). This results in a completed disinfection cycle (1018). At the completion of the disinfection cycle, the timer resets (1000).

The disinfection method of FIG. 10A may also comprise a periodic disinfecting function. This periodic disinfection function may have the effect of a "deep cleaning" by turning the germicidal light source on for a duration longer than the standard disinfection cycle. In the variation shown in FIG. 10A, if a complete disinfection cycle occurs, a countdown to the next periodic cycle may reset. As such, a periodic cycle may occur when a periodic interval has elapsed since the last completed disinfection cycle or periodic cycle. More specifically, once the timer starts or resets (1000), if the periodic interval elapses (1020), the germicidal light source turns on, and the periodic cycle begins (1022). A periodic cycle, like a standard disinfection cycle, may be interrupted by a detection event. If a proximity sensor detects an event (1024) during the periodic cycle, the germicidal light source is turned off (1026). If the complete periodic cycle duration has elapsed (1028) without a detection event, the germicidal light source turns off at its completion (1026). This results in a completed periodic cycle, and the timer resets (1000). Although in the method shown in FIG. 10A the countdown to the next periodic cycle resets if a complete disinfection cycle occurs, it should be appreciated that in other variations, a periodic cycle may occur each time a given periodic interval has elapsed, regardless of when or whether a standard disinfection cycle has occurred.

Dual-Mode Sensing Systems

In other variations of the sensing systems described herein, the sensing system may be a "dual-mode" system—that is, it may comprise two types of sensors. In one variation of a dual-mode sensing system, the sensing system may comprise one or more proximity sensors and one or more interaction sensors. Germicidal devices having such a dual-mode sensing system comprising one or more proximity sensors and one or more interaction sensors may be used, for example, with contact surfaces that are part of or near a human interface device having software (described in more detail herein) installed to interface with the germicidal device. The one or more interaction sensors of the sensing system may be configured to detect interaction with a human interface device or with one or more of its peripheral devices. For example, the interaction sensors may be configured to detect input via a keyboard (e.g., pressing a key on a keyboard), via a mouse (e.g., moving a mouse, clicking a button on a mouse, rotating a scroll wheel on a mouse), a trackpad (e.g., touching a trackpad), a touchscreen (e.g., touching the touchscreen), and/or the like. Information from the one or more interaction sensors may be used, along with information from the proximity sensor, by the sensing system. It should be appreciated that in other variations, the sensing systems described herein may comprise more than two types of sensors (e.g., three types of sensors).

A germicidal device having a dual-mode sensing system comprising one or more proximity sensors and one or more interaction sensors may be configured such that there is one type of detection event that may lead to disinfection (detection of interaction), while there may be two types of detection events that may lead to cessation of an ongoing disinfection cycle (detection of proximity or interaction). This sensing system may thus minimize risk of exposure to the germicidal light source by disinfecting in response to user contact with a device, while using both types of sensors to turn off the disinfection light if human presence is detected. Put another way, the germicidal device may be configured such that an interaction detection event while the germicidal light source is off may start the beginning of a delay period preceding a disinfection cycle. However, the germicidal device may be configured such that a proximity detection event while the germicidal light source is off may not start the beginning of a delay period preceding a disinfection cycle. During the delay period, the germicidal device may be configured such that either a proximity or interaction detection event may reset the delay period to restart at its beginning. Similarly, while the germicidal light source is on, the germicidal light source may be turned off if there is either a proximity or interaction detection event. Generally speaking, this may result in a disinfection protocol in which the interaction sensor may monitor for interaction with a human interface device via one or more inputs such as a keyboard, mouse, trackpad, or touchscreen. If surface contact is detected by the interaction sensor, after a delay period has passed, the germicidal light source may be turned on. While the germicidal light source is on, both the proximity sensor and interaction sensor may continue to operate. If either sensor registers a detection event (i.e., if a person touches the human interface device or comes near it), the germicidal light source may turn off. If neither sensor registers a detection event, the disinfection cycle may continue to completion.

Figure 10B:
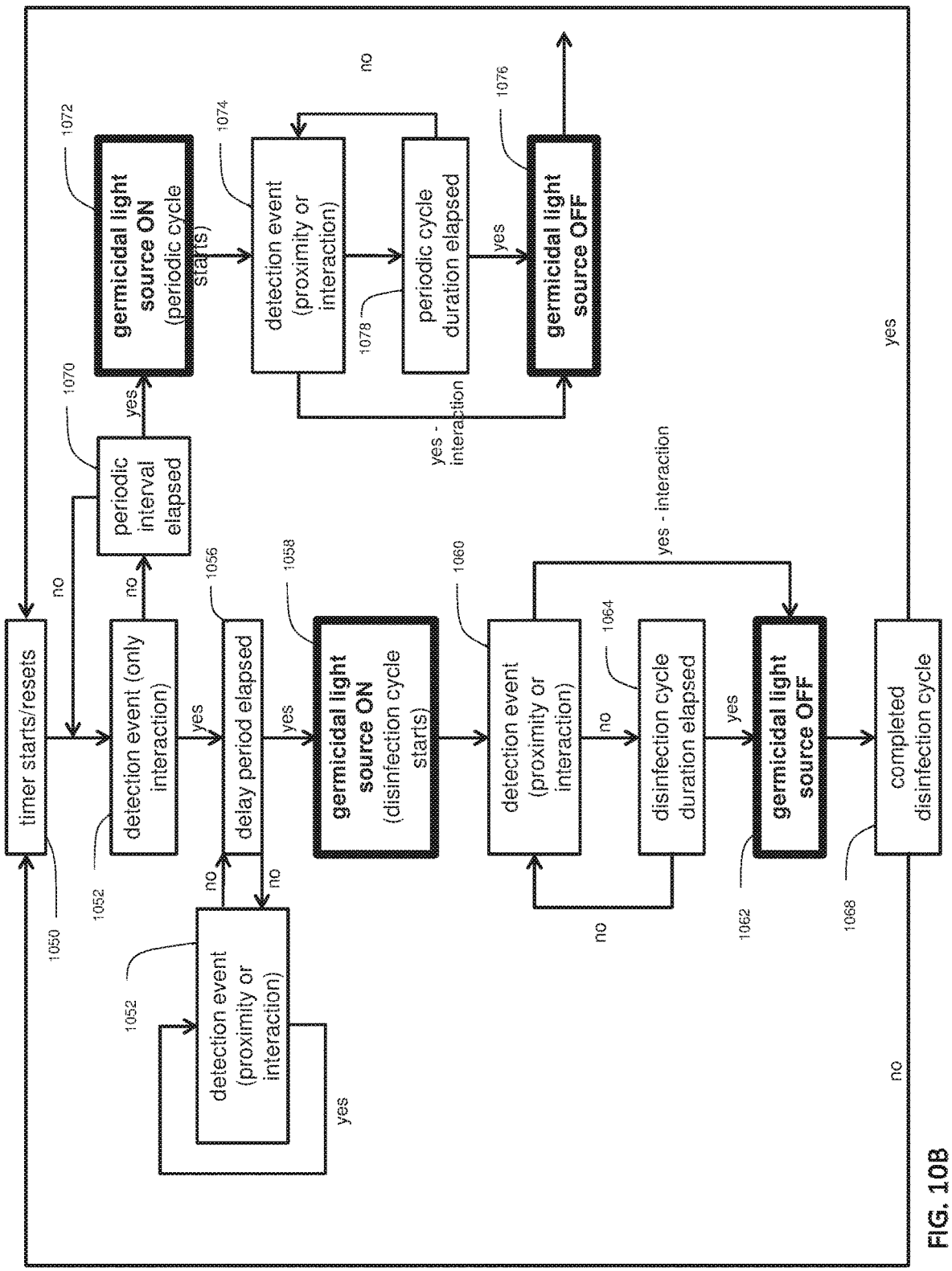

An exemplary disinfection method for a germicidal device comprising a dual-mode sensing system comprising one or more proximity sensors and one or more interaction sensors is shown in FIG. 10B. The method may begin when a timer starts (1050). If an interaction sensor detects an event (1052), the delay period begins. If during the delay period there is a detection event by either a proximity sensor or an interaction sensor (1054), the delay period resets. If the full delay period has elapsed without a detection event (1056), the germicidal light source turns on, and the disinfection cycle starts (1058). During the disinfection cycle, if either a proximity sensor or an interaction sensor detects an event (1060), the germicidal light source turns off. If a proximity sensor detects an event during the disinfection cycle, the disinfection cycle pauses: that is, the germicidal light source turns off temporarily for a delay period, and if neither type of sensor detects an event during the delay period, the disinfection cycle resumes (not shown in FIG. 10B). If an interaction sensor detects an event during the disinfection cycle, the germicidal light source turns off (1062), the timer resets (1000), and a new delay period prior to a disinfection cycle is started (1052). If the disinfection cycle duration elapses (1064) without a detection event, the germicidal light source turns off at its completion (1062). This results in a completed disinfection cycle (1068). At the completion of the disinfection cycle, the timer resets (1000).

Like the disinfection method of FIG. 10A, the disinfection method of FIG. 10B may also comprise a periodic disinfecting function. This periodic disinfection function may have the effect of a "deep cleaning" by turning the germicidal light source on for a duration longer than the standard disinfection cycle. In the variation shown in FIG. 10B, if a complete disinfection cycle occurs, a countdown to the next periodic cycle may reset. As such, a periodic cycle may occur when a periodic interval has elapsed since the last completed disinfection cycle or periodic cycle. More specifically, once the timer starts or resets (1050), if the periodic interval elapses (1070), the germicidal light source turns on, and the periodic cycle begins (1072). A periodic cycle, like a standard disinfection cycle, may be interrupted by a detection event. If an event is detected by a proximity sensor or an interaction sensor during the periodic cycle (1074), the germicidal light source is turned off. If a proximity sensor detects and event during the periodic cycle, the periodic cycle pauses: that is, the germicidal light source turns off temporarily for a delay period, and if neither type of sensor detects and event during the delay period, the periodic cycle resumes (not shown in FIG. 10B). If an interaction sensor detects an event during a periodic cycle, the germicidal light source turns off (1076), and the timer resets (1000). If instead the complete periodic cycle duration has elapsed (1078) without a detection event, the germicidal light source turns off at its completion (1076). This results in a completed periodic cycle, and the timer resets (1000). Although in the method shown in FIG. 10B the countdown to the next periodic cycle resets if a complete disinfection cycle occurs, it should be appreciated that in other variations, a periodic cycle may occur each time a given periodic interval has elapsed, regardless of when or whether a standard disinfection cycle has occurred.

It should be appreciated that when the germicidal device comprises one or more indicators, the state of the one or more indicators may reflect a particular step or steps of a disinfection method. For example, in variations in which the germicidal device comprises one or more indicator lights having different colors, an indicator light of a first color may be illuminated while the germicidal light source is on; an indicator light of a second color may be illuminated during a delay period; and an indicator light source of a third color may be illuminated after a completed disinfection cycle or completed periodic cycle.

Operational Parameters

The various operational parameters may be set to any suitable time periods. For example, the disinfection cycle duration may be chosen based on one or more factors, such as but not limited to the light output of the germicidal light source, distance of the germicidal light source from a contact surface, and/or the quantity or character of the pathogens expected to be on the contact surface. Generally, different pathogens (e.g., methicillin-resistant Staphylococcus aureus (MRSA), *Escherichia coli* (*E. coli*), H1N1 flu virus, *Clostridium difficile* (*C. diff*)) may require differing amounts of UV energy in order to be reduced or eliminated. In some variations, the disinfection cycle duration may be between about 1 minute and about 1 hour, between about 1 second and about 20 minutes, between about 1 second and about 30 minutes, between about 1 minute and about 20 minutes, between about 5 seconds and about 10 minutes, between about 5 seconds and about 20 minutes, between about 10 seconds and about 10 minutes, between about 30 seconds and about 5 minutes, between about 30 seconds and about 4 minutes, between about 5 seconds and about 5 minutes, or between about 10 seconds and about 30 seconds. In one variation, the disinfection cycle duration using a germicidal light source comprising 1 W bulb may be about 160 seconds for a contact surface located about 15 inches from the bulb. In some variations, a particular disinfection cycle duration may be chosen based on the contact surface to be disinfected and the expected distance between the contact surface and the germicidal light source. For example, for the mounting assemblies described herein, a desktop setting may have a disinfection cycle duration of between about 1 minute and about 20 minutes, between about 30 seconds and about 10 minutes, between about 5 minutes and about 10 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, or about 12 minutes. A laptop setting may have a disinfection cycle duration of between about 1 minute and about 20 minutes, between about 1 minute and 15 minutes, between about 5 minutes and about 15 minutes, between about 10 minutes and 15 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, or about 16 minutes. A tablet setting may have a disinfection cycle duration of between about 1 minute and about 20 minutes, between about 30 seconds and about 10 minutes, between about 5 minutes and about 10 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, or about 12 minutes. A touchscreen may have a disinfection cycle duration of between about 1 minute and about 20 minutes, between about 1 minute and 15 minutes, between about 5 minutes and about 15 minutes, between about 10 minutes and 15 minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, or about 16 minutes.

The periodic cycle duration may similarly be chosen based on one or more factors, such as but not limited to the light output of the germicidal light source, distance of the germicidal light source from a contact surface, and/or the quantity or character of the pathogens expected to be on the contact surface. In some variations, the periodic cycle duration may be between about 1 minute and about 2 hours, between about 1 minute and about 1 hour, between about 5 minutes and about 1 hour, between about 5 minutes and about 30 minutes, between about 5 minutes and about 30 minutes, between about 20 minutes and about 40 minutes, or between about 10 minutes and about 20 minutes. The periodic cycle duration may in some instances be a multiple of the standard disinfection cycle duration, such as a factor of about 1.1 to about 3, about 1.25 to about 2, about 1.5 to about 2, or about 1.67. In other variations, the periodic cycle may be the same length as the standard disinfection cycle duration (i.e., a factor of about 1). In yet other variations, the periodic cycle may be shorter than the standard disinfection cycle duration, such as a factor of between about 0.5 and about 0.9. In some variations, a particular periodic cycle duration may be chosen based on the contact surface to be disinfected and the expected distance between the contact surface and the germicidal light source. For example, for the mounts described herein, a desktop setting may have a periodic cycle duration of about 2 minutes, about 4 minutes, about 6 minutes, about 8 minutes, about 10 minutes, about 12 minutes, about 14 minutes, about 16 minutes, about 18 minutes, about 20 minutes, about 22 minutes, or about 24 minutes; a laptop setting may have a periodic cycle duration of about 2 minutes, about 4 minutes, about 6 minutes, about 8 minutes, about 10 minutes, about 12 minutes, about 14 minutes, about 16 minutes, about 18 minutes, about 20 minutes, about 22 minutes, about 24 minutes, about 26 minutes, about 28 minutes, about 30 minutes, or about 32 minutes; a tablet setting may have a periodic cycle duration of about 2 minutes, about 4 minutes, about 6 minutes, about 8 minutes, about 10 minutes, about 12 minutes, about 14 minutes, about 16 minutes, about 18 minutes, about 20 minutes, about 22 minutes, or about 24 minutes; and a touchscreen may have a periodic cycle duration of about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, or about 20 minutes. In situations in which *C. diff* is suspected to be on a contact surface, the periodic cycle duration may be increased. For example, the increase may be between a factor of about 1.5 and a factor of about 3. In some variations, the increase may be a factor of about 2. In one example the periodic cycle duration may be about 20 minutes for a desktop setting; about 27 minutes for a laptop setting; about 20 minutes for a tablet setting; and about 26 minutes for a touchscreen setting.

The periodic interval may have any suitable length. As described above, in some variations, if a complete disinfection cycle occurs, a countdown to the next periodic cycle may reset. As such, a periodic cycle may occur when a periodic interval has elapsed since the last completed disinfection cycle or periodic cycle. In other variations, a periodic cycle may occur each time a given periodic interval has elapsed, regardless of when or whether a standard disinfection cycle has occurred. In some instances the periodic interval may be between about 10 minutes and about 24 hours, between about 1 hour and about 24 hours, between about 30 minutes and about 3 hours, between about 1 hour and 10 hours, between about 1 hour and about 2 hours, between about 2 hours and 5 hours, between about 5 hours and 10 hours, about 1 hour, or about 2 hours.

The delay period may also have any suitable length. In some variations, the delay period may be between about 1 second and about 5 minutes, between about 60 seconds and about 120 seconds, between about 5 seconds and about 120 seconds, between about 30 seconds and about 60 seconds, between about 1 second and about 60 seconds, about 30 seconds, about 60 seconds, about 120 seconds, or more than about 120 seconds. It may be desirable that the delay period may be adequately long enough to make a reasonable assumption that the user is at least temporarily done using a human interface device.

Other Disabling Features

The germicidal systems described herein may comprise other mechanisms for turning off a germicidal light source while it is on, in addition to the controller causing it to turn off in response to a sensing system as described herein. In some variations, the germicidal device may comprise an auto-disabling device. For example, the germicidal device may comprise an auto-disabling sensor configured to detect the orientation or movement of the lamp, such as but not limited to an inertial sensor and/or an accelerometer. If the orientation of the light assembly is altered beyond predetermined angles (e.g., as detected by an inertial sensor) and/or movement is detected (e.g., as detected by an accelerometer), the germicidal light source may be turned off if the germicidal light source is illuminated when the changed orientation or movement is detected. If the germicidal light source is off when the changed orientation or movement is detected, the germicidal light source may be configured to remain off. In some variations, the germicidal light source may be disabled until it is manually reset. In other variations, the germicidal light source may be disabled until an orientation within the acceptable orientation range is detected. The germicidal devices may additionally or alternatively comprise an autotimer override configured to turn off the germicidal light source after it is on for an extended period, to prevent prolonged irradiation in the case of a system malfunction.

Software And User Interface

The germicidal systems described herein may comprise software configured to direct one or more processors of the germicidal system to perform a wide variety of functions. For example, software may contribute to the control of automatic operations of the germicidal system (e.g., turning off a disinfection light source if a proximity sensor detects a nearby user), and/or software may enable a user to manually adjust operational parameters of the germicidal system via a user interface. Software may be configured to control the flow or transmission of data between devices of the germicidal system, and it may enable the germicidal system to collect, store, and/or analyze the transmitted data. Software may be installed or stored on one or more components of the germicidal system, and the location of the software may depend on the configuration of the germicidal system. For example, in some variations germicidal devices comprising dual-mode sensing systems described herein, germicidal software may be installed on one or more human interface devices. In integrated designs, software may be installed on one or more integrated human interface and germicidal devices. In germicidal devices comprising single-mode sensing systems comprising only one or more proximity sensors and that do not rely on input into a human interaction device, software may optionally be installed on one or more germicidal devices. In some variations, one or more germicidal and/or human interface devices may be configured to communicate with one or more remote devices and/or servers via a network, and in these variations, software may be stored on one or more of the remote devices and/or servers.

Functions that may be enabled and/or controlled by software of the germicidal system will be discussed in detail herein by describing multiple representative screens of a user interface. These screens may appear, for example, on a visual display of a human interface device (e.g., a desktop computer, laptop computer, tablet). The screens may provide information related to the human interface device and associated germicidal device and/or allow a user to control various functions of the human interface and/or germicidal device. In variations of germicidal systems connected to a network, user interface screens may additionally or alternatively be displayed on one or more remote devices. In some variations, a user may be required to login (e.g., provide a username and/or password) to the germicidal system (e.g., germicidal system software and/or a network that one or more devices of the germicidal system are connected to) in order for one or more screens of the user interface to be displayed and/or modified. It should be understood that these screens, shown in FIGS. 16A-16F, are representative user interface screens, and the information contained on such screens may not be limited to or include all of what is shown and/or described. The representative screens depict one variation of a layout, and the information shown and/or described may have any suitable layout, including being displayed on any suitable number of screens, windows, and/or tabs. Also, one skilled in the art would recognize that any selectable or adjustable feature (e.g., drop-down menu, radio button, field) that is shown and/or described may be replaced with another suitable selectable or adjustable feature.

In an exemplary variation, a single germicidal device is controlled by software installed on a human interface device, where a portion or peripheral device of that human interface device (e.g., keyboard, mouse, trackpad) is the contact surface to be disinfected. However, it should be appreciated that not all germicidal systems described herein need comprise a user interface as described. For example, in some variations of germicidal devices having standalone sensing systems that do not rely on input into a human interaction device or its peripherals, as described herein, the germicidal devices may not be directly communicatively coupled to a human interface device having software for controlling the germicidal device. In these variations, the standalone germicidal devices may be wirelessly connected to a network, which may allow for control of and other forms of interfacing with the germicidal devices via the network, as described in more detail herein.

Figure 16A:
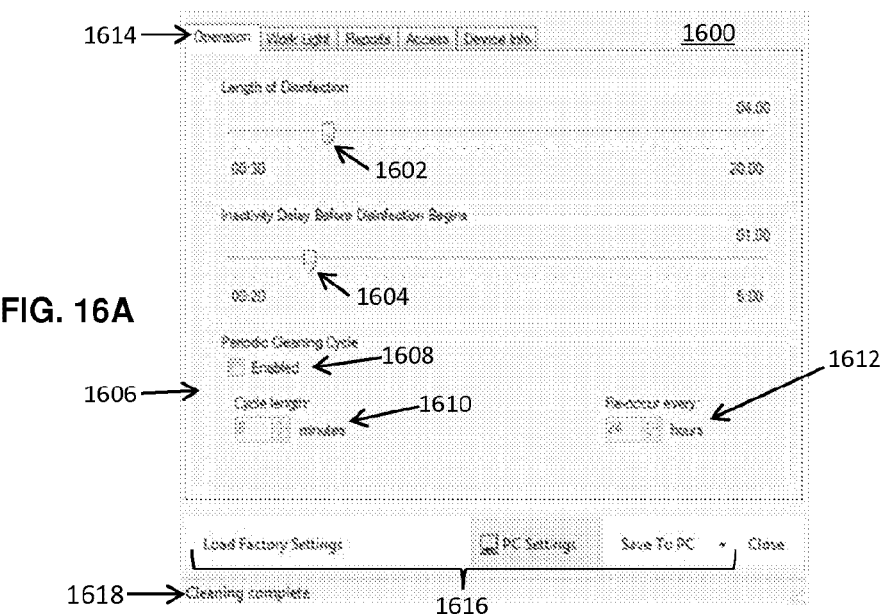
FIGS. 16A-16F are representative user interface screens described herein.

FIG. 16A is a representative operation screen of a user interface of a germicidal system. The operation screen 1600 may allow a user to view and/or adjust one or more operational parameters of a germicidal device. For example, as shown, the operation screen 1600 may display an adjustable disinfection length indicator 1602 and an adjustable delay indicator 1604. The disinfection length indicator 1602 may show the currently selected duration or length of a full disinfection cycle (i.e., the amount of time that a germicidal light source may be on if it is not turned off manually or turned off in response to detection by a sensor). As shown, the disinfection cycle length is set at about 4 minutes, but in the variation shown, a user may change this length from about 30 seconds to about 20 minutes by selecting and moving the length indicator 1602. In other variations, the operation screen 1600 may show a different range of selectable disinfection cycle lengths, and in some variations, a user may enter a specific length (e.g., via a keyboard or touchpad) as opposed to choosing within a defined range.

The adjustable delay indicator 1604 may show the currently selected delay period between a detection event (i.e., an event, such as detection by an interaction sensor, which may indicate that a contact surface may be contaminated) and the start of a disinfection cycle. As shown, the delay period is set at about 1 minute, but in the variation shown a user may change this delay period from about 20 seconds to about 5 minutes by selecting and moving the delay indicator 1604. In other variations, the available range of delay periods may be different, or a user may enter a specific delay period as opposed to choosing from within a defined range.

The operation screen 1600 may display a periodic cleaning cycle area 1606 that may allow a user to choose parameters of a periodic, or deep, cleaning cycle. A periodic cycle may occur with a specific frequency or at specific intervals (e.g., twice a day, three times a day, every shift, every hour, every 2 hours, every 12 hours, every 24 hours). As shown, the periodic cleaning cycle area 1606 may include fields for a user to enable and disable periodic cleaning cycles 1608, choose the length (duration) of the periodic cycle 1610, and choose the frequency of the periodic cleaning cycle 1612 (i.e., the periodic interval).

The operation screen 1600 may include some features that may be present on one or more other screens of a user interface of a germicidal system. For example, one or more identifying features may be displayed on a screen that may indicate the type or category of information that may be viewed and/or modified on the screen. For example, as shown, the identifying feature may be a highlighted or otherwise distinguished named tab 1614. In some variations, one or more screens of the user interface may include one or more saving options 1616 that may allow a user to save the currently selected settings on the screen, revert to default settings, and/or choose from one or more saved settings. As shown, one or more screens of the user interface may comprise a communication field 1618 that may display one or more messages related to the status of the germicidal system. Here, the communication field 1618 indicates "cleaning complete," but any suitable message may be displayed (e.g., a message related to a cleaning cycle, device connection, system error, system location, or the like).

Figure 16B:

FIG. 16B is another variation of a representative operation screen of a user interface. This operation screen 1620 may also allow a user to view and/or modify parameters of a disinfection cycle and periodic cleaning cycle, but it should be appreciated that in other variations, the available options for a user to choose from may be different than those shown in FIG. 16A. For example, instead of allowing a user to choose specific durations of the disinfection cycle and/or the delay between a detection event and the disinfection cycle, the operation screen 1620 may display names of selectable disinfection protocols 1622 (e.g., device-specific protocols such as desktop, laptop, tablet, touchscreen protocols, and/or disease-specific protocols such as those configured to be effective in reducing and/or eliminating *C. diff*). The parameters for each of the protocols may be predetermined, and in some variations, as will be described herein, the parameters may be adjusted on a screen of an administrator interface. As shown, the operation screen 1620 may display a periodic cleaning cycle area 1624 where the only adjustable parameter is the periodic cleaning cycle frequency, or periodic interval, here every one hour or every two hours. In some variations, this frequency may indicate that a periodic cycle may occur one or two hours after the last periodic cycle, regardless of any intervening disinfection cycles. In other variations, this frequency may indicate that a periodic cleaning cycle may occur one or two hours after the last cycle, whether it is a periodic cycle or a disinfection cycle. The duration of the periodic cycle may be predetermined, and it may or may not be adjustable on a screen of a user or administrator interface. In some variations, the periodic cleaning cycle may have a predetermined duration that is related to the duration of the disinfection cycle, as described herein.

Figure 16C:
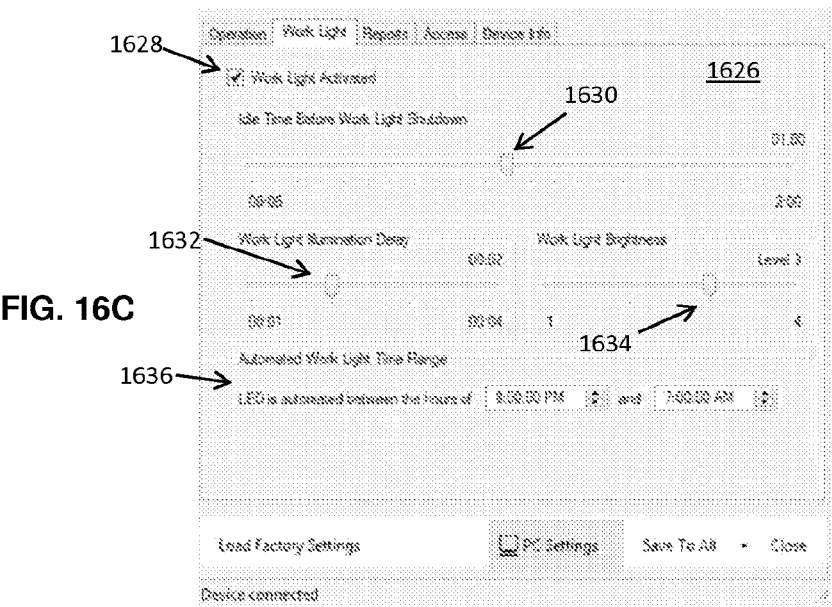

FIG. 16C is a representative work light screen of a user interface of a germicidal device. The work light screen 1626 may allow a user to view and/or modify one or more operational parameters of a work light, such as a work light of a germicidal device described in more detail herein. For example, as shown, the work light screen 1626 may include a work light activation field 1628 that may allow a user to activate or deactivate the work light, such as by selecting and deselecting the work light activation field. Activating the work light may enable the work light to turn on when certain criteria are met, such as when a switch or button on the germicidal device is pressed and/or when a proximity and/or interaction sensor detects a signal. While not shown, the work light screen 1626 may display one or more virtual switches or buttons that a user may select in order to turn the work light on and/or off.

The work light screen 1626 may also display an adjustable idle time indicator 1630, adjustable illumination delay indicator 1632, and adjustable brightness indicator 1634. The adjustable idle time indicator 1630 may indicate the idle time before the work light turns off. As shown it is set at about 1 minute, but a user may select and move the idle time indicator to change this setting. The work light illumination delay indicator 1632 may indicate the time between when the germicidal system receives a signal to illuminate or turn on the work light (e.g., an activation signal from a proximity sensor or interaction sensor, pressing a virtual or physical button) and when the light becomes illuminated or turns on. As shown, the illumination delay is set at about 2 seconds, and a user can select and move the illumination delay indicator 1632 to change this time. The work light brightness indicator 1634 may indicate the level of brightness of the work light, and a user may select and move the brightness indicator to change this level.

The representative work light screen 1626 displays an automated work light time field 1636, which may show one or more time ranges when the work light is automatically activated or turned on, even if, for example, no activation signal from a proximity or interaction sensor is provided. As shown, one automated work light time range is set between 8 PM and 7 AM, but a user may change the start and stop times of this range. In some variations, a user may add or remove one or more automated work light time ranges. In some variations, the work light screen 1626 may have features that allow a user to set one or more automated time ranges to occur on one or more specific days of the week and/or on specific dates (e.g., specific day, month, holiday).

Figure 16D:
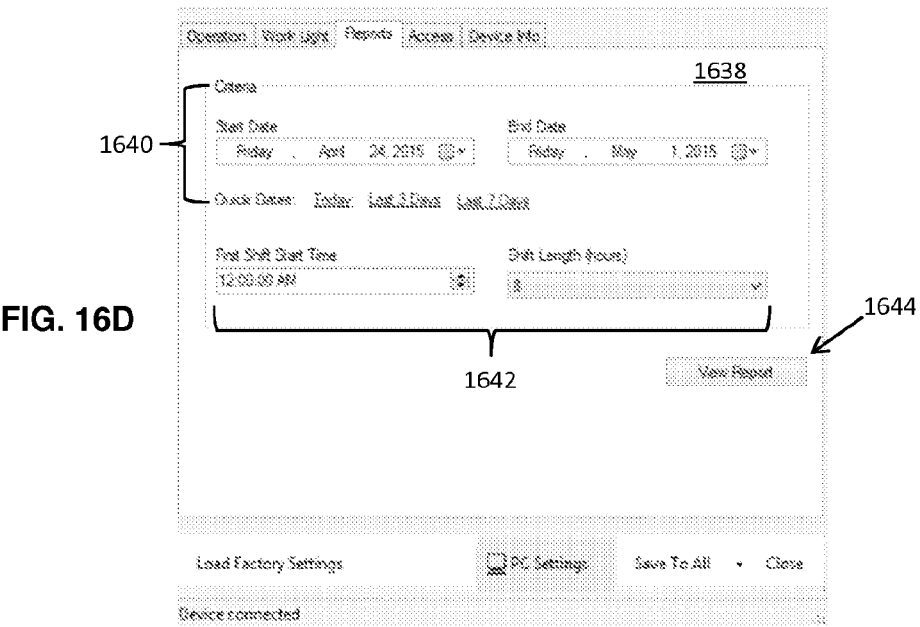

FIG. 16D is a representative report screen of a user interface of a germicidal system. The report screen 1638 may allow a user to select certain report parameters (e.g., report type, report time range, report layout) and prompt the germicidal system to generate a report with those parameters. The report screen 1638 as shown illustrates possible parameters that a user may set, including adjustable time range options 1640 and time increment options 1642. The time range options may allow a user to select a report time range in one or more ways, here by adjustable start and end dates or with selectable time ranges (e.g., today, last 3 days, last 7 days). A report may display information or data obtained during or relevant to the selected time range. A user may use the time increment options 1642 to control the way information or data is organized on a report. For example, as shown, a first shift start time and a shift length time may be adjusted by a user, which may result in the data shown on a report being organized by work shifts having a specific duration. As shown, the report screen 1638 displays a virtual "view report" button 1644 that may be selected by a user in order to direct the germicidal system to generate and display a report with the chosen parameters.

Figure 17:
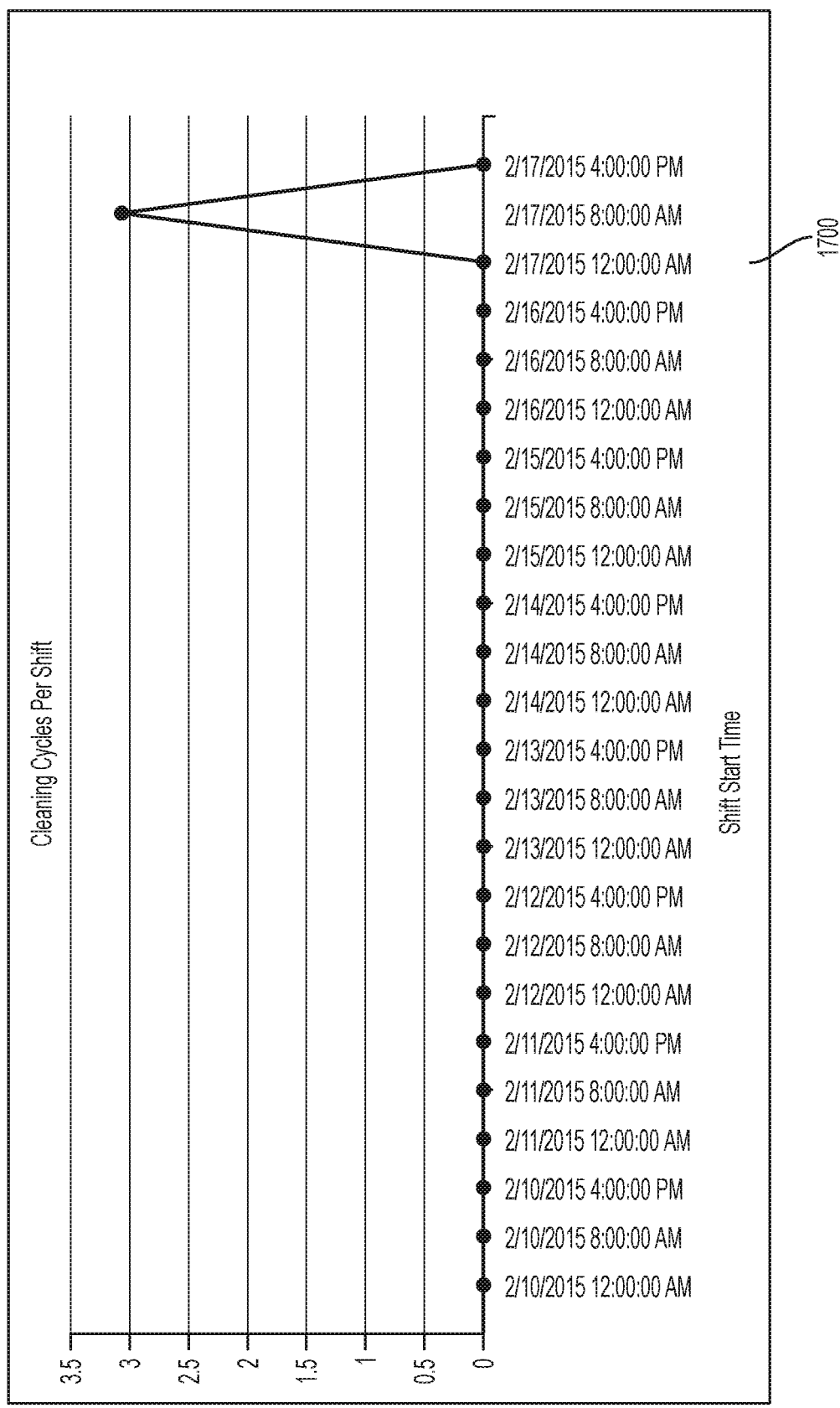
FIG. 17 is an exemplary report described herein.

FIG. 17 is an example of a report that the germicidal system may generate and display on a user interface in response to selections made on a report screen. As shown, the report 1700 displays the number of cleaning cycles performed by a germicidal device in the time range between Feb. 10, 2015 and Feb. 17, 2015, with data points at 8-hour time increments organized by shift start times. It should be appreciated that any suitable report parameters may be set via a user interface to generate any suitable type of report. For example, a germicidal system may be configured to generate reports that include data related to the germicidal system usage times, total bulb on time, completed disinfection cycles, partially (e.g., 25%, 50%, 75%) completed cycles, assigned protocols, problematic system events, the like, and/or any combination thereof. The user interface may allow a user to select the report format (e.g., graphical, tabular, color, black and white), add or modify a title, determine axes, label axes, the like, and/or any combination thereof.

Figure 16E:
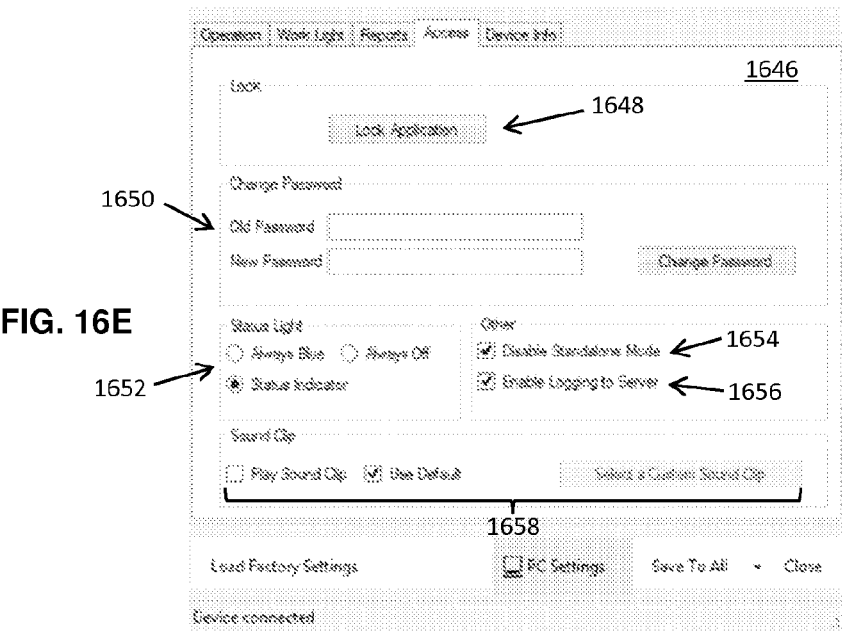

FIG. 16E is a representative access screen of a user interface of a germicidal system. As shown, the access screen 1646 may display options related to user access to functional software of the germicidal system (e.g., software that may allow a user to change operational parameters of the germicidal system). A virtual lock button 1648 may be pressed by a user, which may make a username and/or password required to access functional software of the germicidal system. If the virtual lock button is not pressed, or in some variations if a virtual unlock button is pressed, a user may access functional software and/or make changes to operational parameters of the germicidal system without providing a username and/or password. As shown, the access screen 1646 includes password fields 1650, which may allow a user to enter and/or change an existing password. While the password fields 1650 shown may accept alphanumeric input, it should be appreciated that a germicidal system may be configured to utilize other password forms, such as biometric and/or gesture passwords.

As shown, the access screen 1646 may include fields related to the indicator or status lights on a germicidal device, here status light radio buttons 1652. Various options may be selected or adjusted related to the status light of the germicidal device, such as turning the status light on or off and/or choosing an illuminated color of the status light.

The access screen 1646 may include a standalone mode field 1654, which may allow a user to turn a standalone mode on and off and/or change parameters of the standalone mode. In some variations, the standalone mode may enable a germicidal device to function (e.g., to perform disinfection cycles, periodic cleaning functions, store data, the like, and/or any combination thereof) without exchanging information with a human interface device. That is, in a variation of the germicidal device associated with a human interface and relying on input into a human interaction device or its peripherals for its sensing system (e.g., having a dual-mode sensing system having both proximity and interaction sensors), the standalone mode field may be selected to change to a dual-mode sensing system into a single-mode sensing system using only one or more proximity sensors.

As shown, the access screen 1646 may allow a user to enable and disable transmission of one or more types of data from the germicidal and/or human interface device to a remote server via a network, for example using the logging to server field 1656 shown. For example, in some variations, a germicidal and/or human interface device may be configured to automatically send usage data (e.g., data related to the number and/or completeness of disinfection cycles and/or period cleaning cycles, bulb life, work light usage) to a remote server for monitoring, storage, and/or analysis.

A germicidal and/or human interface device may be configured to produce one or more unique or common sounds for one or more purposes. For example, one or more of the same or different sounds may alert a user when a germicidal and/or human interface device is turned on and/or off, a disinfection and/or periodic cleaning cycle starts or is about to start, a disinfection and/or periodic cleaning cycle stops or is about to stop, the germicidal and/or human interface device connects and/or disconnects from a network, the germicidal device connects and/or disconnects from a human interface device, a device or system error occurs, and/or the like. An access screen of a user interface of a germicidal system may allow a user to change operational parameters related to one or more of these sounds. For example, as shown in FIG. 16E, the access screen 1646 may comprise sound clip fields 1658 that may be selected by a user to play a sound clip, use a default sound clip that may be stored in memory of the germicidal system, or select a new sound clip. In some variations, there may be fields that allow a user to assign the same or different sounds to particular device functions or states.

Figure 16F:
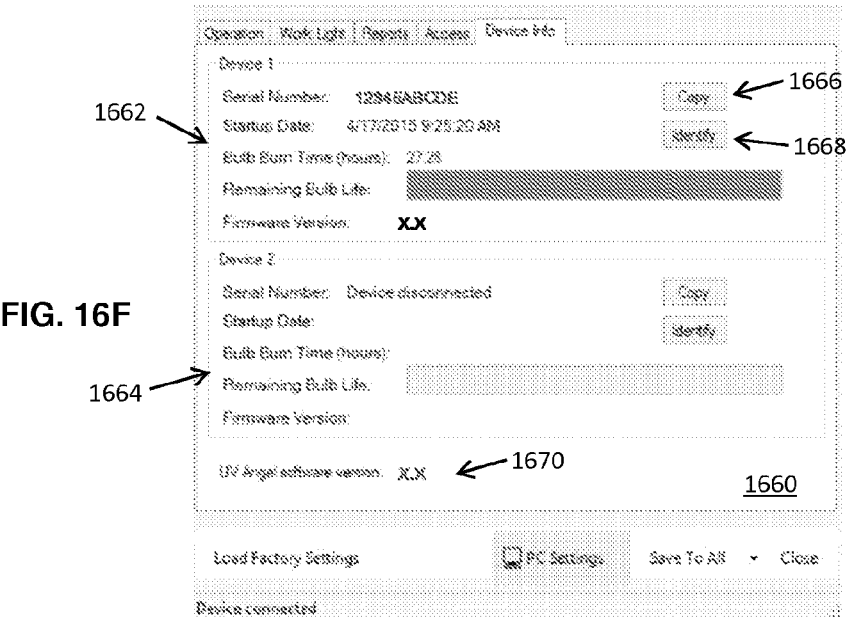

FIG. 16F is a representative device information screen of a user interface of a germicidal system. The device information screen 1660 may allow a user to view and/or modify information related to one or more devices of the germicidal system. For example, the device information screen 1660 may display information related to a germicidal device that is connected to the human interface device comprising the user interface. Additionally or alternatively, the device information screen 1660 may display information related to one or more other germicidal devices, human interface devices, peripheral devices (e.g., mouse, keyboard) that may be connected to a human interface device, a remote device, and/or a server. The device information screen 1660 shown in FIG. 16 comprises a first device field 1662 with information related to a specific germicidal device and a second device field 1664 that indicates that the second device has been disconnected. The first device field 1662 as shown includes the device serial number, startup date, bulb burn time, remaining bulb life, and firmware version, but a device field may display any suitable information related to a device in any suitable alphanumeric or graphical form. In some variations, at least some of the information related to a device may automatically populate a device field. For example, when a germicidal device is connected to a human interface device, at least some of the information related to the germicidal device may be automatically transmitted to the human interface device and displayed on the device information screen of the user interface. In some variations, a device information screen may allow a user to make changes, update, or perform one or more other functions related to device information. For example, as shown, each device field 1662, 1664 on the device information screen 1664 may include a copy virtual button 1666 and an identify virtual button 1670. Selecting the copy virtual button 1666 may copy device information (e.g., copy device information to a clipboard of a device), and selecting the identify virtual button 1670 may instruct the human interface device, for example, to obtain information related to a connected germicidal device. In some variations, the device information screen 1660 may display the germicidal software version 1670 that is installed on one or more devices of the germicidal system, and in some variations, a user may select an option to update the software.

Network and Administrator Interface

A germicidal system may comprise one or more germicidal devices and/or human interface devices that are configured to exchange information with one or more remote devices and/or servers over a network (e.g., local area network, wide area network, the Internet). This may allow for centralized control (e.g., operational parameter adjustment) of all or a portion of the germicidal and/or human interface devices that are connected to the network. For example, an administrator may simultaneously control the germicidal and/or human interface devices in a certain building, on a certain floor, or in a certain department, from one computer. Additionally or alternatively, a germicidal system that is connected to a network may allow for centralized monitoring, storage, and/or analysis of data obtained from all or a portion of the germicidal and/or human interface devices that are connected to the network. Generally, any of the control, data collection, analysis, reporting, or storage functions described herein that may be performed locally for one germicidal device and/or associated human interface device (e.g., via the user interface screens described herein) may be performed remotely by an administrator for one or more germicidal and/or human interface devices.

Figure 18:
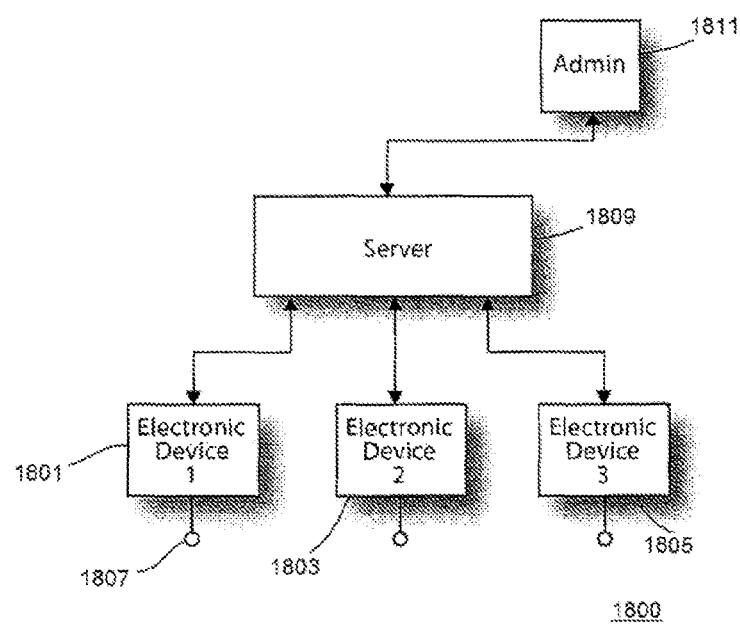
FIG. 18 is a block diagram illustrating a variation of a germicidal system comprising a plurality of germicidal devices configured to communicate via a network.

FIG. 18 is a block diagram illustrating a variation of a germicidal system comprising a plurality of devices configured to communicate via a network. The germicidal system 1800 may comprise one or more human interface devices 1801, 1803, 1805, each having an associated germicidal device 1807, and a remote server 1809. The remote server 1809 may be connected to the same network as the human interface devices 1801, 1803, 1805, which may allow information to be exchanged between the remote server 1809 and the human interface devices 1801, 1803, 1805 in one or two directions. As shown, the germicidal devices 1807 are connected to the human interface devices 1801, 1803, 1805, such that information may be exchanged between the germicidal devices and the remote server 1809 indirectly via the human interface devices (i.e., information may be sent from a germicidal device to a human interface device and then to the remote server via the network). However, it should be appreciated that in some variations, such as germicidal devices comprising standalone sensing systems described herein that are not connected to associated human interface devices, one or more germicidal devices 1807 may be configured to directly connect to the network and exchange information in one or two directions with the remote server 1809. An administrator 1811 may direct the remote server 1809 to exchange information with one or more human interface devices 1801, 1803, 1805 and/or germicidal devices 1807. In some variations, the administrator 1811 may direct the remote server 1809 to process (e.g., compile, store, analyze) information obtained from one or more human interface devices 1801, 1803, 1805 and/or germicidal devices 1807. Additionally or alternatively, software on the remote server 1809, human interface devices 1801, 1803,

1805, and/or germicidal devices 1807 may enable information to be exchanged automatically.

One or more germicidal devices, human interface devices, and/or remote devices or servers may be connected to and communicate over any suitable network type using any suitable communication protocol. For example, the network may be an intranet and/or a wireless network, such as a cellular telephone network, a wired or wireless local area network (LAN), and/or a metropolitan area network (MAN). In some variations, such as when the germicidal system is a cloud-based or hosted, web-based system, the network may be the Internet, also referred to as the World Wide Web (WWW). The wireless communication may use any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol.

Various types of information may be exchanged between a remote server and one or more human interface and/or germicidal devices over a network. For example, information originally obtained by a germicidal device may include data obtained via the signals detected by one or more germicidal device sensors (e.g., proximity sensors). As mentioned, in some variations, the germicidal device may be configured to send at least some of this information directly to the remote server. Additionally or alternatively, the germicidal device may be configured to send at least some information to an associated or connected human interface device, and the human interface device may in turn send the information to the remote server. The human interface device may obtain information from user input (e.g., a user may make selections or adjust operational parameters via a user interface) and/or data obtained via detection by one or more interaction sensors, and this information may be sent to the remote server. Other data that may be sent to the remote server by one or more human interface and/or germicidal devices may include device status or performance data, such as remaining bulb life, device location, disinfection protocol information, and/or device malfunction information. In some variations, one or more human interface and/or germicidal devices may be configured to store and/or analyze data, and this processed data may be sent to the remote server.

A remote server may receive, compile, store, analyze, and/or transmit information that is sent from one or more human interface and/or germicidal devices. An administrator may control what information is received by the remote server and the types of processing that may be done with this information. For example, an administrator may direct the remote server to receive information from the human interface and/or germicidal devices on a particular floor of a building and/or generate a report summarizing that information in a specific way.

Similarly, the remote server may send information to one or more human interface and/or germicidal devices, and an administrator may control what information is sent and which human interface and/or germicidal devices receive the information. In some variations, a germicidal system may be configured such that a remote server exchanges information with one or more human interface and/or germicidal devices automatically, with or without initial direction by an administrator. For example, a germicidal system may be configured so that one or more human interface and/or germicidal devices send status or performance data to a remote server with a predetermined frequency (e.g., every 6 hours, every day, every week). Additionally or alternatively, a germicidal system may be configured such that information may be sent from the remote server to one or more human interface and/or germicidal devices automatically when certain criteria are met. For example, the remote server may automatically assign a *C. diff* protocol to one or more germicidal devices if the remote server receives information, such as positive *C. diff* lab results, that indicate a *C. diff* outbreak.

The way that an administrator interacts or communicates with a remote server may depend on the configuration of the germicidal system, such as the type of network connected to the devices. In some variations, such as when the remote server, human interface devices, and/or germicidal devices are connected to a LAN or WAN, any device that is connected to the network and that comprises suitable software may be an administrator device. An administrator may input information via an administrator interface of the administrator device, and instructions based on this information may then be sent to the remote server. The instructions may direct the remote server to process information from or communicate information to the human interface and/or germicidal devices in a particular way. Similarly, the administrator may receive output (e.g., via an administrator interface display, printer) from the administrator device that was obtained from the remote server. The administrator device may be a device with an associated germicidal device or a device (e.g., computer, tablet, mobile phone) without an associated germicidal device. In some variations, a germicidal system may not comprise a separate remote server and administrator device, and the administrator device may also function as the server. For example, the computer that an administrator uses to select operational parameters for a plurality of human interface and/or germicidal devices may communicate directly with the plurality of human interface and/or germicidal devices. Similarly, the same computer may receive and process data from a plurality of human interface and/or germicidal devices and also provide this data to the administrator.

In some variations, a germicidal system may be a cloud-based or hosted, web-based system. For example, the Internet may be the network to which one or more human interface and/or germicidal devices and a remote server are connected. In this variation, an administrator device that an administrator may use to communicate with the remote server may be any device that is connected to the Internet. For example, a web browser on an administrator device may be used to interact with the remote server, rather than a dedicated germicidal program or application software being required. In an exemplary variation, the germicidal system may comprise a plurality of germicidal devices communicatively coupled with a remote server via a wireless network. Communicative coupling of a germicidal device with a remote server via a wireless network may be particularly useful for germicidal devices not connected to an associated human interface device (e.g., germicidal devices having standalone sensing systems as described herein). The remote server may in turn be communicatively coupled with an administrator device, such as a computer. An administrator (i.e., a user with access to germicidal software that may, for example, allow for control of more than one germicidal device) may input information into the administrator device (e.g., via an administrator interface). Instructions based on this information may be sent to the remote server via the network, and the instructions may then be sent to one or more of the plurality of germicidal devices via the network. As mentioned, in cloud or web-based germicidal systems, the network communicatively coupling the germicidal devices, remote server, and administrator device may be the Internet. In this variation, the germicidal system may comprise a web-based management system. In some variations, an administrator may access and interact with the web-based management system via a web browser on the administrator device.

The types of information that may be exchanged between a remote server and one or more human interface and/or germicidal devices and the ways that this information may be controlled and/or analyzed will be described in more detail in relation to various administrator interface screens. These representative screens, shown in FIGS. 19A-19K, may appear on an administrator device in a dedicated germicidal program or, in cloud or web-based germicidal systems, in a web browser. An administrator may make selections or input information on these screens (e.g., via a physical or virtual keyboard, a mouse, a touchscreen, a touchpad) in order to control the processing of information, the exchange of information between one or more devices of the germicidal system, and/or the configuration of or access to the germicidal system. In use, login information, such as a user name and password may be required for an administrator to access and/or make changes to at least some of these screens. It should be appreciated that these screens are representative of a suitable administrator interface and that the information contained on such screens may not be limited to or include all of what is shown and/or described. The representative screens depict one variation of a layout, and the information shown and/or described may have any suitable layout, including being displayed on any suitable number of screens, windows, and/or tabs. Also, one skilled in the art would recognize that any selectable or adjustable feature (e.g., drop-down menu, radio button, field) that is shown and/or described may be replaced with another suitable selectable or adjustable feature.

Figures 19A, 19B:
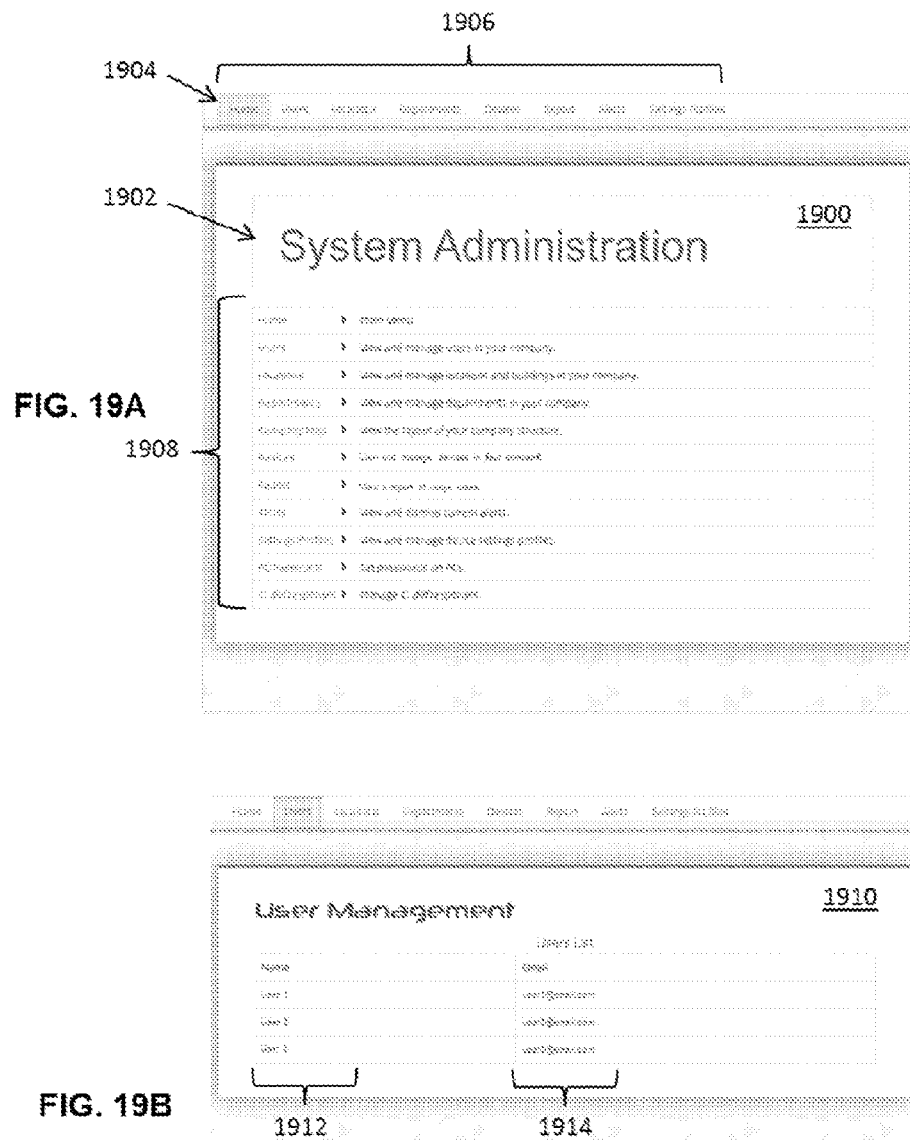
FIGS. 19A-19K show exemplary portions of an administrator interface.

FIG. 19A is a representative home or welcome screen of an administrator interface. In some variations, the home screen 1900 may be the first screen to which an administrator is directed when opening or logging into an administrator program. As may be the case with at least some of the other screens of the administrator interface, information may be shown that may identify the currently displayed screen and/or the content of the screen, such as a screen title 1902 and/or a highlighted or otherwise distinguished tab 1904. The home screen 1900 may display a list of windows, tabs, and/or categories of options that an administrator may access via the administrator interface. One or more such lists may be displayed in one or more forms, here as multiple named tabs 1906 and in a table 1908 that includes a description of each tab or category of options that an administrator may access. At least some of the information shown on the home screen 1900 and/or on other screens (e.g., at least a portion of displayed text, symbols, graphics) may be selected (e.g., via a mouse, keyboard, touchpad, touchscreen) in order to perform a function, such as navigating to a different screen or choosing a field to enter information. While not shown, in some variations, a home screen may display news, updates, alerts, and/or other information related to the germicidal system.

FIG. 19B is a representative user management screen of an administrator interface of a germicidal system. The user management screen 1910 may display one or more lists of users 1912 and information related to each user, here email addresses 1914. The users shown may be users who currently have or have requested access to one or more devices of the germicidal system. For example, the users may be users who have access to one or more human interface and/or germicidal devices (e.g., have access to functional software of one or more human interface and/or germicidal devices, may be capable or allowed to make changes to operational parameters of one or more germicidal devices, allowed to direct a device to generate a report related to one or more human interface and/or germicidal devices). In some variations, the users shown may be administrators who may have access to one or more screens of the administrator interface. The user list 1912 and/or information related to the users on the user list may be editable on the user management screen 1910. For example, new users may be added or existing users may be removed from the user list 1912.

Figure 19C:
Figure 19D:
Figure 19E:
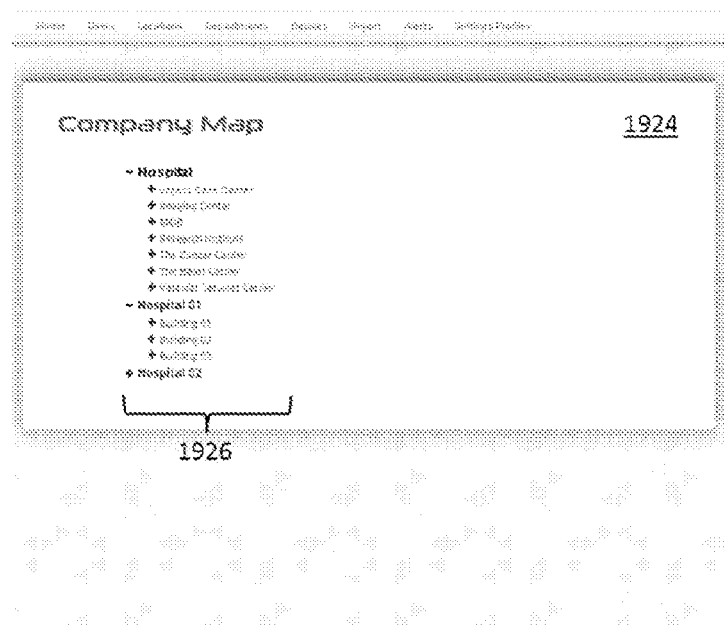

FIGS. 19C-E are representative screens of an administrator interface that may allow an administrator to setup, edit, and/or view information related to sites or areas in a company or organization that may utilize a germicidal system. Such information may be separated on different screens or organized on the same screen based on the type or size of the area that the information is related to, such as a general location that may have more than one building (e.g., hospital, campus, town or city), building, floor, department, wing, room, and/or asset. For example, the screen 1916 shown in FIG. 19C displays a list of general locations 1918, and the screen 1920 shown in FIG. 19D displays a list of departments 1922. The screen 1924 shown in FIG. 19E displays a list or map of multiple types of areas 1926, and the areas may be arranged in the map in one or more ways, such as hierarchically based on the size of the area. One or more of these screens 1916, 1920, 1924 may allow an administrator to make changes to the areas of a company or organization that may utilize the germicidal system. For example, an administrator may add, remove, and/or rename an area. For example, if one or more germicidal devices are utilized in a new area, an administrator may add that area. In some variations, a device of the germicidal system (e.g., a germicidal device, a human interface device) may send information about its location to a remote server automatically, and area information may change on a screen of the administrator interface automatically without manual administrator input.

Figure 19F:
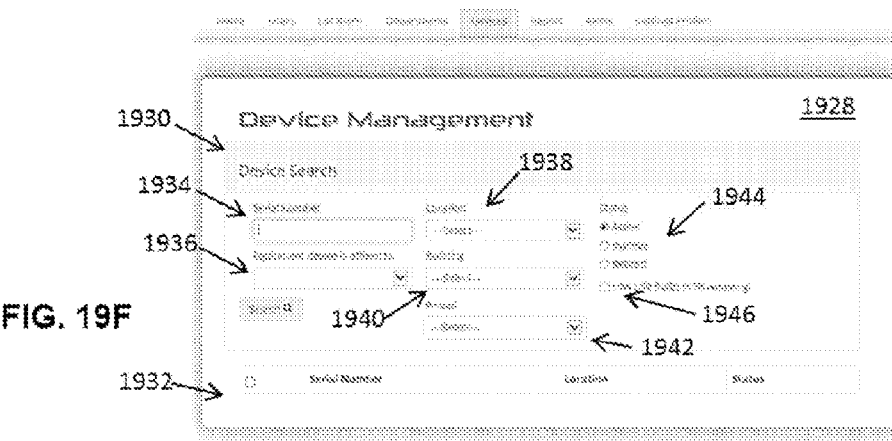

FIG. 19F is a representative device management screen of an administrator interface. The device management screen 1928 may allow an administrator to view and/or change one or more properties of one or more human interface and/or germicidal devices. The device management screen 1928 may display a device search area 1930 and a search results area 1932. The device search area 1930 may comprise one or more data fields for entering or selecting device information or criteria in order to search for one or more human interface and/or germicidal devices that meet the selected criteria. For example the device search area 1930 as shown comprises data fields that may allow an administrator to search for a device by an identifying or serial number 1934, equipment that the device is connected to 1936, a general location of the device 1938, a building where the device is located 1940, a disinfection protocol assigned to the device 1942, a status of the device (e.g., active, inactive, retired) 1944, and/or an amount of remaining bulb life 1946. The device search area 1930 may comprise data fields that allow an administrator to select any device criteria that is suitable to a particular germicidal system. For example, there may be data fields that allow an administrator to search for devices in specific rooms or departments if the germicidal system is utilized in an environment organized by room and department.

The search results area 1932 of the device management screen 1928 may display the devices of the germicidal system (e.g., human interface and/or germicidal devices) that meet the criteria selected in the device search area 1930. One or more properties (e.g., serial number, location, status, service log) of these devices may be displayed in the search results area 1932. In some variations, an administrator may select one or more of the devices displayed in the search results area 1932 in order to view more properties of the one or more devices. In some variations, the administrator may modify one or more of these device properties. For example, the administrator may select one or more devices and change the disinfection protocol assigned to the one or more devices. In some variations, the device management screen 1928 may comprise an area that may allow an administrator to add a new device to the germicidal system.

Figure 19G:
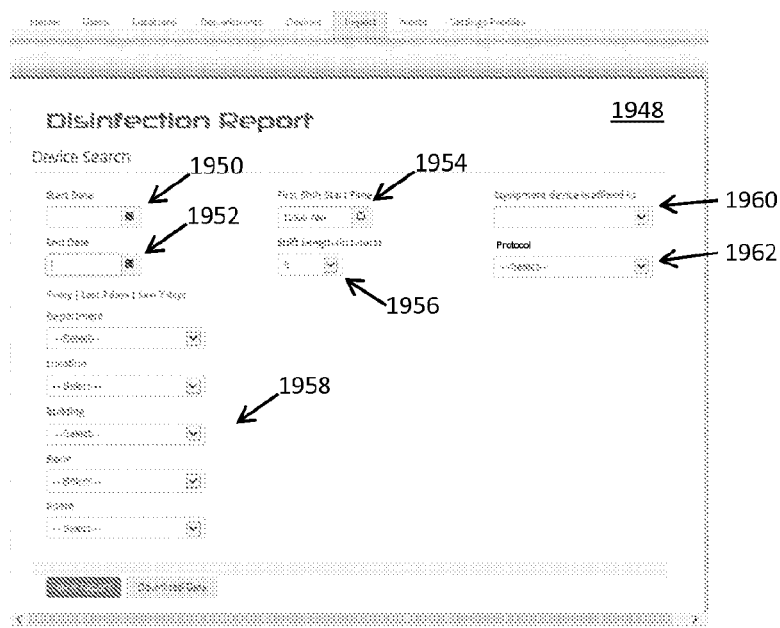

FIG. 19G is a representative report selection screen of an administrator interface of a germicidal system. The report selection screen 1948 may allow an administrator to select a type of report and/or parameters of a report to be generated and displayed. For example, the report selection screen 1948 may comprise one or more data fields that may allow an administrator to select the parameters of a disinfection report that may, for example, depict the number of disinfection cycles that have been performed by one or more selected germicidal devices over a selected time period and organized by selected time increments. As shown, the report selection screen 1948 comprises data fields that may allow an administrator to select parameters of a report including a start date of the report 1950, an end date of the report 1952, and time increments displayed on the report by shift start time 1954 and shift length 1956. Other data fields may allow an administrator to select the devices that are included in the report, including selecting one or more devices by area 1958 (e.g., general location, department, building, floor, room), equipment that the one or more devices is connected to 1960 (e.g., desktop computer, laptop computer, touchpad, touchscreen, touchscreen of a medical cart), a disinfection protocol assigned to the one or more devices 1962, and/or other device characteristics not shown such as serial number.

While the report selection screen 1948 in FIG. 19G shows options for generating a disinfection report, an administrator interface may display one or more screens that may include options for generating other types of reports. For example, a report selection screen may allow a report to be generated that lists or otherwise identifies devices based on certain characteristics, such as those with a certain status (e.g., active, inactive) and/or those having device errors, malfunctions, or other problematic events. In some variations the report selection screen may allow an administrator to specify parameters of a report that lists or otherwise identifies devices that have been continuously active for some predetermined time, such as 60 minutes or more; devices that have been inactive for long periods, such as 180 days; devices that have not been serviced in some predetermined interval, such as 180 days; and/or devices that may be running low on bulb life, such as those that have accumulated at least about 3000 hours of active or on time. In some variations, the report selection screen may allow for selections that provide input about activity levels near the germicidal devices and/or usage levels of human interface devices. For example, the report selection screen may allow an administrator to generate a report regarding detection events by a sensing system (e.g., number and/or timing of proximity sensor detection events, number and/or timing of interaction sensor events). It should be appreciated that any of the device characteristics that may be selected in the device search area 1930 of the device management screen 19F discussed with respect to FIG. 19F may be selected on a report selection screen in order to identify devices within a germicidal system that have the selected characteristics. In some variations, the report selection screen may allow an administrator to choose to have one or more report types automatically delivered (e.g., via e-mail) with a specified frequency (e.g., every day, every week) to one or more administrators or other individuals.

Figure 19H:
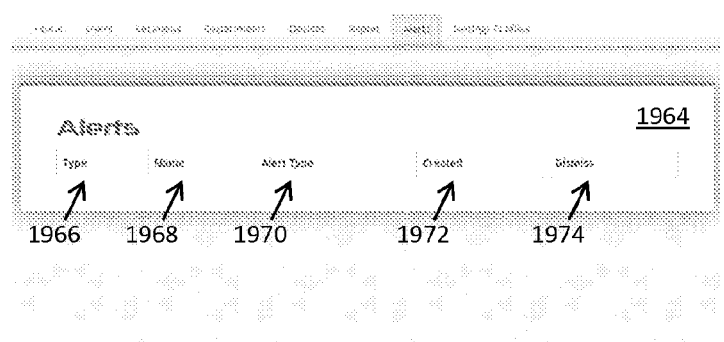

FIG. 19H is a representative alert screen of an administrator interface of a germicidal system. The alert screen 1964 may allow an administrator to view information related to alerts or warnings that have been sent by one or more devices of the germicidal system (e.g., one or more germicidal devices, human interface devices, remote servers). The alert screen 1964 may display information related to one or more devices that generated an alert, such as the type of device 1966 (e.g., germicidal device, type of human interface device), a name of the device 1968 (e.g., identifying number, code, serial number), a location of the device, a status of the device (active, inactive, retired), a disinfection protocol assigned to the device, and/or the like. In some variations, the alert screen may display information related to the one or more alerts, such as an alert type 1970 (e.g., device lost power, device malfunctioned for a known or unknown reason); a date and/or time when the alert was created 1972 (e.g., sent from a device, received by the remote server); and/or a date and/or time when the alert was dismissed 1974, acknowledged, and/or the issue causing the alert was resolved. The alert screen 1964 may display a log of alerts for a specified time period and/or from devices with specified characteristics (e.g., all devices in a germicidal system, all germicidal devices or human interface devices in a germicidal system, devices in a certain location). In some variations, the administrator may perform an action related to one or more displayed alerts, such as dismissing one or more alerts or generating a report that lists and/or displays statistics or other information related to one or more alerts.

Figure 19I:
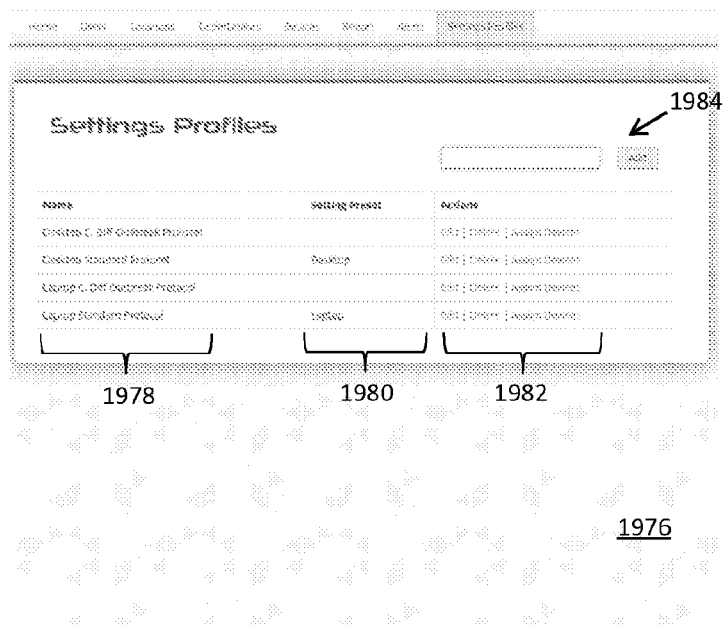

FIG. 19I is a representative settings profiles screen of an administrator interface of a germicidal system. The settings profiles screen 1976 may allow an administrator to view and/or modify one or more settings or parameters of the germicidal system. For example, the settings profiles screen 1976 may allow an administrator to view and/or modify one or more parameters of one or more disinfection protocols. As shown, the settings profiles screen may display names of disinfection protocols 1978 (e.g., desktop *C. diff* outbreak protocol, desktop standard protocol, laptop standard protocol) and a setting preset 1980 for any applicable disinfection protocols. The setting preset 1980 may indicate which devices or category of devices (e.g., category based on the location of the device, the type of equipment attached to the device) may be assigned a certain disinfection protocol currently or by default. For example, as shown, the desktop standard protocol has a setting preset of desktop, which may indicate that currently or by default, all germicidal devices in the germicidal system that are associated with a desktop computer may be assigned the desktop standard disinfection protocol. The settings profiles screen 1976 may also display one or more actions 1982 for each disinfection protocol that an administrator may select. For example, the actions 1982 may allow an administrator to edit the parameters of a disinfection protocol (e.g., the disinfection cycle duration, the periodic cycle duration the delay period, the periodic interval), delete a disinfection protocol, and/or assign one or more devices to a certain disinfection protocol. The settings profiles screen 1976 may also include a data field 1984 that allows an administrator to add or create a new disinfection protocol.

Figure 19J:
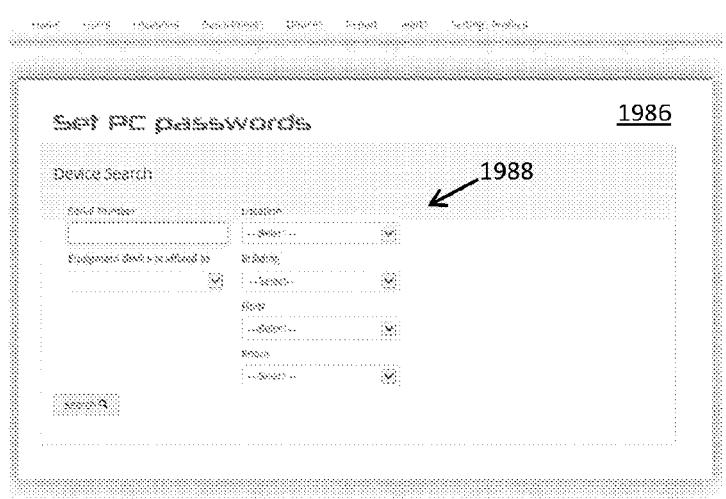

FIG. 19J is a representative password screen of an administrator interface of a germicidal system. The password screen 1986 may allow an administrator to view and/or change the password for one or more human interface and/or germicidal devices. For example, as described in more detail herein, a user may enter a password on a germicidal device and/or a human interface device in order to access functional germicidal software that may, for example, allow the user to change one or more operational parameters of the germicidal and/or human interface device. The password screen 1986 may comprise a device search area 1988 that may comprise one or more data fields for entering or selecting device information or criteria in order to search for one or more human interface and/or germicidal devices. These data fields may comprise any combination of the data fields discussed with respect to the device search area 1930 of the device management screen 1928 shown in FIG. 19F, such as data fields that allow an administrator to search for one or more devices by serial number, equipment the one or more devices are connected to, and/or a location. An administrator may select one or more of the devices that are displayed as search results, and the password for the one or more devices may be viewed and/or changed.

Figure 19K:
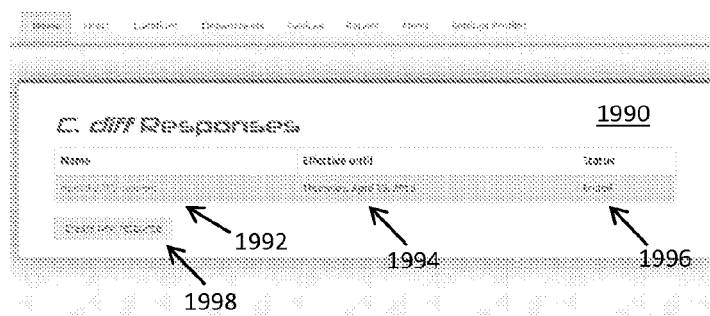

FIG. 19K is a representative *C. diff* response screen of an administrator interface of a germicidal system. The *C. diff* response screen 1990 may allow an administrator to view and/or modify past and/or current *C. diff* responses and/or create a new *C. diff* response. A *C. diff* response may be the parameters of the germicidal system that are set in response to a *C. diff* outbreak (e.g., when a number of patients above a specified threshold in a specified area have been diagnosed with *C. diff*). For example, a *C. diff* response may include the parameters of one or more *C. diff* disinfection protocols (e.g., duration of a disinfection cycle, d), the devices that are assigned to the one or more *C. diff* disinfection protocols (e.g., germicidal devices in a certain location), and/or the duration for which one or more devices are assigned to a *C. diff* disinfection protocol. The *C. diff* response screen 1990 may display names of current and/or past *C. diff* responses 1992 and information related to the current and/or past *C. diff* responses. As shown, the date each *C. diff* response is effective until 1994 and the status of the *C. diff* response 1996 (e.g., active, ended) are displayed. An administrator may select one or more *C. diff* responses shown on the *C. diff* response screen 1990 in order to view and/or modify one or more parameters of the response (e.g., the operational parameters of one or more devices, the devices that are assigned to one more *C. diff* disinfection protocols, the duration of the *C. diff* response). In some variations, one or more statistics or other data related to a *C. diff* response may be viewed by an administrator (e.g., the number of patients diagnosed in a particular area after the response was initiated). As shown, the *C. diff* response screen 1990 may include a field that may be selected by an administrator in order to create a new response 1998. While a *C. diff* response screen is shown, it should be appreciated that an administrator interface may comprise one or more response screens for other pathogens (e.g., MRSA, H1N1 flu virus, *E. Coli*).

Methods of Assigning a Disinfection Protocol

A method for disinfecting one or more surfaces may comprise assigning a disinfection protocol to one or more germicidal devices. A disinfection protocol may comprise operational parameters for one or more germicidal devices. For example, a disinfection protocol may comprise instructions directing a germicidal light source of a germicidal device to be illuminated for a specific duration when performing a disinfection cycle. As described in detail herein, the disinfection protocol assigned to a germicidal device (e.g., the disinfection protocol that a germicidal device is instructed to run, follow, execute) may depend on factors including the type of surface or type of device comprising the contact surface to be disinfected (e.g. desktop computer, laptop computer, touchscreen, mouse). In some variations, a specific disinfection protocol may be assigned to a germicidal device based on environmental factors, such as one or more specific pathogens suspected of being on the surface (e.g., *C. diff*, H1N1 flu virus). For example, if a *C. diff* outbreak occurs, germicidal devices in an area of the outbreak may be assigned a *C. diff* disinfection protocol, which may comprise operational parameters that allow a germicidal device to substantially disinfect a surface at least partially covered with *C. diff* bacteria.

In some variations, a disinfection protocol may be assigned to one or more germicidal devices by default when the one or more germicidal devices is initially powered on and/or set up by a user or administrator. For example, when a germicidal device is initially connected to a human interface device, the germicidal system may determine the type of human interface device (e.g., desktop computer, laptop computer, tablet, touchscreen). This determination may be performed using software stored in memory of the germicidal system (e.g., memory of the germicidal device, human interface device, and/or server) and executed by a processor of the germicidal system (e.g., a processor of the germicidal device, human interface device, and/or server). In response to this determination, a specific disinfection protocol may be assigned to the germicidal device (e.g., desktop protocol, laptop protocol, tablet protocol, touchscreen protocol).

In some variations, a method for disinfecting one or more surfaces may comprise manually assigning a disinfection protocol to one or more germicidal devices at initial set up and/or at a later time in response to one or more environmental factors. A disinfection protocol may be assigned to a germicidal device locally (e.g., via software installed on an associated human interface device) and/or remotely over a network. For example, for a germicidal device comprising a dual-mode sensing system and connected to a human interface device, a user may assign a disinfection protocol to the germicidal device by accessing a user interface of the human interface device that is associated with (e.g., connected to, coupled to, communicatively coupled with, nearby) the germicidal device. In some variations, this method may comprise the user navigating to a screen generated by the software and displayed on the user interface, such as the representative operation screens discussed with respect to FIGS. 16A and 16B. In some variations, a user may input parameters of the disinfection protocol to be assigned, such as the duration of a disinfection cycle and/or the delay between a detection event and the start of the disinfection cycle. In other variations, a user may select a disinfection protocol with predetermined parameters (e.g., desktop protocol, laptop protocol, C. diff protocol). In response to user input via the user interface of the human interface device, a disinfection protocol may be assigned to the germicidal device associated with the human interface device (i.e., instructions for specific operational parameters of the germicidal device may be stored in memory of the human interface and/or germicidal device). In other words, a human interface device may provide a user interface and receive user input (e.g., a selection of a disinfection protocol, disinfection protocol parameters). In response to the user input, the human interface device may assign a disinfection protocol, or transmit instructions to perform a specific disinfection protocol, to an associated germicidal device.

In some variations, a method for disinfecting one or more surfaces may comprise assigning one or more disinfection protocols to one or more germicidal devices via a network (e.g., LAN, WAN, the Internet). In these variations, an administrator may access an administrator interface of an administrator device connected to the network. The administrator may navigate to a screen generated by the germicidal software and displayed on the administrator interface, such as the representative settings profiles screen shown in FIG. 19I. The administrator may set the operational parameters (e.g., disinfection cycle length, delay period) of one or more disinfection protocols and/or assign the same or different disinfection protocols to one or more germicidal devices of the germicidal system. For example, an administrator may search for germicidal devices using one or more criteria, such as the type of human interface device (e.g., desktop, laptop) associated with the germicidal device and/or the location of the germicidal device (e.g. building, floor, wing). In response to selected search criteria, software of the germicidal system may provide a list of germicidal devices that meet these criteria on the administrator interface. An administrator may select one or more of these germicidal devices, and in response to this administrator input, operational parameters may be adjusted and/or a disinfection protocol may be assigned to the one or more selected germicidal devices. In other words, the germicidal system may provide an administrator interface on an administrator device and receive administrator input via the administrator interface (e.g., one or more germicidal device search criteria). In response to the administrator input, the germicidal system may perform a search for one or more germicidal devices corresponding to the one or more search criteria and display a list of the one or more germicidal devices on the administrator interface. The germicidal system may receive an administrator selection (e.g., a selection of one or more germicidal devices from the list, a selection of a disinfection protocol), and in response to this selection, assign a disinfection protocol, or transmit instructions to perform a specific disinfection protocol, to the one or more selected germicidal devices.

Instructions for performing the selected disinfection protocol may be delivered from the administrator device and received by a server via a network. The instructions may then be delivered from the server and received by the one or more germicidal devices via the network. In some variations in which a germicidal device is communicatively coupled to a human interface device, such as in germicidal devices comprising dual-mode sensing systems described herein, sending instructions for the disinfection protocol from the server to the one or more germicidal devices may be indirect. In other words, the instructions for the disinfection protocol may be sent from the server to one or more human interface devices, and then from the one or more human interface devices to one or more germicidal devices associated with those human interface devices. The instructions for specific operational parameters of the germicidal device may be stored in memory of the administrator device, server, human interface device, and/or germicidal device.

One particular example of when a disinfection protocol may be assigned to one or more germicidal devices may be in response to a C. diff outbreak in a healthcare setting. Because longer exposure times (e.g., either disinfection cycle durations or periodic cycle durations) may be more effective in disinfecting contact surfaces contaminated with C. diff, when C. diff is likely to be found in a particular area of a healthcare setting (e.g., one or more rooms, a wing, a floor, a building, or the like), it may be desirable to assign a new disinfection protocol to the germicidal devices located in these areas. In some of these instances, in response to information indicating that C. diff is likely to be found at the location of one or more germicidal devices, an administrator may use an administrator interface to select the germicidal devices as described herein, and may assign predetermined C. diff protocols to each of the germicidal devices. In some instances, different predetermined C. diff protocols may be sent to different devices, for example based on their location, mounting assembly, and/or contact surface. The instructions for performing the assigned protocols may be delivered from the administrator device to a server via a network, and may then be received by the germicidal devices via the network, and in some instances, via a human interface device.

Methods of Generating Reports

As discussed in detail herein, a germicidal system may be configured to generate one or more types of reports displaying information related to the germicidal system. In some variations, a method for generating a report may comprise obtaining information via a user interface of a human interface device. Using this method, a report may be generated that relates to the human interface device and/or an associated germicidal device. In other variations, the method for generating a report may comprise obtaining information via an administrator interface of an administrator device, which may or may not have an associated germicidal device. Using this method, a report may be generated that relates to one or more human interface and/or germicidal devices that are connected to the same network as a server and the administrator device.

A method for generating a report related to a germicidal system may comprise a human interface device obtaining user input via a user interface of the human interface device. For example, a user may access the user interface of the human interface device, and in some variations, navigate to a screen, such as the representative report screen shown in FIG. 16D. This and other suitable report screens may be generated by germicidal software that is stored in memory of the human interface device and/or an associated germicidal device and displayed on the user interface of the human interface device. A report screen may display one or more selectable or adjustable options that may allow a user to determine parameters of the report to be generated. Examples of such options and parameters are shown and/or described with respect to FIG. 16D and FIG. 17. A user may provide input to the human interface device by selecting and/or adjusting one or more parameters (i.e., any of the options or parameters discussed with respect to FIG. 16D or FIG. 17) on the report screen.

In response to the user input, the human interface device (e.g., a processor of the human interface device) may generate a report based on the selected parameters. At least some of the data used to generate the report may be obtained from memory of the germicidal device and/or the human interface device. The report may be output to the user interface in order to be viewed by the user, to memory of the human interface device and/or germicidal device in order to be stored, and/or to one or more other devices (printer, remote server via a network). The output destination of the report may be determined based on user input via the user interface. In other words, a human interface device may provide a user interface and receive user input (e.g., a selection of one or more report parameters). In response to the user input, the human interface device may display, store, and/or otherwise output a report corresponding to the selected report parameters.

In some variations, a method for generating a report related to a germicidal system may comprise a server obtaining administrator input via an administrator interface of an administrator device. For example, the germicidal system may provide the administrator interface on an administrator device that is connected to the same network as a server and one or more germicidal and/or human interface devices. In this variation, germicidal software may be stored in memory of the administrator device, the server, one or more human interface devices, and/or one or more germicidal devices. The administrator may navigate to a screen, such as the report selection screen shown in FIG. 19G, which may be generated by the germicidal software and displayed on the administrator interface. The screen shown on the administrator interface may include one or more selectable options that may allow an administrator to determine the parameters of the report to be generated. For example, an administrator may choose to have a report generated that includes information related to any number of germicidal and/or human interface devices in the germicidal system, such as the germicidal and human interface devices in a particular building, on a particular floor, in a particular department, or the like. It should be appreciated that a germicidal system may receive administrator input corresponding to one or more selections of any suitable report options and parameters, including but not limited to those shown and/or described with respect to FIG. 19G.

In response to the administrator input, a processor of the germicidal system (e.g., one or more processors of the administrator device, server, human interface devices, and/or germicidal devices) may generate a report based on the selected parameters and using data obtained from memory of the germicidal system (e.g., memory of the server, administrator device, one or more human interface devices, and/or one or more germicidal devices). The processor of the germicidal system that generates the report may obtain the necessary input and data via the network. The report may be output to the administrator interface of the administrator device in order to be viewed by the administrator, stored in memory of the germicidal system, and/or output to any other device connected to the network. The one or more output destinations may be determined based on administrator input via the administrator interface.

While the inventive devices, systems, and methods have been described in some detail by way of illustration, such illustration is for purposes of clarity of understanding only. It will be readily apparent to those of ordinary skill in the art in light of the teachings herein that certain changes and modifications may be made thereto without departing from the spirit and scope of the appended claims. For example, it should be appreciated by those skilled in the art that elements of the germicidal devices, systems, and methods described herein may be combined in alternative ways not expressly described herein.

What is claimed is:

1. A system for disinfecting one or more surfaces, comprising:
   a plurality of germicidal devices, wherein each germicidal device comprises a germicidal light source including a processor for controlling disinfection cycles and a sensor capable of detecting a person is within an illumination area of the germicidal light source and interrupting a disinfection cycle by shutting off the germicidal light source, wherein each germicidal device is configured to automatically transmit disinfection cycles data representative of the number of completed disinfection cycles and completeness of partially completed disinfection cycles;
   a server communicatively coupled to the plurality of germicidal devices via a network, wherein the server is configured to assign different disinfection protocols from among a plurality of disinfection protocols to subsets of the plurality of germicidal devices, provide instructions to the plurality of germicidal devices via the network to control the plurality of germicidal devices according to their assigned disinfection protocols, and collect disinfection cycles data from each of the plurality of germicidal devices via the network;
   an administrator device communicatively coupled to the server, wherein the administrator device comprises an administrator interface, and wherein the administrator device is configured to receive input via the administrator interface and to provide instructions via the network; and
   wherein, in response to the instructions transmitted via the network from the administrator device, at least one germicidal device of the plurality of germicidal devices adjusts one or more germicidal device operational parameters.

2. The system of claim 1, wherein the server is indirectly communicatively coupled to the germicidal device via a human interface device, wherein the one or more surfaces to be disinfected is part of or a peripheral device of the human interface device.

3. The system of claim 1, wherein the instructions control one of the subsets of the plurality of germicidal devices.

4. The system of claim 1, wherein the germicidal devices are wirelessly connected to the network, and wherein the instructions include a selection of one or more of the plurality of germicidal devices and a disinfection protocol selection, wherein, in response to the instructions, the server is configured to change the assigned disinfection protocol of the selected one or more of the plurality of germicidal devices to the disinfection protocol selection.

5. The system of claim 1 wherein the instructions control all germicidal devices assigned a same device-specific disinfection protocol.

6. The system of claim 1 wherein the collected disinfection cycles data from each of the plurality of germicidal devices via the network includes information regarding completed disinfection cycles and partially completed disinfection cycles for multiple germicidal devices sharing a disinfection protocol over a selected time period and organized by selected time increments.

7. The system of claim 1, wherein in response to a positive pathogen result, instructions are provided automatically to assign a pathogen-specific protocol to one or more germicidal devices located proximal to the location of the positive pathogen result.

8. A method for controlling a germicidal system, wherein the germicidal system comprises a plurality of germicidal devices each including a sensor capable of detecting a person is within an illumination area of the germicidal device and interrupting a disinfection cycle by shutting off the germicidal device, each one of the plurality of germicidal devices communicatively coupled to an administrator device via a network, the method comprising:
    each of the plurality of germicidal devices automatically communicating disinfection cycles data representative of the number of completed disinfection cycles and completeness of partially completed disinfection cycles via the network to the administrator device;
    collecting disinfection cycles data from each of the plurality of germicidal devices via the network;
    assigning, by an administrator device, different disinfection protocols from among a plurality of disinfection protocols to subsets of the plurality of germicidal devices;
    transmitting instructions over the network to the plurality of germicidal devices to control the plurality of germicidal devices according to their assigned disinfection protocol;
    in response to the instructions transmitted over the network, adjusting one or more operational parameters of at least one of the germicidal devices.

9. The method of claim 8, wherein the one or more operational parameters include at least one of a disinfecting cycle duration and a periodic cycle duration.

10. The method of claim 9, wherein at least one of the disinfecting cycle duration and the periodic cycle duration is increased.

11. The method of claim 10, wherein the increase is in response to a pathogen outbreak.

12. The method of claim 8, wherein an administrator input comprises a selection of at least two of the plurality of germicidal devices and wherein the method includes simultaneously controlling all of the at least two of the plurality of germicidal devices.

13. The method of claim 8, wherein an administrator input comprises a selection of one or more operational parameters of at least two of the plurality of germicidal devices.

14. The method of claim 8, wherein adjusting one or more operational parameters of the at least one germicidal device comprises transmitting instructions to the at least one germicidal device.

15. The method of claim 8 including in response to the instructions controlling all germicidal devices assigned a same device-specific disinfection protocol.

16. The method of claim 8 including receiving, at the administrator device via the network, information regarding completed disinfection cycles and partially completed disinfection cycles for multiple germicidal devices sharing a disinfection protocol over a selected time period and organized by selected time increments.

17. The method of claim 8 including automatically assigning a pathogen-specific protocol to one or more germicidal devices in response to the administrator device receiving a positive pathogen result.

18. A method for disinfecting one or more surfaces using a plurality of germicidal devices, wherein each germicidal device comprises a germicidal light source and a sensor, and wherein each germicidal device is associated with a human interface device and communicatively coupled to a server via a network, the method comprising:
    in response to detecting at least one of an interaction with the human interface device and human proximity with the sensor, associated with one of the plurality of germicidal devices, beginning a presence-based disinfection cycle of that germicidal device, wherein the presence-based disinfection cycle comprises a delay period without disinfection followed by irradiating a surface associated with the human interface device associated with that germicidal device using the germicidal light source of that germicidal device for a disinfection cycle duration;
    beginning a periodic disinfection cycle for each of the plurality of germicidal devices, wherein the periodic disinfection cycle comprises a periodic interval without disinfection and irradiating the surface associated with the human interface device connected to each respective germicidal device using the germicidal light source for a periodic cycle duration;
    interrupting at least one of the presence-based disinfection cycle and the periodic disinfection cycle of at least one of the plurality of germicidal devices in response to detecting at least one of a human interaction and human proximity via the sensor of a respective one of the plurality of germicidal devices;
    in response to the interrupting the presence-based disinfection cycle during the delay period, resetting the delay period of the respective germicidal device before beginning the disinfection cycle duration;
    in response to interrupting at least one of the presence-based disinfection cycle during the disinfection cycle duration and the periodic disinfection cycle during the periodic cycle duration, shutting off the germicidal light source; and
    communicating disinfection cycles data via the network from the plurality of germicidal devices to the server, wherein the disinfection cycles data includes representations of a number of completed periodic disinfection cycles, a number of completed presence-based disinfection cycles, a number of partially completed periodic disinfection cycles, completeness of the partially completed disinfection cycles, a number of partially completed presence-based disinfection cycles, and completeness of the partially completed presence-based disinfection cycles;
    collecting, at the server, disinfection cycles data from each of the plurality of germicidal devices via the network;
    assigning, by the server, different disinfection protocols from among a plurality of disinfection protocols to subsets of the plurality of germicidal devices;
    transmitting instructions over the network to the plurality of germicidal devices to control the plurality of germicidal devices according to their assigned disinfection protocol;
    in response to the instructions transmitted over the network to the plurality of germicidal devices, adjusting one or more operational parameters of each germicidal device, wherein the one or more operational parameters includes at least one of the delay period without disinfection and the periodic interval without disinfection.

19. The method of claim 18, wherein the periodic cycle duration is longer than the disinfection cycle duration.

20. The method of claim 18, wherein the periodic cycle duration is between 0.5 and 4 times the disinfection cycle duration.

21. The method of claim 18, further comprising ending at least one of the disinfection cycle and the periodic disinfection cycle of a respective germicidal device in response to detection of interaction with the human interface device associated with the respective germicidal device, and pausing at least one of the disinfection cycle and the periodic disinfection cycle of the respective germicidal device in response to a detection event by the sensor of the respective germicidal device.

22. The method of claim 18 including, in response to the instructions, controlling all germicidal devices assigned a same device-specific disinfection protocol.

23. The method of claim 18 including collecting information regarding completed disinfection cycles and partially completed disinfection cycles at the server for multiple germicidal devices sharing a disinfection protocol over a selected time period and organized by selected time increments.

24. The method of claim 18 including receiving instructions from the server to assign a pathogen-specific protocol to one or more germicidal devices in response to the administrator device receiving a positive pathogen result.

* * * * *